United States Patent
Cho et al.

(10) Patent No.: US 7,179,832 B2
(45) Date of Patent: Feb. 20, 2007

(54) GLYCOGEN SYNTHASE KINASE 3β INHIBITOR, COMPOSITION AND PROCESS FOR THE PREPARATION THEREOF

(75) Inventors: Joong Myung Cho, Daejeon (KR); Seonggu Ro, Daejeon (KR); Tae Gyu Lee, Daejeon (KR); Kyung Joo Lee, Daejeon (KR); Dongkyu Shin, Daejeon (KR); Young-Lan Hyun, Daejeon (KR); Seung Chul Lee, Daejeon (KR); Jin Hwan Kim, Daejeon (KR); Young Ho Jeon, Daejeon (KR)

(73) Assignees: Crystalgenomics, Inc., Seoul (KR); Yuyu Inc., Kyungki-do (KR)

( * ) Notice: Subject to any disclaimer, the term of this patent is extended or adjusted under 35 U.S.C. 154(b) by 0 days.

(21) Appl. No.: 10/543,177

(22) PCT Filed: Jan. 20, 2004

(86) PCT No.: PCT/KR2004/000097

§ 371 (c)(1),
(2), (4) Date: Jul. 22, 2005

(87) PCT Pub. No.: WO2004/065370

PCT Pub. Date: Aug. 5, 2004

(65) Prior Publication Data

US 2006/0079521 A1    Apr. 13, 2006

(30) Foreign Application Priority Data

Jan. 23, 2003 (KR) .................. 10-2003-0004607
Jan. 23, 2003 (KR) .................. 10-2003-0004608
Jun. 27, 2003 (KR) .................. 10-2003-0042442

(51) Int. Cl.
*A61K 31/4184* (2006.01)
*C07D 235/18* (2006.01)

(52) U.S. Cl. .................. 514/394; 548/310.7
(58) Field of Classification Search ............ 548/310.7; 514/394
See application file for complete search history.

(56) References Cited

U.S. PATENT DOCUMENTS

| 5,821,258 | A | 10/1998 | Matsunaga et al. |
| 6,310,082 | B1 | 10/2001 | Griffin et al. |
| 6,509,365 | B1 * | 1/2003 | Lubisch et al. ............. 514/393 |

FOREIGN PATENT DOCUMENTS

| WO | WO 95/07263 A1 | 3/1995 |
| WO | WO-00/29384 A1 * | 5/2000 |
| WO | WO 02/102978 A2 | 12/2002 |

* cited by examiner

*Primary Examiner*—Laura L. Stockton
(74) *Attorney, Agent, or Firm*—Sughrue Mion, PLLC

(57) ABSTRACT

Novel compounds having hydroxybenzoimidazole carboxylic amide are useful for inhibiting glycogen synthase kinase 3β(GSK-3β).

6 Claims, No Drawings

GLYCOGEN SYNTHASE KINASE 3β INHIBITOR, COMPOSITION AND PROCESS FOR THE PREPARATION THEREOF

FIELD OF THE INVENTION

The present invention relates to a compound for inhibiting glycogen synthase kinase 3beta (GSK-3β) activity, a pharmaceutical composition containing the compound as an active ingredient and a process for the preparation thereof.

BACKGROUND OF THE INVENTION

Glycogen synthase kinase 3 (GSK-3), the well-known target protein for the treatment of diabetes and dementia, is a serine/threonine protein kinase which inhibits the activity of glycogen synthase (GS) by way of phosphorylation.

In the fatty tissue of mice suffering from fatty diabetes, the GSK-3β activity has been observed to be 2 fold higher than that of a normal mouse (H. Eldar-Finkelman, *Diabetes*, 48:1662–1666 (1999)) and patients during the second type diabetes are characterized by a high expression level of GSK-3β than normal (S. E. Nikoulina et al., *Diabetes*, 49: 263–171 (2000)). Also, the GSK-3β activity in the brain of a dementia patient is high (Yamaguchi H. et al., *Acta. Neuropathol.*, 92: 232–241 (1996)), and transgenic mice programmed to express GSK-3β in the brain have abnormal neurons caused by hyperphosphorylating tau of the neurofibrillary tangle which plays an important role in the dementia attack (Lucas J. J. et al., *EMBO J.* 20: 27–39 (2001)).

GSK-3β is further related to bipolar disorder which can be treated by lithium and valproic acid, well-known GSK-3β inhibitors (Elahi S. et al., *J. Infect. Dis.* 176: 217–226 (1997)).

Thus, there has existed a need to develop an effective inhibitor of GSK-3β for treating or preventing GSK-β-dependent diseases.

The present inventors have endeavored to develop an effective inhibitor of GSK-3β; and have unexpectedly found that a compound containing a hydroxybenzoimidazole carboxylic amide moiety can inhibit the activity of GSK-3β, and therefore, can be used for treating or preventing GSK-β-dependent diseases such as fatness, diabetes and dementia.

SUMMARY OF THE INVENTION

Accordingly, it is an object of the present invention to provide a GSK-3β inhibitor having high inhibitory activity against GSK-3β.

It is another object of the present invention to provide a process for preparing said inhibitor.

It is further object of the present invention to provide a pharmaceutical composition for inhibiting GSK-3β.

In accordance with one aspect of the present invention, there is provided a compound of formula (I), a pharmaceutically acceptable salt, hydrate, solvate or isomer thereof:

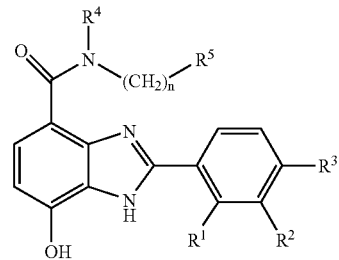

I wherein:
n is 0, 1, 2 or 3;
$R^1$, $R^2$ and $R^3$ are each independently hydrogen, hydroxy, halogen or morpholin-1-yl-ethylamino;
$R^4$ and $R^5$ are each independently hydrogen;
linear or cyclic $C_1$–$C_6$ alkyl optionally having one or more substituents, the carbon of the alkyl being optionally replaced with nitrogen, sulfur or oxygen, wherein the substituent is: hydroxy; halogen; alkyloxy; alkyl; amino; alkylamino; carboxyl; nitro; sulfonylamido; alkanesulfonyl; amido; an aromatic group optionally having one or more substituents selected from the group consisting of hydroxy, halogen, alkyloxy, alkyl, amino, alkylamino, carboxyl, nitro, amido, dioxoisoindole and sulfonylamino; an aromatic group having one or more substituents selected from the group consisting of hydroxy, halogen, alkyloxy, alkyl, amino, alkylamino, carboxyl, nitro and amido, the aromatic ring having nitrogen, sulfur or oxygen; or cyclic $C_3$–$C_8$ alkyl optionally having one or more substituents selected from the group consisting of hydroxy, halogen, alkyloxy, alkyl, amino, alkylamino, carboxyl, nitro and amido;

an aromatic group optionally having one or more substituents, the aromatic ring having optional nitrogen, sulfur or oxygen, wherein the substituent is: hydroxy; halogen; alkyloxy; alkyl; amino; alkylamino; carboxyl; nitro; sulfonylamido, alkanesulfonyl; amido; or linear or cyclic $C_1$–$C_6$ alkyl optionally having one or more substituents, the alkyl having an optional nitrogen, sulfur or oxygen linkage and the substituent of the alkyl being: hydroxy; halogen; alkyloxy; alkyl; amino; alkylamino; carboxyl; nitro; sulfonylamido, alkanesulfonyl; amido; an aromatic group optionally having one or more substituents selected from the group consisting of hydroxy; halogen; alkyloxy; allyl; amino; alkylamino; carboxyl; nitro; amido; dioxoisoindole; and a sulfonylamino having an aromatic group substituted with hydroxy, halogen, alkyloxy, alkyl, amino, alkylamino, carboxyl, nitro, sulfonylamido, alkanesulfonyl or amido; an aromatic group optionally having one or more substituents selected from the group consisting of hydroxy, halogen, alkyloxy, alkyl, amino, alkylamino, carboxyl, nitro, sulfonylamide, alkanesulfonyl and amido, the aromatic ring containing nitrogen, sulfur or oxygen; or a cyclic $C_3$–$C_8$ alkyl optionally having one or more substituents selected from the group consisting of hydroxy, halogen, alkyloxy, alkyl, amino, alkylamino, carboxyl, nitro and amido; or form, together with the —N—$(CH_2)_n$— moiety to which they are attached, a nitrogen heterocycle optionally having one or more substituents selected from the group consisting of OH, $NH_2$, $NO_2$, the heterocycle containing optional nitrogen or oxygen.

DETAILED DESCRIPTION OF THE INVENTION

Among the compounds of formula (I) of the present invention, the preferred are:

those wherein n, $R^1$, $R^2$ and $R^3$ have the same meanings as defined previously;

$R^4$ and $R^5$ are each independently hydrogen;

$C_1$–$C_4$ alkyl optionally having one or more substituents selected from the group consisting of OH, $NH_2$, $NO_2$, and an aromatic group, the aromatic group optionally having one or more substituents selected from the group consisting of OH, $C_1$–$C_4$ alkyloxy, $NH_2$, $NO_2$, methanesulfonylamino, ethanesulfonylamino, tolunesulfonylamino and dioxoisoindole; cyclic $C_3$–$C_8$ alkyl optionally having one or more substituents selected from the group consisting of OH, $NH_2$ and $NO_2$; $C_1$–$C_4$ alkyl carrying a morpholine or oxopyrrolidine group which is optionally substituted with OH, $NH_2$, $NO_2$ or —O—; $C_1$–$C_4$ alkyl or $C_1$–$C_4$ aminoalkyl carrying a pyrrole, pyrazole, imidazole, 1,2,3-triazole, 1,2,4-triazole, isoxazole, oxazole, isothiazole, thiazolidine, tiazole, 1,2,5-oxadiazole, 1,2,3-oxadiazole, 1,2,5-thiadiazole, 1,2,3-thiadiazole, 1,3,4-oxadiazole, 1,3,4-thiadiazole, pyridine, pyrimidine or triazine group which is optionally having one or more substituents selected from the group consisting of Cl, OH, $NH_2$, $NO_2$, $C_1$–$C_4$ and phenyl;

cyclic $C_3$–$C_8$ alkyl optionally having one or more substituents selected from the group consisting of OH, $NH_2$ and $NO_2$;

an aromatic group optionally having one or more substituents selected from the group consisting of OH; $NH_2$; hydroxyalkyl; aminoalkyl; $NO_2$; and a $C_1$–$C_4$ alkyl group optionally having one or more substituents selected from the group consisting of OH, $NH_2$, $NO_2$, methanesulfonylamino, ethanesulfonylamino, tolunensulfonylamino, dioxoisoindole and thiophensulfonylamino; or form, together with the —N—$(CH_2)_n$— moiety to which they are attached, a nitrogen heterocycle optionally having one or more substituents selected from the group consisting of OH, $NH_2$ and $NO_2$, the heterocycle containing 1 to 3 nitrogen, sulfur or oxygen atom.

In the present invention, the compounds of formula (I) as the below are most preferred: those wherein n, $R^1$, $R^2$ and $R^3$ have the same meanings as defined previously; $R^4$ and $R^5$ are each independently hydrogen;

$C_1$–$C_4$ alkyl optionally having one or more substituents selected from the group consisting of OH, $NH_2$, $NO_2$, morpholine, nitropyridineamino, pyridine, oxopyrrolidine, imidazole optionally having a Cl, $CH_3$ or phenyl substituent; and phenyl optionally having one or more substituents selected from the group consisting of OH, $NH_2$, methoxy, $NO_2$, methanesulfonylamino, ethanesulfonylamino, toluenesulfonylamino and dioxoisoindole;

cyclic $C_3$–$C_8$ alkyl optionally having one or more substituents selected from the group consisting of OH, $NH_2$ and $NO_2$;

phenyl optionally having one or more substituents selected from the group consisting of OH; $NH_2$; $NO_2$; and $C_1$–$C_4$ alkyl optionally having a OH, $NH_2$, $NO_2$, methanesulfonylamino, ethanesulfonylamino, tolunesulfonylamino, dioxoisoindole or thiophensulfonylamino substituent; or form, together with —N—$(CH_2)_n$— moiety to which they are attached, a piperidine ring optionally having one or more substituents selected from the group consisting of OH, $NH_2$ and $NO_2$.

Important compounds of the present invention are listed in Table 1 below.

TABLE 1

| Com No. | n | $R^1$ | $R^2$ | $R^3$ | $R^4$ | $R^5$ |
|---|---|---|---|---|---|---|
| 1 | 0 | H | H | H | H | H |
| 2 | 0 | H | H | H | H | Phenyl |
| 3 | 0 | H | H | H | H | 4-hydroxyphenyl |
| 4 | 0 | H | H | H | H | 4-aminophenyl |
| 5 | 0 | H | H | H | H | 4-hydroxycyclohexyl |
| 6 | 0 | H | H | H | H | 4-(hydroxymethyl)phenyl |
| 7 | 0 | H | H | H | H | 4-(hydroxyethyl)phenyl |
| 8 | 0 | H | H | H | H | 4-(aminoethyl)phenyl |
| 9 | 0 | H | H | H | H | 4-(p-toluenesulfonamidylethyl)phenyl |
| 10 | 0 | H | H | H | H | 4-(methanesulfonamidylethyl)phenyl |
| 11 | 0 | H | H | H | H | 4-(phthalinidylethyl)phenyl |
| 12 | 0 | H | H | H | H | 4-(2-thiophenylsulfonamidylethyl)phenyl |
| 13 | 0 | H | H | H | H | 4-(ethansulfonamidylethyl)phenyl |
| 14 | 0 | H | H | Cl | H | phenyl |
| 15 | 0 | H | H | Cl | H | 4-hydroxycyclohexyl |
| 16 | 0 | H | H | Cl | H | 4-(p-toluenesulfonamidylethyl)phenyl |
| 17 | 0 | H | H | Cl | H | 4-(methanesulfonamidylethyl)phenyl |
| 18 | 0 | H | H | Cl | H | 4-(phthalinidylethyl)phenyl |
| 19 | 0 | H | H | Cl | H | 4-(2-thiophenylsulfonamidylethyl)phenyl |
| 20 | 0 | H | H | Cl | H | 4-(ethansulfonamidylethyl)phenyl |
| 21 | 0 | Cl | H | Cl | H | H |
| 22 | 0 | Cl | H | Cl | H | Phenyl |
| 23 | 0 | Cl | H | Cl | H | 4-hydroxycyclohexyl |
| 24 | 0 | Cl | H | Cl | H | 4-(aminoethyl)phenyl |
| 25 | 0 | Cl | H | Cl | H | 4-aminophenyl |
| 26 | 0 | Cl | H | Cl | H | 4-(hydroxymethyl)phenyl |
| 27 | 0 | Cl | H | Cl | H | 4-(hydroxyethyl)phenyl |
| 28 | 0 | Cl | H | Cl | H | 4-(p-toluenesulfonamidylethyl)phenyl |
| 29 | 0 | Cl | H | Cl | H | 4-(methanesulfonamidylethyl)phenyl |
| 30 | 0 | Cl | H | Cl | H | 4-(phthalinidylethyl)phenyl |
| 31 | 0 | Cl | H | Cl | H | 4-(2-thiophenylsulfonamidylethyl)phenyl |
| 32 | 0 | Cl | H | Cl | H | 4-(ethansulfonamidylethyl)phenyl |
| 33 | 0 | H | H | F | H | 4-(methanesulfonarnidylethyl)phenyl |
| 34 | 0 | H | H | F | H | 4-(p-toluenesulfonamidylethyl)phenyl |
| 35 | 0 | H | H | F | H | 4-(ethansulfonamidylethyl)phenyl |
| 36 | 0 | H | H | F | H | 4-morpholinophenyl |
| 37 | 0 | F | H | F | H | 4-(methanesulfonamidylethyl)phenyl |
| 38 | 0 | F | H | F | H | 4-(p-toluenesulfonamidylethyl)phenyl |
| 39 | 0 | F | H | F | H | 4-(ethansulfonamidylethyl)phenyl |
| 40 | 0 | Cl | H | F | H | 4-(p-toluenesulfonamidylethyl)phenyl |
| 41 | 0 | Cl | H | F | H | 4-(methanesulfonamidylethyl)phenyl |
| 42 | 0 | Cl | H | F | H | 4-(ethansulfonamidylethyl)phenyl |
| 43 | 0 | H | Cl | F | H | 4-(p-toluenesulfonamidylethyl)phenyl |
| 44 | 0 | H | Cl | F | H | 4-(ethansulfonamidylethyl)phenyl |
| 45 | 0 | H | Cl | F | H | 4-(methanesulfonamidylethyl)phenyl |
| 46 | 0 | H | H | H | | $R^4$, $R^5$ = piperidinyl |
| 47 | 0 | H | H | Cl | | $R^4$, $R^5$ = piperidinyl |
| 48 | 0 | Cl | H | Cl | | $R^4$, $R^5$ = piperidinyl |
| 49 | 1 | H | H | H | H | 4-nitrophenyl |
| 50 | 1 | H | H | H | H | 4-aminophenyl |
| 51 | 1 | H | H | H | H | phenyl |
| 52 | 1 | H | H | Cl | H | phenyl |
| 53 | 1 | H | H | Cl | H | 4-nitrophenyl |
| 54 | 1 | H | H | Cl | H | 4-aminophenyl |
| 55 | 1 | Cl | H | Cl | H | phenyl |
| 56 | 1 | Cl | H | Cl | H | 4-nitrophenyl |
| 57 | 2 | H | H | H | H | phenyl |
| 58 | 2 | H | H | H | H | 4-hydroxyphenyl |
| 59 | 2 | H | H | H | H | 4-nitrophenyl |
| 60 | 2 | H | H | H | H | 4-aminophenyl |
| 61 | 2 | H | H | H | H | amino |
| 62 | 2 | H | H | H | H | 4-hydroxy-3-methoxyphenyl |
| 63 | 2 | H | H | H | H | 3-hydroxy-4-methoxyphenyl |
| 64 | 2 | H | H | H | H | 4-(methanesulfonamidyl)phenyl |
| 65 | 2 | H | H | H | H | 4-(p-toluenesulfonamidyl)phenyl |
| 66 | 2 | H | H | H | H | 4-morpholinyl |
| 67 | 2 | H | H | H | H | 4-phthlimidophenyl |
| 68 | 2 | H | H | H | H | 4-(ethanesulfonamidyl)phenyl |
| 69 | 2 | H | H | H | H | 4-nitro-2-pyridinylamino |
| 70 | 2 | H | H | H | H | 2-pyridyl |
| 71 | 2 | H | H | Cl | H | phenyl |
| 72 | 2 | H | H | Cl | H | 4-nitrophenyl |
| 73 | 2 | H | H | Cl | H | 4-aminophenyl |
| 74 | 2 | H | H | Cl | H | 4-hydroxyphenyl |
| 75 | 2 | H | H | Cl | H | 4-(methanesulfonamidyl)phenyl |
| 76 | 2 | H | H | Cl | H | 4-(p-toluenesulfonamidyu)phenyl |

TABLE 1-continued

| Com No. | n | R¹ | R² | R³ | R⁴ | R⁵ |
|---|---|---|---|---|---|---|
| 77 | 2 | H | H | Cl | H | 3-hydroxy-4-methoxyphenyl |
| 78 | 2 | H | H | Cl | H | N-morpholinyl |
| 79 | 2 | H | H | Cl | H | 4-phthalimidophenyl |
| 80 | 2 | H | H | Cl | H | 4-(ethanesulfonamidyl)phenyl |
| 81 | 2 | H | H | Cl | H | 4-nitro-2-pyridinylamino |
| 82 | 2 | H | H | Cl | H | 2-pyridyl |
| 83 | 2 | H | H | Cl | H | 4-imidazolyl |
| 84 | 2 | H | H | Cl | H | 4-hydroxyphenyl |
| 85 | 2 | H | H | Cl | H | 4-acetylamino-2-pyridylamino |
| 86 | 2 | H | H | Cl | H | 4-(4-methylpiperazin-1-yl-acetylamino)phenyl |
| 87 | 2 | H | H | Cl | H | 4-(4-ethylpiperazin-1-yl-acetylamino)phenyl |
| 88 | 2 | H | H | Cl | H | 4-(dimethylaminoacetylamino)phenyl |
| 89 | 2 | H | H | Cl | H | 4-(diethylaminoacetylamino)phenyl |
| 90 | 2 | H | H | Cl | H | 4-aminophenyl |
| 91 | 2 | H | H | Cl | H | 4-amino-2-pyridylamino |
| 92 | 2 | H | H | Cl | H | 4-(morpholin-4-yl-acetylamino)phenyl |
| 93 | 2 | H | H | Cl | H | 4-(N,N-dimethylamino)phenyl |
| 94 | 2 | H | H | Cl | H | 4-(morpholin-4-yl-ethoxy)phenyl |
| 95 | 2 | H | H | Cl | H | 4-(4-methylpiperazin-1-yl-ethoxy)phenyl |
| 96 | 2 | H | H | Cl | H | 2-hydroxyphenyl |
| 97 | 2 | H | H | Cl | H | 2-methoxyphenyl |
| 98 | 2 | H | H | Cl | H | 3-bromophenyl |
| 99 | 2 | Cl | H | Cl | H | phenyl |
| 100 | 2 | Cl | H | Cl | H | 4-nitrophenyl |
| 101 | 2 | Cl | H | Cl | H | 4-hydroxy-3-methoxyphenyl |
| 102 | 2 | Cl | H | Cl | H | 3-hydroxy-4-methoxyphenyl |
| 103 | 2 | Cl | H | Cl | H | amino |
| 104 | 2 | Cl | H | Cl | H | 4-hydroxyphenyl |
| 105 | 2 | Cl | H | Cl | H | 4-(p-toluenesulfonamidyl)phenyl |
| 106 | 2 | Cl | H | Cl | H | 4-(methanesulfonamidyl)phenyl |
| 107 | 2 | Cl | H | Cl | H | 4-phthlimidophenyl |
| 108 | 2 | Cl | H | Cl | H | 4-morpholinyl |
| 109 | 2 | Cl | H | Cl | H | 4-(ethanesulfonamidyl)phenyl |
| 110 | 2 | Cl | H | Cl | H | 4-nitro-2-pyridinylamino |
| 111 | 2 | Cl | H | Cl | H | 2-pyridyl |
| 112 | 2 | Cl | H | Cl | H | 4-(acetylanino)phenyl |
| 113 | 2 | Cl | H | Cl | H | 4-(pentanoylamino)phenyl |
| 114 | 2 | H | H | F | H | 4-(methanesulfonamidyl)phenyl |
| 115 | 2 | H | H | F | H | 4-(p-toluenesulfonamidyl)phenyl |
| 116 | 2 | H | H | F | H | 4-(ethanesulfonamidyl)phenyl |
| 117 | 2 | H | H | F | H | 4-(acetylamino)phenyl |
| 118 | 2 | H | H | F | H | 4-methylpiperazin-1-yl |
| 119 | 2 | H | H | F | H | 4-morpholin-1-yl |
| 120 | 2 | H | H | F | H | 4-(pentanoylamino)phenyl |
| 121 | 2 | H | H | F | H | 4-hydroxyphenyl |
| 122 | 2 | H | H | F | H | 4-nitro-2-pyridinylamino |
| 123 | 2 | H | H | F | H | 4-(methanesulfonylamino-2-pyridyl)amino |
| 124 | 2 | H | H | F | H | 4-(p-toluenesulfonylamino-2-pyridyl)-amino |
| 125 | 2 | H | H | F | H | 4-imidazolyl |
| 126 | 2 | H | H | F | H | 4-acetylamino-2-pyridylamino |
| 127 | 2 | H | H | F | H | 4-(4-methylpiperazin-1-yl-acetylamino)phenyl |
| 128 | 2 | H | H | F | H | 4-(4-ethylpiperazin-1-yl-acetylamino)-phenyl |
| 129 | 2 | H | H | F | H | 4-(dimethylaminoacetylamino)phenyl |
| 130 | 2 | H | H | F | H | 4-(diethylaminoacetylamino)phenyl |
| 131 | 2 | H | H | F | H | 4-aminophenyl |
| 132 | 2 | H | H | F | H | 4-morpholmophenyl |
| 133 | 2 | H | H | F | H | 4-(3-dimethylaminopyrrolidin-1-yl)phenyl |
| 134 | 2 | H | H | F | H | 4-(morpholin-4-yl-acetylamino)phenyl |
| 135 | 2 | H | H | F | H | 4-(N,N-dimethylamino)phenyl |
| 136 | 2 | H | H | F | H | 4-(morpholin-4-yl-ethoxy)phenyl |
| 137 | 2 | H | H | F | H | 2-hydroxyphenyl |
| 138 | 2 | H | H | F | H | 2-methoxyphenyl |
| 139 | 2 | H | H | F | H | 3-bromophenyl |
| 140 | 2 | F | H | F | H | 4-(methanesulfonamidyl)phenyl |
| 141 | 2 | F | H | F | H | 4-(p-toluenesulfonamidyl)phenyl |
| 142 | 2 | F | H | F | H | 4-(ethanesulfonamidyl)phenyl |
| 143 | 2 | Cl | H | F | H | 4-(methanesulfonamidyl)phenyl |
| 144 | 2 | Cl | H | F | H | 4-(p-toluenesulfonamidyl)phenyl |
| 145 | 2 | Cl | H | F | H | 4-(ethanesulfonamidyl)phenyl |
| 146 | 2 | Cl | H | F | H | 4-(acetylamino)phenyl |
| 147 | 2 | Cl | H | F | H | 4-morpholin-1-yl |
| 148 | 2 | Cl | H | F | H | 4-methylpiperazin-1-yl |
| 149 | 2 | Cl | H | F | H | 4-(pentanoylamino)phenyl |
| 150 | 2 | Cl | H | F | H | 4-hydroxyphenyl |
| 151 | 2 | Cl | H | F | H | 4-nitro-2-pyridinylamino |
| 152 | 2 | Cl | H | F | H | 4-(methanesulfonylamino-2-pyridyl)amino |
| 153 | 2 | Cl | H | F | H | 4-(p-toluenesulfonylamino-2-pyridyl)-amino |
| 154 | 2 | Cl | H | F | H | 4-imidazolyl |
| 155 | 2 | Cl | H | F | H | 4-acetylamino-2-pyridylamino |
| 156 | 2 | Cl | H | F | H | 4-(4-methylpiperazin-1-yl-acetylamino)phenyl |
| 157 | 2 | Cl | H | F | H | 4-(4-ethylpiperazin-1-yl-acetylamino)phenyl |
| 158 | 2 | Cl | H | F | H | 4-(dimethylaminoacetylamino)phenyl |
| 159 | 2 | Cl | H | F | H | 4-(diethylaminoacetylamino)phenyl |
| 160 | 2 | H | Cl | F | H | 4-(p-toluenesulfonamidyl)phenyl |
| 161 | 2 | H | Cl | F | H | 4-(methanesulfonamidyl)phenyl |
| 162 | 3 | H | H | H | H | methyl |
| 163 | 3 | H | H | H | H | amino |
| 164 | 3 | H | H | H | H | 2-oxopyrrolidin-1-yl |
| 165 | 3 | H | H | H | H | 1-imidazolyl |
| 166 | 3 | H | H | H | H | 4-N-morpholmyl |
| 167 | 3 | H | H | H | H | 2-methylimidazol-1-yl |
| 168 | 3 | H | H | Cl | H | methyl |
| 169 | 3 | H | H | Cl | H | 2-oxopyrrolidin-1-yl |
| 170 | 3 | H | H | Cl | H | 1-imidazolyl |
| 171 | 3 | H | H | Cl | H | 4-morpholinyl |
| 172 | 3 | H | H | Cl | H | 2-phenylimidazol-1-yl |
| 173 | 3 | H | H | Cl | H | 4-methylimidazol-1-yl |
| 174 | 3 | H | H | Cl | H | 4,5-dichloroimidazo-1-yl |
| 175 | 3 | H | H | Cl | H | 2-methylimidazol-1-yl |
| 176 | 3 | Cl | H | Cl | H | methyl |
| 177 | 3 | Cl | H | Cl | H | 2-oxopyrrolidin-1-yl |
| 178 | 3 | Cl | H | Cl | H | 1-imidazolyl |
| 179 | 3 | Cl | H | Cl | H | 4-morpholin-yl |
| 180 | 3 | Cl | H | Cl | H | 2-phenylimidazol-1-yl |
| 181 | 3 | Cl | H | Cl | H | 4-methylimidazol-1-yl |
| 182 | 3 | Cl | H | Cl | H | 4,5-dichloroimidazol-1-yl |
| 183 | 3 | Cl | H | Cl | H | 2-methylimidazol-1-yl |
| 184 | 3 | Cl | H | Cl | H | 2-isopropylimidazol-1-yl |
| 185 | 3 | H | H | F | H | 1-imidazolyl |
| 186 | 3 | H | H | F | H | 2-isopropylimidazol-1-yl |
| 187 | 3 | H | H | F | H | 4-methylimidazol-1-yl |
| 188 | 3 | H | H | F | H | 2-methylimidazol-1-yl |
| 189 | 3 | H | H | F | H | 2-ethylimidazol-1-yl |
| 190 | 3 | H | H | F | H | 4,5-dichloroimidazol-1-yl |
| 191 | 3 | F | H | F | H | 2-isopropylimidazol-1-yl |
| 192 | 3 | F | H | F | H | 1-imidazolyl |
| 193 | 3 | F | H | F | H | 4-methylimidazol-1-yl |
| 194 | 3 | F | H | F | H | 4,5-dichloroimidazol-1-yl |
| 195 | 3 | F | H | F | H | 2-methylimidazol-1-yl |
| 196 | 3 | F | H | F | H | 2-ethylimidazol-1-yl |
| 197 | 3 | F | H | F | H | 4,5-dichioroimidazol-1-yl |
| 198 | 3 | Cl | H | F | H | 1-imidazolyl |
| 199 | 3 | Cl | H | F | H | 4-methylimidazol-1-yl |
| 200 | 3 | Cl | H | F | H | 4,5-dichloroimidazol- 1-yl |
| 201 | 3 | Cl | H | F | H | 2-methylimidazol- 1-yl |
| 202 | 3 | H | Cl | F | H | 4-methylimidazol-1-yl |
| 203 | 3 | H | Cl | F | H | 1-imidazolyl |
| 204 | 3 | R¹, R² and R⁴ = H R³ = morpholin-1-yl-ethylamino | | | | 4,5-dichloroimidazol-1-yl |

The inventive compound (except for the compound wherein R³ is morpholin-1-yl-ethylamino) of formula (Ia) may be prepared as in Scheme 1.

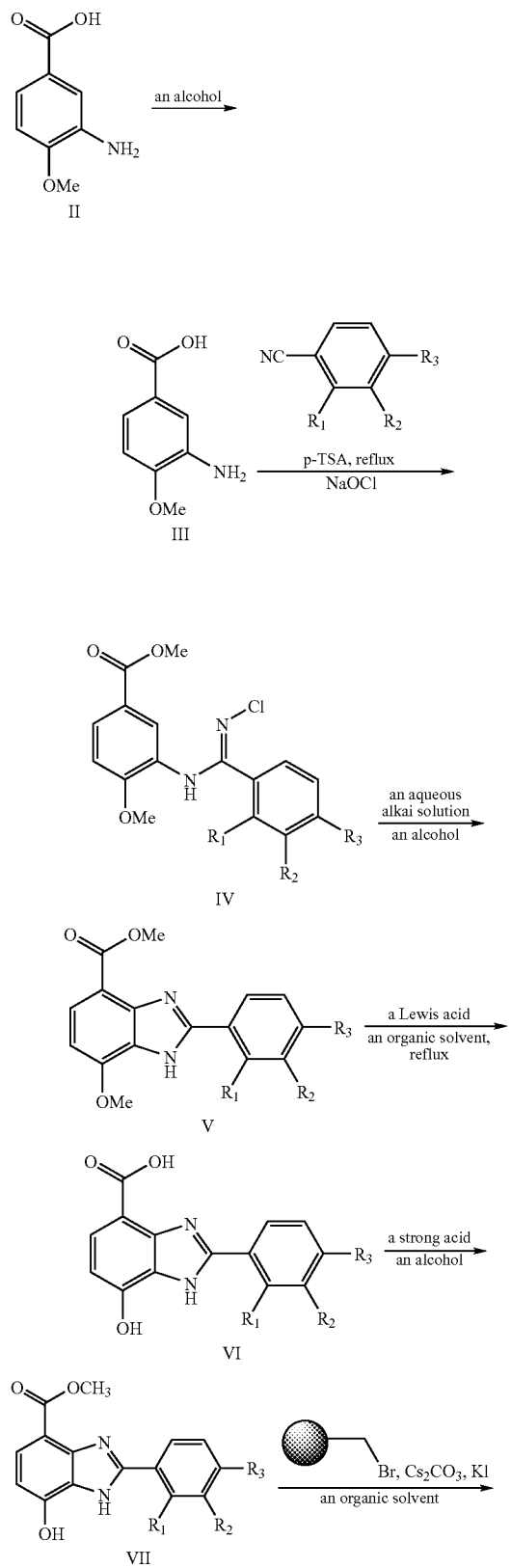
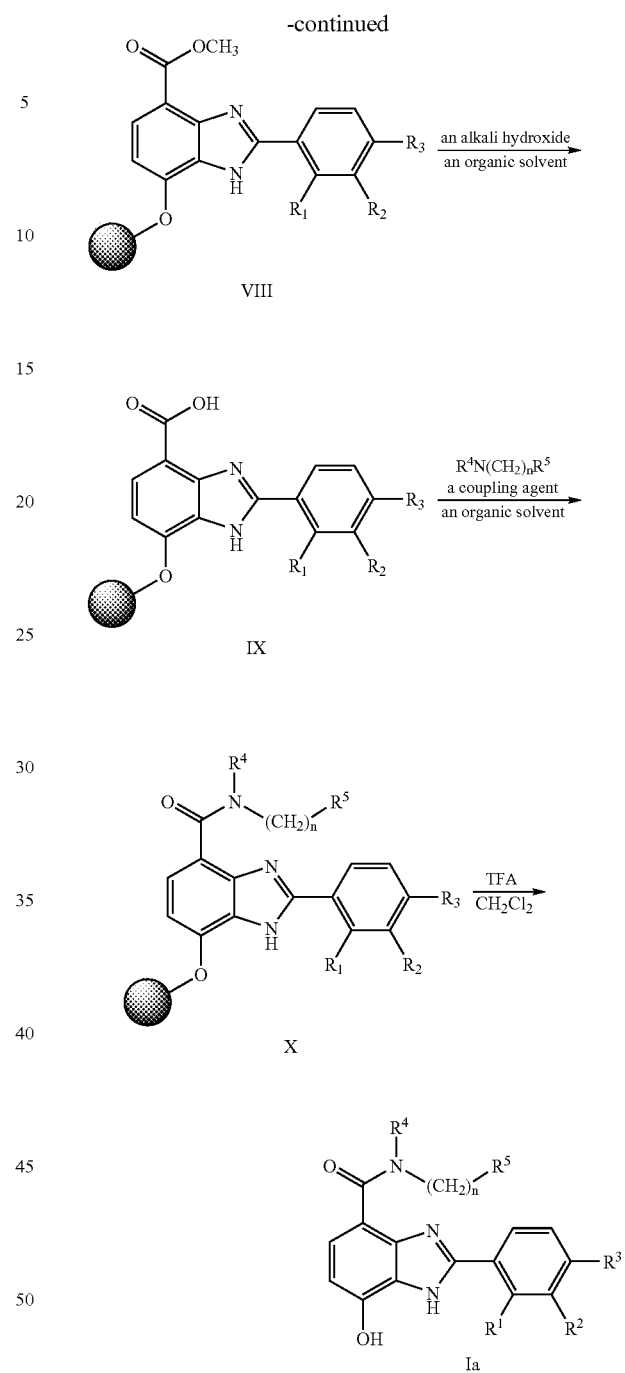

wherein, p-TSA is p-toluenesulfonic acid, DMF is dimethylformamide, THF is tetrahydrofuran, TFA is trifluoroacetic acid, EDCI is ethyl-dimethylaminopropyl-carbodiimide hyrochloride, DMAP is 4-dimethylamineprydine, HOBt is N-hydroxybenzotriazole, n, $R^1$, $R^2$, $R^3$, $R^4$ and $R^5$ have the same meanings as defined previously.

As shown in Scheme I, the compound of formula (Ia) can be prepared by reacting 3-amino-4-methoxy benzoic acid (compound II) and an alcohol (e.g., methanol or ethanol) to obtain compound (III); adding anhydrous p-toluenesulfonic acid and benzonitrile to the compound (III) thus obtained, refluxing the mixture at 80 to 200° C., adding NaOCl thereto at room temperature and purifying by silica gel column chromatography to obtain compound (IV); dissolving the compound (IV) thus obtained in an alcohol (e.g., methanol or ethanol), adding an aqueous alkali solution ($Na_2CO_3$, $NaHCO_3$, $K_2CO_2$ or $KHCO_3$ solution) thereto and refluxing the mixture to obtain compound (V); dissolving the compound (V) thus obtained in an organic solvent, e.g., toluene, adding a Lewis acid (e.g., $AlCl_3$ or $BBr_3$) thereto and refluxing the mixture to obtain compound (VI); dissolving the compound (V) thus obtained in an alcohol, adding a strong acid, nitric acid or sulfuric acid, thereto at room temperature and refluxing the mixture to obtain compound (VII); dissolving the compound (VII) thus obtained and (4-bromomethylphenoxy)-methyl polystyrene Wang resin in an organic solvent, e.g., DMF, THF or chloroform, adding a base ($CsCO_3$, $Na_2CO_3$, $NaHCO_3$, $K_2CO_3$ or $KHCO_3$) and KI thereto (1:3:3:3) and stirring the mixture at 50 to 60° C. for 1 to 24 hours to obtain compound (VIII); dissolving the compound (VIII) thus obtained in an organic solvent, adding an alcohol solution of an alkali hydroxide (e.g., LiOH, NaOH or KOH) thereto and refluxing the mixture to obtain compound (IX); dissolving the compound (IX) thus obtained in an organic solvent, adding $R^4N(CH_2)_nR^5$ and a coupling agent (e.g., EDCI/DMAP/HOBt, DCC or pyBop) thereto and stirring the mixture at room temperature to obtain compound (X); and dissolving the compound (X) thus obtained in $CH_2Cl_2$, adding trifluoroacetic acid thereto and stirring the mixture at room temperature to obtain compound (Ia).

The inventive compound (wherein $R^3$ is morpholin-1-yl-ethylamino) represented to formula (Ib) may be prepared, as in Scheme II.

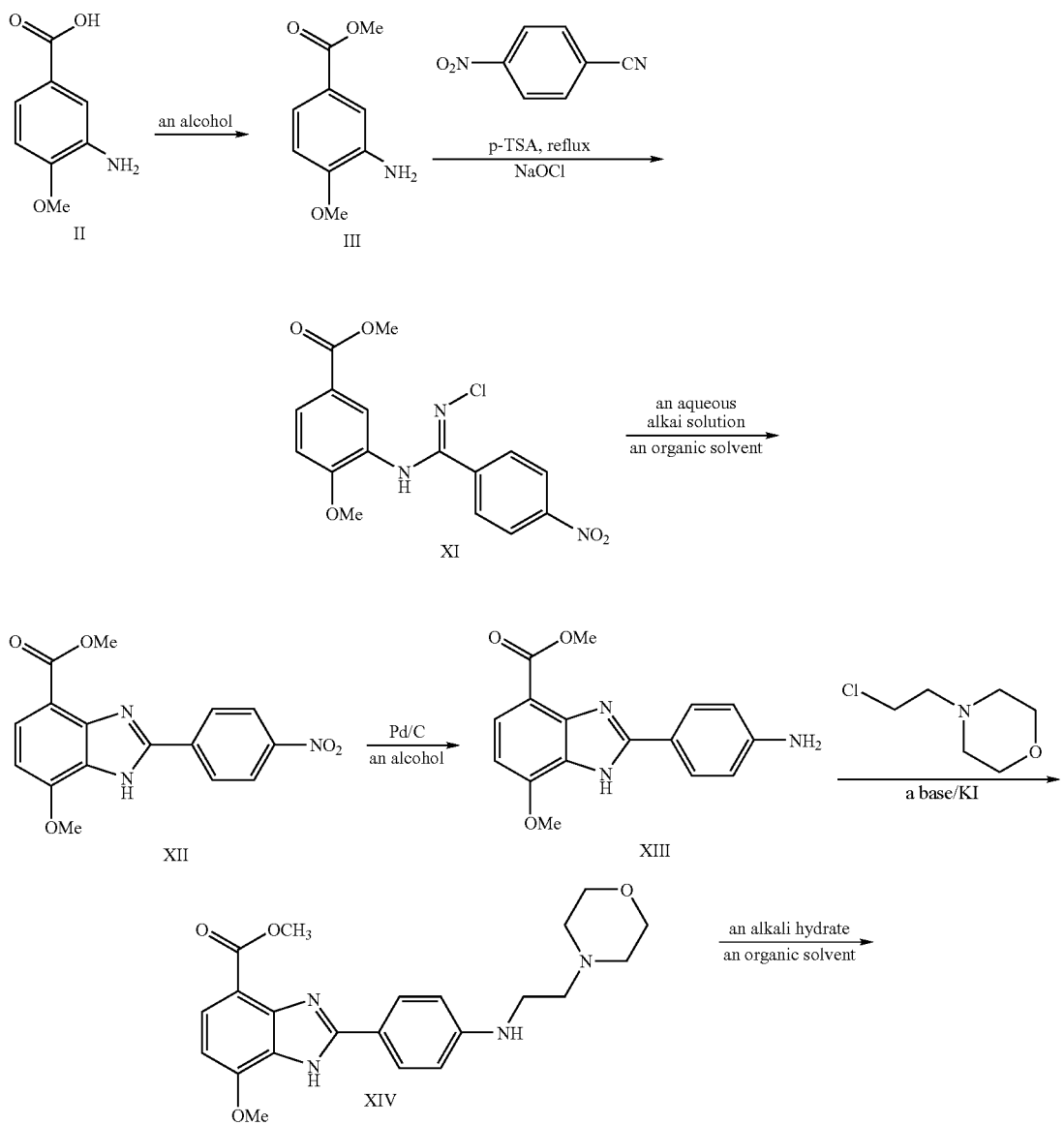

Scheme II

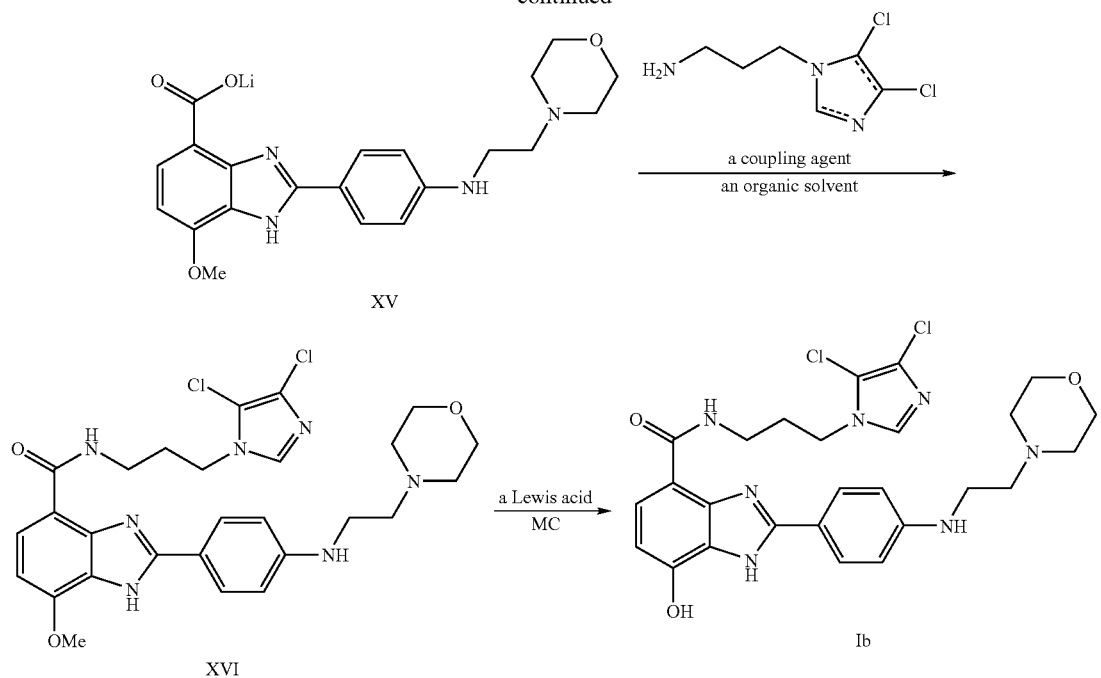

As shown in Scheme II, the compound of formula (Ib) can be prepared by reacting 3-amino-4-methoxy benzoic acid (compound II) and an alcohol (e.g., methanol or ethanol) to obtain compound (III), adding p-toluenesulfonic acid, benzene and 4-nitrobenzonitrile thereto, refluxing the mixture at 80 to 200° C., adding NaOCl thereto at room temperature and purifying by silica gel column chromatography to obtain compound (XI); dissolving the compound (XI) thus obtained in an organic solvent, adding an aqueous alkali solution (e.g., Na2CO3 solution) thereto, refluxing the mixture and purifying by silica gel column chromatography to obtain compound (XII); dissolving the compound (XII) thus obtained in an alcohol, adding Pd/C thereto and refluxing the mixture to obtain compound (XIII); dissolving the compound (XIII) thus obtained in an organic solvent, adding a base (e.g., CsCO3, Na2CO3, NaHCO3, K2CO3 or KHCO3), 2-chloroethylmorphine and potassium iodide thereto and stirring the mixture at room temperature to obtain compound (XIV); dissolving the compound (XIV) obtained thus in an organic solvent, adding an alkali hydrate, stirring the mixture at room temperature to obtain compound (XV); dissolving the compound (XV) thus obtained in an organic solvent, adding 4,5-dichloro-1-(3-aminoprophyl) imidazole and a coupling agent (e.g., EDCI, DMAP or HOBt), stirring the mixture at room temperature and purifying by silica gel column chromatography to obtain compound (XVI); and dissolving the compound (XVI) thus obtained in MC, adding a Lewis acid thereto, stirring the mixture, concentrating the resulting solution under a reduced pressure and purifying by silica gel column chromatography to obtain compound (Ib).

A salt, hydrate, solvate and isomer of the inventive compound of formula (I) may be prepared by employing any of the known methods. The inventive compound of formula (I), a salt, hydrate, solvate or isomer thereof may used for the treatment of GSK-3β-dependent diseases including fatness, diabetes and dementia, by way of inhibiting GSK-3β activity, the inventive compound having an $IC_{50}$ value in the range of 1 to 10,000 nM.

Accordingly, the present invention includes a pharmaceutical composition which comprises a therapeutically effective amount of the compound of formula (I), a salt, hydrate, solvate or isomer thereof as an active ingredient and a pharmaceutically acceptable carrier; therefore, the pharmaceutical composition of the present invention exerts superior preventive and treating effects on GSK-β-dependent diseases such as fatness, diabetes and dementia and the like.

A pharmaceutical formulation may be prepared in accordance with any of the conventional procedures. In preparing the formulation, the active ingredient is preferably admixed or diluted with a carrier, or enclosed within a carrier, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular introduction. In case of human, a typical daily dose of the compound of formula (I) may range from about 0.01 to 100 mg/kg body weight, preferably 0.1 to 50 mg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

The following examples are intended to further illustrate the present invention without limiting its scope.

PREPARATION EXAMPLE 1

Preparation of Wang Resin (p-benzyloxybenzyl Alcohol Resin)-supported 7-hydroxy-2-phenyl-1H-benzoimidazole-4-carboxylic acid ($R^1$=H, $R^2$=H and $R^3$=H)

(1) Preparation of 3-amino-4-methoxy benzoic acid methyl ester 3-amino-4-methoxy benzoic acid (40 g, 0.239 mol) was dissolved in methanol, $H_2SO_4$ (38.14 ml, 0.717 mol) was added dropwise thereto and refluxed for 12 hours. The resulting mixture was cooled to room temperature and concentrated under a reduced pressure to remove methanol, neutralized with $NaHCO_3$, extracted with ethyl acetate, and the extract was concentrated under a reduced pressure. The resulting residue was purified by recrystallization from ethyl acetate/hexane to obtain the title compound (39 g, 0.215 mol) in a yield of 90%.

$^1$H NMR (CDCl$_3$): δ 7.87–7.78 (2H, m), 7.22 (1H, d), 3.93 (3H, s), 3.82 (3H, s)

MW: 181

(2) Preparation of 4-methoxy-3-[(N-chloro-benzimidoyl)-amino]-benzoic acid methyl ester Anhydrous p-toluene sulfonic acid (41.99 g, 220.8 mmol) was melted at 120° C. and 3-amino-4-methoxy benzoic acid methyl ester (20 g, 110.38 mmol) obtained in step 1 and benzonitrile (22.77 g, 220.8 mmol) were added thereto and stirred at 180° C. for 5 hours. The resulting solution was cooled to room temperature and the reaction was stopped by adding $NaHCO_3$ thereto. The resulting mixture was extracted with ethyl acetate, the extract was dried over $MgSO_4$ and concentrated under a reduced pressure. The concentrate was dissolved in 50% methanol and 5% NaOCl (56 Ml, 37.65 mmol) was added dropwise thereto. After 5 min, the resulting mixture was extracted with ethyl acetate, the extract was dried over $MgSO_4$ and concentrated under a reduced pressure. The resulting residue was purified by silica gel column chromatography (eluent—MeOH/CDCl$_3$=5:95, Merck, Silicagel 60) to obtain the title compound (31 g, 25.10 mmol) in a yield of 88%;

$^1$H NMR (CDCl$_3$): δ 7.78 (1H, d), 7.48(1H, s), 7.37–7.24 (5H, m), 6.95 (1H, d), 3.78 (6H, s)

MW: 318

(3) Preparation of 7-methoxy-2-phenyl-1H-benzoimidazole-4-carboxylic acid methyl ester 4-methoxy-3-[(N-chloro-benzimidoyl)-amino]-benzoic acid methyl ester (8 g, 25.10 mmol) obtained in step 1 was dissolved in 50 ml of 50% methanol and $NaHCO_3$ (5.32 g, 50.20 mmol) was added dropwise thereto at room temperature and refluxed for 5 min. The resulting solution was cooled to room temperature, extracted with ethyl acetate, and the extract was concentrated under a reduced pressure. The resulting residue was purified by recrystallization from ethyl acetate/hexane to obtain the title compound (6 g, 15.94 mmol) in a yield of 86%.

$^1$H NMR (CDCl$_3$): δ 10.65 (1H, br), 8.23 (2H, d), 7.49 (3H, m), 6.75 (1H, d), 4.13 (3H, s), 3.99 (3H, s)

MW: 282

(4) Preparation of 7-hydroxy-2-phenyl-1H-benzoimidazole-4-carboxylic acid 7-methoxy-2-phenyl-1H-benzoimidazole-4-carboxylic acid methyl ester (4.5 g, 15.94 mmol) obtained in step 3 was dissolved in 100 ml of toluene, aluminum chloride (9.56 g, 71.73 mmol) was added thereto and refluxed for 8 hours. The resulting solution was cooled to room temperature, the reaction was stopped by adding 3 N HCl thereto and stirred for 30 min. The precipitate formed was filtered, washed with benzene and dried to obtain the title compound (3.5 g, 13.77 mmol) in a yield of 86%.

$^1$H NMR (DMSO-d$_6$): δ 8.29 (2H; d), 7.68 (1H, d), 7.56–7.49 (3H, m), 6.67 (1H, d)

MW: 254

(5) Preparation of 7-hydroxy-2-phenyl-1H-benzoimidazole-4-carboxylic acid methyl ester 7-methoxy-2-phenyl-1H-benzoimidazole-4-carboxylic acid (2.00 g, 7.46 mmol) obtained in step 4 was dissolved in 30 ml of methanol, $H_2SO_4$ (2.00 ml, 37.28 mmol) was added dropwise thereto and refluxed for 15 hours. The resulting solution was cooled to room temperature, concentrated under a reduced pressure to remove methanol, and the residue was neutralized with $NaHCO_3$. Then, the neutralized residue was extracted with ethyl acetate and concentrated under a reduced pressure to obtain a residue which purified by recrystallization from CHCl$_3$/MeOH/hexane to obtain the title compound (1.7 g, 5.89 mmol) in a yield of 83%.

$^1$H NMR (CH$_3$OH-d$_4$): δ 7.82 (1H, d), 7.42–7.25 (5H, m), 6.64 (1H, d), 4.92 (3H, s)

MW: 268

(6) Preparation of Wang resin (p-benzyloxybenzyl alcohol resin)-supported 7-hydroxy-2-phenyl-1H-benzoimidazole-4-carboxylic acid methyl ester p-nitrophenyl carbonate Wang resin (476 mg, 0.67 mmol) was dissolved in DMF, and 7-hydroxy-2-phenyl-1H-benzoimidazole-4-carboxylic acid methyl ester (567 mg, 2.01 mmol) obtained in step 5, Cs$_2$CO$_3$ (655 mg, 2.01 mmol) and KI (334 mg, 2.01 mmol) were added thereto to be stirred at 50 to 60° C. for 12 hours. The resulting solution was cooled to room temperature and filtered. The filtrate was washed with DMF, MeOH and CH$_2$Cl$_2$ and dried to obtain the title compound (608 mg, 0.65 mmol) in a yield of 98%.

(7) Preparation of Wang resin-supported 7-hydroxy-2-phenyl-1H-benzoimidazole-4-carboxylic acid methyl ester Wang resin-supported 7-hydroxy-2-phenyl-1H-benzoimidazole-4-carboxylic acid methyl ester (570 mg, 0.47 mmol) obtained in step 6 was dissolved in THF, LiOH.H$_2$O (99 mg, 2.35 mmol) in MeOH—H$_2$O (2:1) was added thereto and refluxed for 5 hours. The resulting solution was cooled to room temperature and filtered. The filtrate was washed with MeOH and CH$_2$Cl$_2$, and dried to obtain the title compound (551 mg, 0.42 mmol) in a yield of 90%.

PREPARATION EXAMPLE 2

Preparation of 2-(4-chloro-phenyl)-7-hydroxy-1H-benzoimidazole-4-carboxylic acid ($R^1$=H, $R^2$=H and $R^3$=Cl)

(1) Preparation of 3-[(4-chloro-N-chloro-benzimidoyl)-amino]-4-methoxy-benzoic acid methyl ester Anhydrous p-toluene sulfonic acid (41.99 g, 220.76 mmol) was melted at 120° C. and 3-amino-4-methoxy benzoic acid methyl ester (20 g, 110.38 mmol) obtained in step 1 of Preparation Example 1 and 4-chlorobenzonitrile (22.78 g, 165.57 mol) were added thereto and stirred at 160° C. for 8 hours. The resulting solution was cooled to room temperature and the reaction was stopped by adding 1M NaHCO$_3$ thereto. The resulting mixture was extracted with ethyl acetate, the extract was dried over MgSO$_4$ and concentrated under a reduced pressure. The concentrate was dissolved in 500 ml of 50% methanol and 5% NaOCl (197 Ml, 132.46 mmol) was added dropwise thereto. After 5 min, the resulting mixture was extracted with ethyl acetate, the extract was dried over MgSO$_4$ and concentrated under a reduced pressure. The resulting residue was purified by silica gel column chlomatography (eluent—MeOH:CDCl3=5/95, Merck, Silicagel 60) to obtain the title compound (19.43 g, 55.19 mmol) in a yield of 50%.

$^1$H NMR (CH$_3$OH-d$_4$): δ 7.62 (2H, m), 7.22–7.15 (4H, m), 6.59 (1H, s), 4.00–3.80 (6H, d)

MW: 352

(2) Preparation of 2-(4-chloro-phenyl)-7-methoxy-1H-benzoimidazole-4-carboxylic acid methyl ester 3-[(4-chloro-N-chloro-benzimidoyl)-amino]-4-methoxy-benzoic acid methyl ester (5.5 g, 15.63 mmol) obtained in step 1 was dissolved in 40 ml of 50% methanol and Na$_2$CO$_3$ (3.53 g, 33.26 mmol) was added dropwise thereto at room temperature and refluxed for 5 min. The resulting solution was cooled to room temperature, extracted with ethyl acetate, the extract was concentrated under a reduced pressure. The resulting residue was purified by silica gel column chromatography to obtain the title compound (2.57 g, 8.13 mmol) in a yield of 52%.

$^1$H NMR (CDCl$_3$): δ 8.15 (2H, d), 7.95 (1H, d), 7.51 (2H, m), 6.75 (1H, d), 4.06 (3H, s)

MW: 316

(3) Preparation of 2-(4-chloro-phenyl)-7-hydroxy-1H-benzoimidazole-4-carboxylic acid 2-(4-chloro-phenyl)-7-methoxy-1H-benzoimidazole-4-carboxylic acid methyl ester (1.0 g, 3.16 mmol) obtained in step 2 was dissolved in 10 ml of toluene, aluminum chloride (2.11 g, 15.8 mmol) was added thereto and refluxed for 8 hours. The resulting solution was cooled to room temperature, the reaction was stopped by adding 3 N HCl thereto and stirred for 30 min. The precipitate formed was filtered, washed with benzene and dried to obtain the title compound (745 mg, 2.59 mmol) in a yield of 82%.

$^1$H NMR (CH$_3$OH-d$_4$): δ 8.06 (3H, m), 7.50 (2H, m), 6.97 (1H, d)

MW: 288

(4) Preparation of 2-(4-chloro-phenyl)-7-hydroxy-1H-benzoimidazole-4-carboxylic acid methyl ester 2-(4-chloro-phenyl)-7-hydroxy-1H-benzoimidazole-4-carboxylic acid (200 mg, 0.69 mmol) obtained in step 3 was dissolved in 5 ml of methanol, H$_2$SO$_4$ (0.18 ml, 3.45 mmol) was added dropwise thereto and refluxed for 15 hours. The resulting solution was cooled to room temperature, concentrated under a reduced pressure to remove methanol, and the residue was neutralized with 1M NaHCO$_3$. Then, the neutralized residue was extracted with ethyl acetate and concentrated under a reduced pressure to obtain a residue which was purified by silica gel column chromatography (eluent—MeOH/CDCl$_3$=5/95, Merck, Silicagel 60) to obtain the title compound (166 mg, 0.55 mmol) in a yield of 80%.

$^1$H NMR (CH$_3$OH-d$_4$): δ 10.75 (1H, Br), 7.89 (3H, m), 7.46 (2H, d), 6.82 (1H, d), 3.39 (3H, s)

MW: 302

(5) Preparation of Wang Resin-Supported 2-(4-chloro-phenyl)-7-hydroxy-1H-benzoimidazole-4-carboxylic acid methyl ester (4-bromomethylphenoxy)-methyl polystyrene Wang resin (476 mg, 0.67 mmol) was dissolved in 5 ml of DMF, and 2-(4-chloro-phenyl)-7-hydroxy-1H-benzoimidazole-4-carboxylic acid methyl ester (567 mg, 2.01 mmol) obtained in step 4, Cs$_2$CO$_3$ (655 mg, 2.01 mmol) and KI (334 mg, 2.01 mmol) were added thereto to be stirred at 50 to 60° C. for 12 hours. The resulting solution was cooled to room temperature and filtered. The filtrate was washed with DMF, MeOH and CH$_2$Cl$_2$ and dried to obtain the title compound (608 mg, 0.65 mmol) in a yield of 98%.

(6) Preparation of Wang resin-supported 2-(4-chloro-phenyl)-7-hydroxy-1H-benzoimidazole-4-carboxylic acid Wang resin-supported 2-(4-chloro-phenyl)-7-hydroxy-1H-benzoimidazole-4-carboxylic acid methyl ester (570 mg, 0.47 mmol) obtained in step 5 was dissolved in THF, LiOH.H$_2$O (99 mg, 2.35 mmol) in MeOH—H$_2$O (1:1) was added thereto and the resulting mixture was refluxed for 5 hours. The resulting solution was cooled to room temperature and filtered. The filtrate was washed with MeOH and CH$_2$Cl$_2$, and dried to obtain the title compound (551 mg, 0.42 mmol) in a yield of 90%.

PREPARATION EXAMPLE 3

Preparation of 2-(2,4-dichloro-phenyl)-7-hydroxy-1H-benzoimidazole-4-carboxylic acid ($R^1$=Cl, $R^2$=H and $R^3$=Cl)

(1) Preparation of 3-[(2,4-dichloro-N-chloro-benzimidoyl)-amino]-4-methoxy-benzoic acid methyl ester Anhydrous p-toluene sulfonic acid (20.99 g, 110.04 mmol) was melted at 120° C. and 3-amino-4-methoxy benzoic acid methyl ester (10 g, 55.20 mmol) obtained in step 1 of Preparation Example 1 and 2,4-dichlorobenzonitrile (18.99 g, 110.04 mol) were added thereto and stirred at 180° C. for 6 hours. The resulting solution was cooled to room temperature and the reaction was stopped by adding $NaHCO_3$ thereto. The resulting mixture was extracted with ethyl acetate, the extract was dried over $MgSO_4$ and concentrated under a reduced pressure. The concentrate was dissolved in 50% methanol and 5% NaOCl (30 ml, 20.64 mmol) was added dropwise thereto. After 5 min, the resulting mixture was extracted with ethyl acetate, the extract was dried over $MgSO_4$ and concentrated under a reduced pressure. The resulting residue was purified by silica gel column chromatography (eluent—MeOH:$CDCl_3$=5:95, Merck, Silicagel 60) to obtain the title compound (18 g, 10.32 mmol) in a yield of 84%.

$^1$H NMR ($CDCl_3$): δ 8.23 (1H, br), 7.75 (1H, d), 7.44 (1H, d), 7.36–7.26 (2H, m), 7.03 (1H, s), 6.88 (1H, d), 3.96 (3H, s), 3.76 (3H, s)
MW: 318

(2) Preparation of 2-(2,4-dichloro-phenyl)-7-methoxy-1H-benzoimidazole-4-carboxylic acid methyl ester 3-[(2,4-dichloro-N-chloro-benzimidoyl)-amino]-4-methoxy-benzoic acid methyl ester (4 g, 10.32 mmol) obtained in step 1 was dissolved in 50 ml of 50% methanol and $NaHCO_3$ (2.19 g, 20.64 mmol) was added dropwise thereto at room temperature and refluxed for 5 min. The resulting solution was cooled to room temperature, extracted with ethyl acetate, and the extract was concentrated under a reduced pressure. The resulting residue was purified by recrystallization from ethyl acetate/hexane to obtain the title compound (3.2 g, 5.47 mmol) in a yield of 88%.

$^1$H NMR ($CDCl_3$): δ 8.54 (1H, d), 7.94 (1H, d), 7.48 (1H, s), 7.42 (1H, d), 6.76 (1H,d), 4.44 (3H, s), 3.99 (3H, s)
MW: 351

(3) Preparation of 2-(2,4-dichloro-phenyl)-7-hydroxy-1H-benzoimidazole-4-carboxylic acid 2-(2,4-dichloro-phenyl)-7-methoxy-1H-benzoimidazole-4-carboxylic acid methyl ester (1.9 g, 5.47 mmol) obtained in step 2 was dissolved in 100 ml of toluene, aluminum chloride (3.61 g, 27.05 mmol) was added thereto and refluxed for 8 hours. The resulting solution was cooled to room temperature, the reaction was stopped by adding 3 N HCl thereto and stirred for 30 min. The precipitate formed was filtered, washed with benzene and dried to obtain the title compound (1.63 g, 5.03 mmol) in a yield of 92%.

$^1$H NMR (DMSO-$d_6$): δ 8.19 (1H, d), 7.78 (1H, d), 7.62–7.55 (2H, m), 6.82 (1H, d)
MW: 323

(4) Preparation of 2-(2,4-dichloro-phenyl)-7-hydroxy-1H-benzoimidazole-4-carboxylic acid methyl ester 2-(2,4-dichloro-phenyl)-7-hydroxy-1H-benzoimidazole-4-carboxylic acid (1.63 g, 5.03 mmol) obtained in step 3 was dissolved in 30 ml of methanol, and $H_2SO_4$ (1.08 ml, 20.12 mmol) was added dropwise thereto and refluxed for 15 hours. The resulting solution was cooled to room temperature, concentrated under a reduced pressure to remove methanol, and the residue was neutralized with $NaHCO_3$. Then, the neutralized residue was extracted with ethyl acetate and concentrated under a reduced pressure to obtain a residue which was purified by recrystallization from ethyl acetate/hexane to obtain the title compound (1.5 g, 3.62 mmol) in a yield of 86%.

$^1$H NMR ($CDCl_3$): δ 11.42 (1H, br), 8.21 (1H, d), 7.89 (1H, d), 7.56 (1H, s), 7.38 (1H, d), 6.82 (1H, d), 3.99 (3H, s)
MW: 337

(5) Preparation of Wang resin-supported 2-(2,4-chloro-phenyl)-7-hydroxy-1H-benzoimidazole-4-carboxylic acid methyl ester p-nitrophenyl carbonate Wang resin (476 mg, 0.67 mmol) was dissolved in DMF, and 2-(2,4-dichloro-phenyl)-7-hydroxy-2H-benzoimidazole-4-carboxylic acid methyl ester (567 mg, 2.01 mmol), obtained in step 4, $Cs_2CO_3$ (655 mg, 2.01 mmol) and KI (334 mg, 2.01 mmol) were added thereto to be stirred at 50 to 60° C. for 12 hours. The resulting solution was cooled to room temperature and filtered. The filtrate was washed with DMF, MeOH and $CH_2Cl_2$ and dried to obtain the title compound (608 mg, 0.65 mmol) in a yield of 98%.

(6) Preparation of Wang resin-supported 2-(2,4-dichloro-phenyl)-7-hydroxy-1H-benzoimidazole-4-carboxylic acid Wang resin-supported 2-(2,4-dichloro-phenyl)-7-hydroxy-1H-benzoimidazole-4-carboxylic acid methyl ester (570 mg, 0.47 mmol) obtained in step 5 was dissolved in THF, LiOH.$H_2O$ (99 mg, 2.35 mmol) in MeOH—$H_2O$ (2:1) was added thereto and the resulting mixture was refluxed for 5 hours. The resulting solution was cooled to room temperature and filtered. The filtrate was washed with MeOH and $CH_2Cl_2$, and dried to obtain the title compound (551 mg, 0.42 mmol) in a yield of 90%.

PREPARATION EXAMPLE 4

Preparation of Wang resin-supported 2-(4-fluoro-phenyl)-7-hydroxy-1H-benzoimidazole-4-carboxylic acid ($R^1$=H, $R^2$=H and $R^3$=F)

(1) Preparation of 3-[(4-fluoro-benzimidoyl)-amino]-4-methoxy-benzoic acid methyl ester Anhydrous p-toluene sulfonic acid (41.99 g, 220.76 mmol) was melted at 120° C. and 3-amino-4-methoxy benzoic acid methyl ester (20 g, 110.38 mmol) obtained in step 1 of Preparation Example 1 and 4-fluorobenzonitrile (20.00 g, 165.57 mol) were added thereto and stirred at 160° C. for 8 hours. The resulting solution was cooled to room temperature and the reaction was stopped by adding $NaHCO_3$ thereto. The resulting mixture was extracted with ethyl acetate, the extract was dried over MgSO$_4$ and concentrated under a reduced pressure. The resulting residue was purified by silica gel column chromatography (eluent—MeOH:CDCl$_3$=5:95, Merck, Silicagel 60) to obtain the title compound (22.67 g, 75.06 mmol) in a yield of 68%.

$^1$H NMR (CDCl$_3$): δ 7.92–7.75 (4H, m), 7.15–7.02 (3H, m), 3.87–3.81 (6H, d)

MW: 302

(2) Preparation of 2-(4-fluoro-phenyl)-7-methoxy-1H-benzoimidazole-4-carboxylic acid methyl ester 3-[(4-fluoro-benzimidoyl)-amino]-4-methoxy-benzoic acid methyl ester (10 g, 34.48 mmol) obtained in step 1 was dissolved in 50% methanol and 5% NaOCl (61 ml, 41.38 mmol) was added dropwise thereto at room temperature. After 5 min, Na$_2$CO$_3$ (7.31 g, 68.96 mmol) was added dropwise thereto and refluxed for 5 min. The resulting solution was cooled to room temperature, extracted with ethyl acetate, and the extract was concentrated under a reduced pressure. The resulting residue was purified by silica gel column chromatography to obtain the title compound (5.66 g, 19.65 mmol) in a yield of 57%.

$^1$H NMR (CDCl$_3$): δ 8.18 (2H, t), 7.91 (1H, d), 7.30–7.25 (2H, t), 6.65 (1H, d), 6.85 (1H, d), 4.08 (3H, s), 3.98 (3H, s)

MW: 300

(3) Preparation of 2-(4-fluoro-phenyl)-7-hydroxy-1H-benzoimidazole-4-carboxylic acid 2-(4-fluoro-phenyl)-7-methoxy-1H-benzoimidazole-4-carboxylic acid methyl ester (3 g, 10.00 mmol) obtained in step 2 was dissolved in toluene, aluminum chloride (6.67 g, 30.00 mmol) was added thereto and refluxed for 8 hours. The resulting solution was cooled to room temperature, the reaction was stopped by adding 3 N HCl thereto and stirred for 30 min. The precipitate formed was filtered, washed with benzene and dried to obtain the title compound (1.96 g, 7.20 mmol) in a yield of 72%.

$^1$H NMR (MeOH-d$_4$): δ 8.19–8.15 (2H, t), 8.06 (1H, d), 7.50–7.44 (2H, t), 7.00 (1H, d)

MW: 272

(4) Preparation of 2-(4-fluoro-phenyl)-7-hydroxy-1H-benzoimidazole-4-carboxylic acid methyl ester 2-(4-fluoro-phenyl)-7-hydroxy-1H-benzoimidazole-4-carboxylic acid (500 mg, 1.84 mmol) obtained in step 3 was dissolved in methanol, H$_2$SO$_4$ (0.49 ml, 9.20 mmol) was added dropwise thereto and refluxed for 15 hours. The resulting solution was cooled to room temperature, concentrated under a reduced pressure to remove methanol, and the residue was neutralized with NaHCO$_3$. Then, the neutralized residue was extracted with ethyl acetate and concentrated under a reduced pressure to obtain a residue which was purified by silica gel chromatography to obtain the title compound (397 mg, 1.39 mmol) in a yield of 76%.

$^1$H NMR (CH$_3$OH-d$_4$): δ 8.22–8.18 (2H, t), 7.80 (1H, d), 7.32–7.26 (2H, t), 6.70 (1H, d), 3.97 (3H, s)

MW: 286

(5) Preparation of Wang resin-supported 2-(4-fluoro-phenyl)-7-hydroxy-1H-benzoimidazole-4-carboxylic acid methyl ester (4-bromomethylphenoxy)-methyl polystyrene Wang resin (476 mg, 0.67 mmol) was dissolved in DMF, and 2-(4-fluoro-phenyl)-7-hydroxy-1H-benzoimidazole-4-carboxylic acid methyl ester (567 mg, 2.01 mmol) obtained in step 4, Cs$_2$CO$_3$ (655 mg, 2.01 mmol) and KI (334 mg, 2.01 mmol) were added thereto to be stirred at 50 to 60° C. for 12 hours. The resulting solution was cooled to room temperature and filtered. The filtrate was washed with DMF, MeOH and CH$_2$Cl$_2$ and dried to obtain the title compound (608 mg, 0.65 mmol) in a yield of 98%.

(6) Preparation of Wang Resin-Supported 2-(4-fluoro-phenyl)-7-hydroxy-1H-benzoimidazole-4-carboxylic acid Wang resin-supported 2-(4-fluoro-phenyl)-7-hydroxy-1H-benzoimidazole-4-carboxylic acid methyl ester (570 mg, 0.47 mmol) obtained in step 5 was dissolved in THF, LiOH.H$_2$O (99 mg, 2.35 mmol) in MeOH—H$_2$O (2:1) was added thereto and the resulting mixture was refluxed for 5 hours. The resulting solution was cooled to room temperature and filtered. The filtrate was washed with MeOH and CH$_2$Cl$_2$, and dried to obtain the title compound (551 mg, 0.42 mmol) in a yield of 90%.

PREPARATION EXAMPLE 5

Preparation of Wang resin-supported 2-(2,4-difluoro-phenyl)-7-hydroxy-1H-benzoimidazole-4-carboxylic acid (R$^1$═F, R$^2$═H and R$^3$═F)

(1) Preparation of 3-[(2,4-difluoro-benzimidoyl)-amino]-4-methoxy-benzoic acid methyl ester Anhydrous p-toluene sulfonic acid (25.0 g, 137.43 mmol) was melted at 120° C. and 3-amino-4-methoxy benzoic acid methyl ester (10 g, 55.25 mmol) obtained in step 1 of Preparation Example 1 and 2,4-difluorobenzonitrile (11.53 g, 82.87 mol) were added thereto and stirred at 160° C. for 8 hours. The resulting solution was cooled to room temperature and the reaction was stopped by adding NaHCO$_3$ thereto. The resulting mixture was extracted with ethyl acetate, the extract was dried over MgSO$_4$ and concentrated under a reduced pressure. The resulting residue was purified by silica gel column chromatography to obtain the title compound (10.0 g, 31.22 mmol) in a yield of 57%.

$^1$H NMR (CDCl$_3$): δ 8.31–8.22 (1H, m), 7.82–7.79 (1H, d), 7.65 (1H, s), 7.02–6.85 (3H, m), 3.88 (6H, s)

MW: 320

(2) Preparation of 2-(2,4-difluoro-phenyl)-7-methoxy-1H-benzoimidazole-4-carboxylic acid methyl ester 3-[(2,4-difluoro-benzimidoyl)-amino]-4-methoxy-benzoic acid methyl ester (9.5 g, 29.66 mmol) obtained in step 1 was dissolved in 50% methanol and 5% NaOCl (53 ml, 35.71 mmol) was added dropwise thereto at room temperature. After 5 min, Na$_{2l\ CO3}$ (6.29 g, 59.34 mmol) was added dropwise thereto and refluxed for 5 min. The resulting solution was cooled to room temperature, extracted with ethyl acetate, and the extract was concentrated under a reduced pressure. The resulting residue was purified by silica gel column chromatography to obtain the title compound (3.50 g, 11.0 mmol) in a yield of 37%.

$^1$H NMR (CDCl$_3$): δ 10.99 (1H, bs). 8.65–8.57 (1H, m), 0.92 (1H, d), 7.10–6.97 (2H, m), 6.76 (1H, d), 4.13 (3H, s), 4.00 (3H, s)

MW: 318

(3) Preparation of 2-(2,4-difluoro-phenyl)-7-hydroxy-1H-benzoimidazole-4-carboxylic acid 2-(2,4-difluoro-phenyl)-7-methoxy-1H-benzoimidazole-4-carboxylic acid methyl ester (2.24 g, 7.04 mmol) obtained in step 2 was dissolved in toluene, aluminum chloride (3.75 g, 28.12 mmol) was added thereto and refluxed for 8 hours. The resulting solution was cooled to room temperature, the reaction was stopped by adding 3 N HCl thereto and stirred for 30 min. The precipitate formed was filtered, washed with benzene and dried to obtain the title compound (1.70 g, 5.86 mmol) in a yield of 83%.

$^1$H NMR (CH$_3$OH-d$_4$): δ 8.13–8.03 (2H, m), 7.47–7.33 (2H, m), 7.04 (1H, d)

MW: 290

(4) Preparation of 2-(2,4-difluoro-phenyl)-7-hydroxy-1H-benzoimidazole-4-carboxylic acid methyl ester 2-(2,4-difluoro-phenyl)-7-hydroxy-1H-benzoimidazole-4-carboxylic acid (1.70 mg, 5.86 mmol) obtained in step 3 was dissolved in methanol, SOCl$_2$ (8.2 ml, 112 mmol) was added dropwise thereto and refluxed for 15 hours. The resulting solution was cooled to room temperature, concentrated under a reduced pressure to remove methanol, and the residue was neutralized with NaHCO$_3$. Then, the neutralized residue was extracted with ethyl acetate and concentrated under a reduced pressure to obtain a residue which was purified by silica gel chromatography to obtain the title compound (1.50 mg, 1.64 mmol) in a yield of 84%.

$^1$H NMR (DMSO-d$_6$): δ 12.04 (1H, bs), 0.30–8.04 (1H, m), 7.73 (1H, d), 7.55–7.48 (1H, m), 7.33–7.27 (1H, m), 6.70 (1H, d), 4.01 (3H, s)

MW: 304

(5) Preparation of Wang resin-supported 2-(2,4-difluoro-phenyl)-7-hydroxy-1H-benzoimidazole-4-carboxylic acid methyl ester (4-bromomethylphenoxy)-methyl polystyrene Wang resin (476 mg, 0.67 mmol) was dissolved in DMF, and 2-(2,4-difluoro-phenyl)-7-hydroxy-1H-benzoimidazole-4-carboxylic acid methyl ester (567 mg, 2.01 mmol) obtained in step 4, Cs$_2$CO$_3$ (655 mg, 2.01 mmol) and KI (334 mg, 2.01 mmol) were added thereto to be stirred at 50 to 60° C. for 12 hours. The resulting solution was cooled to room temperature and filtered. The filtrate was washed with DMF, MeOH and CH$_2$Cl$_2$ and dried to obtain the title compound (608 mg, 0.65 mmol) in a yield of 98%.

(6) Preparation of Wang resin-supported 2-(2,4-difluoro-phenyl)-7-hydroxy-1H-benzoimidazole-4-carboxylic acid Wang resin-supported 2-(2,4-difluoro-phenyl)-7-hydroxy-1H-benzoimidazole-4-carboxylic acid methyl ester (570 mg, 0.47 mmol) obtained in step 5 was dissolved in THF, LiOH.H$_2$O (99 mg, 2.35 mmol) in MeOH—H$_2$O was added thereto and the resulting mixture was refluxed for 5 hours. The resulting solution was cooled to room temperature and filtered. The filtrate was washed with MeOH and CH$_2$Cl$_2$, and dried to obtain the title compound (551 mg, 0.42 mmol) in a yield of 90%.

PREPARATION EXAMPLE 6

Preparation of Wang resin-supported 2-(2-chloro-4-fluoro-phenyl)-7-hydroxy-1H-benzoimidazole-4-carboxylic acid (R$^1$=Cl, R$^2$=H and R$^3$=F)

(1) Preparation of 3-[(2-chloro-4-fluoro-benzimidoyl)-amino]-4-methoxy-benzoic acid methyl ester Anhydrous p-toluene sulfonic acid (41.99 g, 220.76 mmol) was melted at 120° C. and 3-amino-4-methoxy benzoic acid methyl ester (20 g, 110.38 mmol) obtained in step 1 of Preparation Example 1 and 2-chloro-4-fluorobenzonitrile (25.76 g, 165.57 mol) were added thereto and stirred at 160° C. for 8 hours. The resulting solution was cooled to room temperature and the reaction was stopped by adding NaHCO$_3$ thereto. The resulting mixture was extracted with ethyl acetate, the extract was dried over MgSO$_4$ and concentrated under a reduced pressure. The resulting residue was purified by silica gel column chromatography to obtain the title compound (26.70 g, 79.47 mmol) in a yield of 72%.

$^1$H NMR (CDCl$_3$): δ 7.92–7.75 (4H, m), 7.15–7.02 (3H, m), 3.87–3.81 (6H, d)

MW: 336

(2) Preparation of 2-(2-chloro-4-fluoro-phenyl)-7-methoxy-1H-benzoimidazole-4-carboxylic acid methyl ester 3-[(2-chloro-4-fluoro-benzimidoyl)-amino]-4-methoxy-benzoic acid methyl ester (10 g, 29.76 mmol) obtained in step 1 was dissolved in 50% methanol and 5% NaOCl (53 ml, 35.71 mmol) was added dropwise thereto at room temperature. After 5 min, Na$_2$CO$_3$ (6.31 g, 59.52 mmol) was added dropwise thereto and refluxed for 5 min. The resulting solution was cooled to room temperature, extracted with ethyl acetate, the extract was concentrated under a reduced pressure. The resulting residue was purified by silica gel column chromatography to obtain the title compound (5.17 g, 15.48 mmol) in a yield of 52%.

$^1$H NMR (CDCl$_3$): δ 8.18 (2H, t), 0.91 (1H, d), 7.30–7.25 (2H, t), 6.65 (1H, d), 6.85 (1H, d), 4.08 (3H, s), 3.98 (3H, s)

MW: 334

(3) Preparation of 2-(2-chloro-4-fluoro-phenyl)-7-hydroxy-1H-benzoimidazole-4-carboxylic acid 2-(2-chloro-4-fluoro-phenyl)-7-methoxy-1H-benzoimidazole-4-carboxylic acid methyl ester (3 g, 8.98 mmol) obtained in step 2 was dissolved in toluene and aluminum chloride (5.99 g, 44.90 mmol) was added thereto, refluxed for 8 hours. The resulting solution was cooled to room temperature, the reaction was stopped by adding 3 N HCl thereto and stirred for 30 min. The precipitate formed was filtered, washed with benzene and dried to obtain the title compound (1.87 g, 6.11 mmol) in a yield of 68%.

$^1$H NMR (CH$_3$OH-d$_4$): δ 8.19–8.15 (2H, t), 8.06 (1H, d), 7.50–7.44 (2H, t), 7.00 (1H, d)

MW: 306

(4) Preparation of 2-(2-chloro-4-fluoro-phenyl)-7-hydroxy-1H-benzoimidazole-4-carboxylic acid methyl ester 2-(2-chloro-4-fluoro-phenyl)-7-hydroxy-1H-benzoimidazole-4-carboxylic acid (500 mg, 1.63 mmol) obtained in step 3 was dissolved in methanol, $H_2SO_4$ (0.43 ml, 8.15 mmol) was added dropwise thereto and refluxed for 15 hours. The resulting solution was cooled to room temperature, concentrated under a reduced pressure to remove methanol, and the residue was neutralized with $NaHCO_3$. Then, the neutralized residue was extracted with ethyl acetate and concentrated under a reduced pressure to obtain a residue which was purified by silica gel chromatography to obtain the title compound (393 mg, 1.23 mmol) in a yield of 67%.

$^1$H NMR ($CH_3OH$-$d_4$): δ 8.22–8.18 (2H, t), 7.80 (1H, d), 7.32–7.26 (2H, t), 6.70 (1H, d), 3.97 (3H, s)

MW: 320

(5) Preparation of Wang resin-supported 2-(2-chloro-4-fluoro-phenyl)-7-hydroxy-1H-benzoimidazole-4-carboxylic acid methyl ester (4-bromomethylphenoxy)-methyl polystyrene Wang resin (476 mg, 0.67 mmol) was dissolved in DMF, and 2-(2-chloro-4-fluoro-phenyl)-7-hydroxy-1H-benzoimidazole-4-carboxylic acid methyl ester (567 mg, 2.01 mmol) obtained in step 4, $Cs_2CO_3$ (655 mg, 2.01 mmol) and KI (334 mg, 2.01 mmol) were added thereto to be stirred at 50 to 60° C. for 12 hours. The resulting solution was cooled to room temperature and filtered. The filtrate was washed with DMF, MeOH and $CH_2Cl_2$ and dried to obtain the title compound (608 mg, 0.65 mmol) in a yield of 98%.

(6) Preparation of Wang resin-supported 2-(2-chloro-4-fluoro-phenyl)-7-hydroxy-1H-benzoimidazole-4-carboxylic acid Wang resin-supported 2-(2-chloro-4-fluoro-phenyl)-7-hydroxy-1H-benzoimidazole-4-carboxylic acid methyl ester (570 mg, 0.47 mmol) obtained in step 5 was dissolved in THF, LiOH.$H_2O$ (99 mg, 2.35 mmol) in MeOH—$H_2O$ was added thereto and the resulting mixture was refluxed for 5 hours. The resulting solution was cooled to room temperature and filtered. The filtrate was washed with MeOH and $CH_2Cl_2$, and dried to obtain the title compound (551 mg, 0.42 mmol) in a yield of 90%.

PREPARATION EXAMPLE 7

Preparation of Wang resin-supported 2-(3-chloro-4-fluoro-phenyl)-7-hydroxy-1H-benzoimidazole-4-carboxylic acid ($R^1$=H, $R^2$=Cl and $R^3$=F)

(1) Preparation of 3-[(3-chloro-4-fluoro-benzimidoyl)-amino]-4-methoxy-benzoic acid methyl ester Anhydrous p-toluene sulfonic acid (10 g, 52.57 mmol) was melted at 120° C. and 3-amino-4-methoxy benzoic acid methyl ester (3.88 g, 21.44 mmol) obtained in step 1 of Preparation Example 1 and 3-chloro-4-fluorobenzonitrile (5.0 g, 32.14 mol) were added thereto and stirred at 160° C. for 8 hours. The resulting solution was cooled to room temperature and the reaction was stopped by adding $NaHCO_3$ thereto. The resulting mixture was extracted with ethyl acetate, the extract was dried over $MgSO_4$ and concentrated under a reduced pressure. The resulting residue was purified by silica gel column chromatography to obtain the title compound (3.24 g, 9.62 mmol) in a yield of 45%.

$^1$H NMR ($CDCl_3$): δ 7.96–7.95 (1H, m), 7.76–7.73 (2H, m), 7.60 (1H, bs), 7.17–7.11 (1H, m), 6.93(1H, d), 3.85(3H, s), 3.84 (3H, d)

MW: 336

(2) Preparation of 2-(3-chloro-4-fluoro-phenyl)-7-methoxy-1H-benzoimidazole-4-carboxylic acid methyl ester 3-[(3-chloro-4-fluoro-benzimidoyl)-amino]-4-methoxy-benzoic acid methyl ester (3.24 g, 9.62 mmol) was dissolved in 50% methanol and 5% NaOCl (18 ml, 11.90 mmol) was added dropwise thereto at room temperature. After 5 min, $Na_2CO_3$ (2.04 g, 19.25 mmol) was added dropwise thereto and refluxed for 5 min. The resulting solution was cooled to room temperature, extracted with ethyl acetate, and the extract was concentrated under a reduced pressure. The resulting residue was purified by silica gel column chromatography to obtain the title compound (0.95 g, 2.83 mmol) in a yield of 30%.

$^1$H NMR ($CDCl_3$): δ 10.68 (1H, bs), 8.23–8.20 (1H, m), 7.96–7.91 (1H, m), 7.87 (1H, d), 7.27–7.20 (1H, m), 6.73 (1H, d), 4.10 (3H, s), 3.97 (3H, s)

MW: 334

(3) Preparation of 2-(3-chloro-4-fluoro-phenyl)-7-hydroxy-1H-benzoimidazole-4-carboxylic acid 2-(3-chloro-4-fluoro-phenyl)-7-methoxy-1H-benzoimidazole-4-carboxylic acid methyl ester (0.95 g, 8.98 mmol) obtained in step 2 was dissolved in toluene, aluminum chloride (1.5 g, 11.25 mmol) was added thereto and refluxed for 8 hours. The resulting solution was cooled to room temperature, the reaction was stopped by adding 3 N HCl thereto and stirred for 30 min. The precipitate formed was filtered, washed with benzene and dried to obtain the title compound (0.81 g, 2.64 mmol) in a yield of 80%.

$^1$H NMR (MeOH-$d_4$): δ 8.34 (1H, dd), 8.22–8.08 (2H, m), 7.62 (1H, t), 7.03 (1H, d)

MW: 306

(4) Preparation of 2-(3-chloro-4-fluoro-phenyl)-7-hydroxy-1H-benzoimidazole-4-carboxylic acid methyl ester 2-(3-chloro-4-fluoro-phenyl)-7-hydroxy-1H-benzoimidazole-4-carboxylic acid (800 mg, 2.64 mmol) obtained in step 3 was dissolved in methanol, $SOCl_2$ (1.93 ml, 26.41 mmol) was added dropwise thereto and refluxed for 15 hours. The resulting solution was cooled to room temperature, concentrated under a reduced pressure to remove methanol, and the residue was neutralized with $NaHCO_3$. Then, the neutralized residue was extracted with ethyl acetate and concentrated under a reduced pressure to obtain a residue which was purified by silica gel chromatography to obtain the title compound (690 mg, 2.15 mmol) in a yield of 81%.

$^1$H NMR (DMSO-$d_6$): δ 12.39 (1H, bs), 8.56 (1H, d), 8.30 (1H, bs), 7.72 (1H, d), 7.59 (1H, t), 6.69 (1H, d), 3.90 (3H, s)

MW: 320

(5) Preparation of Wang resin-supported 2-(3-chloro-4-fluoro-phenyl)-7-hydroxy-1H-benzoimidazole-4-carboxylic acid methyl ester (4-bromomethylphenoxy)-methyl polystyrene Wang resin (476 mg, 0.67 mmol) was dissolved in DMF, and 2-(3-chloro-4-fluoro-phenyl)-7-hydroxy-1H-benzoimidazole-4-carboxylic acid methyl ester (567 mg, 2.01 mmol) obtained in step 4, $Cs_2CO_3$ (655 mg, 2.01 mmol) and KI (334 mg, 2.01 mmol) were added thereto to be stirred at 50 to 60° C. for 12 hours. The resulting solution was cooled to room temperature and filtered. The filtrate was washed with DMF, MeOH and $CH_2Cl_2$ and dried to obtain the title compound (608 mg, 0.65 mmol) in a yield of 98%.

(6) Preparation of Wang resin-supported 2-(3-chloro-4-fluoro-phenyl)-7-hydroxy-1H-benzoimidazole-4-carboxylic acid Wang resin-supported 2-(3-chloro-4-fluoro-phenyl)-7-hydroxy-1H-benzoimidazole-4-carboxylic acid methyl ester (570 mg, 0.47 mmol) obtained in step 5 was dissolved in THF, $LiOH.H_2O$ (99 mg, 2.35 mmol) in $MeOH—H_2O$ was added thereto and the resulting mixture was refluxed for 5 hours. The resulting solution was cooled to room temperature and filtered. The filtrate was washed with MeOH and $CH_2Cl_2$, and dried to obtain the title compound (551 mg, 0.42 mmol) in a yield of 90%.

EXAMPLE 1

Preparation of 7-hydroxy-2-phenyl-1H-benzoimidazole-4-carboxylic acid amide ($R^4R^5NH_2$=$NH_4Cl$)

Wang resin-supported 7-hydroxy-2-phenyl-1H-benzoimidazole-4-carboxylic acid (36 mg, 0.03 mmol) obtained in Preparation Example 1 was dissolved in 3 ml of DMF and aluminum chloride (5 mg, 0.09 mmol), EDCI (18 mg, 0.09 mmol), DMAP (11 mg, 0.09 mmol) and HOBt (12 mg, 0.09 mmol) were added thereto and the resulting mixture was stirred at room temperature. The resulting solution was filtered, the filtrate was washed with DMF, MeOH and $CH_2Cl_2$ and dried to obtain Wang resin-supported 7-hydroxy-2-phenyl-1H-benzoimidazole-4-carboxylic acid amide.

Then, 30 mg of Wang resin-supported 7-hydroxy-2-phenyl-1H-benzoimidazole-4-carboxylic acid amide was dissolved in 0.2 ml of $CH_2Cl_2$, 0.2 ml of trifluoroacetic acid was added thereto and stirred for 30 min. The resulting solution was filtered, the filtrate was washed with MeOH and $CH_2Cl_2$ and dried to obtain the title compound in a yield of 90%.

$^1H$ NMR ($CH_3OH-d_4$): δ 8.15 (2H, d), 7.84 (1H, d), 7.78–7.56 (3H, m), 6.83 (1H, m)

MW: 253

EXAMPLE 2 TO 203

The same procedure as described in Example 1 was repeated using $R^4R^5NH_2$ listed in Table 2 to obtain the compounds 2 to 203, respectively.

TABLE 2

| Com No. | Pre No. | Chemical compound | $R^4N(CH_2)_nR^5$ | n | $^1H$ NMR($CH_3OH-d_4$) | MW |
|---|---|---|---|---|---|---|
| 2 | 1 | 7-hydroxy-2-phenyl-1H-benzoimidazole-4-carboxylic acid-phenylamide | aniline | 0 | δ 8.10(2H, d), 7.87(1H, d), 7.85–7.60(3H, m), 7.40(2H, d), 07.39–7.28(2H, m), 7.27–7.20(1H, m), 6.89(1H, d) | 329 |
| 3 | 1 | 7-hydroxy-2-phenyl-1H-benzoimidazole-4-carboxylic acid(4-hydroxy-phenyl)-amide | 4-hydroxyaniline | 0 | δ 8.28–8.03(3H, m), 7.98–7.82(1H, d), 7.79–7.56(3H, m), 7.48(2H, d), 6.85–6.72(2H, m) | 345 |
| 4 | 1 | 7-hydroxy-2-phenyl-1H-benzoimidazole-4-carboxylic acid(4-amino-phenyl)-amide | 1,4-diaminophenylene | 0 | δ 8.28–8.14(2H, m), 8.03–7.91(3H, m), 7.71–7.56(3H, m), 7.46–7.34(2H, d), 6.89–6.76(1H, d) | 344 |
| 5 | 1 | 7-hydroxy-2-phenyl-1H-benzoimidazole-4-carboxylic acid(4-hydroxy-cyclohexyl)-amide | 4-hydroxycyclohexylamine | 0 | δ 8.08(2H, d), 7.82(1H, d), 7.78–7.50(3H, m), 6.88(1H, d), 4.15–3.82(1H, m), 3.70–3.54(1H, m), 2.30–1.90(4H, m), 1.85–1.20(4H, m) | 351 |
| 6 | 1 | 7-hydroxy-2-phenyl-1H-benzoimidazole-4-carboxylic acid(4-hydroxymethyl-phenyl)-amide | 4-(hydroxymethyl)aniline | 0 | δ 8.20(2H, d), 7.92(2H, d), 7.81–7.70(1H, m), 7.69–7.58(3H, m), 7.50–7.30(1H, m), 7.29–7.10(1H, m), 6.89(1H, d), 4.65(2H, s) | 359 |
| 7 | 1 | 7-hydroxy-2-phenyl-1H-benzoimidazole-4-carboxylic acid[4-(2-hydroxy-ethyl)-phenyl]-amine | 4-(hydroxyethyl)aniline | 0 | δ 8.14(2H, d), 7.98(1H, d), 7.78–7.60(5H, m), 7.30–7.18(2H, m), 6.88(1H, d), 4.65(1H, t), 3.73(1H, t), 3.02(1H, t), 2.81(1H, t) | 373 |
| 8 | 1 | 7-hydroxy-2-phenyl-1H-benzoimidazole-4-carboxylic acid[4-(2-amino-ethyl)-phenyl]-amide | 4-(aminoethyl)aniline | 0 | δ 8.27–8.16(2H, m), 7.95(1H, d), 7.78(2H, d), 7.66–7.54(3H, m), 7.44(2H, d), 6.86(1H, d), 3.19(2H, t), 2.92(2H, t) | 372 |
| 9 | 1 | 7-hydroxy-2-phenyl-1H-benzoimidazole-4-carboxylic acid{4-[2-(toluene-4-sulfonyl-amino)-ethyl]-phenyl}-amide | N-[2-(4-amino-phenyl)-ethyl]-4-methylbenzene-sulfonamide | 0 | δ 8.20–8.02(3H, m), 8.00(2H, d), 7.70–7.68(5H, m), 7.38(2H, d), 7.16(2H, d), 6.94(1H, d), 3.10(2H, t), 2.73(2H, t), 2.43(3H, s) | 526 |
| 10 | 1 | 7-hydroxy-2-phenyl-1H-benzoimidazole-4-carboxylic acid[4-(2-methanesulfonyl-amino-ethyl)-phenyl]-amide | N-[2-(4-amino-phenyl)-ethyl]-4-methane-sulfonamide | 0 | δ 8.13(2H, d), 7.98(1H, d), 7.75–7.53(5H, m), 7.29(2H,d), 6.91(1H, d), 3.30(2H, t), 2.82(2H, t) | 450 |
| 11 | 1 | 7-hydroxy-2-phenyl-1H-benzoimidazole-4-carboxylic-acid{4-[2-(1,3-dioxo-1,3- | 2-[2-(4-aminophenyl)-ethyl]-isoindole-1,3-dione | 0 | δ 7.45(2H, d), 6.98–6.84(4H, m), 6.82(2H, d), 6.73–6.54(4H, m), 6.30(2H, d), 5.89(1H, d), 2.91(2H, t), 2.00(2H, t) | 502 |

TABLE 2-continued

| Com No. | Pre No. | Chemical compound | R⁴N(CH₂)ₙR⁵ | n | ¹H NMR(CH₃OH-d₄) | MW |
|---|---|---|---|---|---|---|
| | | dihydro-isoindole-2-yl)-ethyl]-phenyl}-amide | | | | |
| 12 | 1 | 7-hydroxy-2-phenyl-1H-benzoimidazole-4-carboxylic acid{4-[2-(thiophene-2-sulfonylamino)-ethyl]-phenyl}-amide | thiophene-2-sulfonic acid [2-(4-amino-phenyl)-ethyl]-amide | 0 | δ 8.15(2H, d), 8.06(1H, d), 7.80–7.55(7H, m), 7.23–7.10(3H, m), 7.05(1H, d), 3.16(2H, t), 2.80(2H, t) | 518 |
| 13 | 1 | 7-hydroxy-2-phenyl-1H-benzoimidazole-4-carboxylic acid[4-(2-ethanesulfonylamino-ethyl)-phenyl]-amide | N-[2-(4-amino-phenyl)-ethyl]-ethanesulfonamide | 0 | δ 8.17(2H, d), 8.03(1H, d), 7.77–7.68(5H, m), 7.27(2H, d), 7.01(1H, d), 3.31(2H, t), 2.99(2H, q), 2.85(2H, t), 1.23(3H, t) | 464 |
| 14 | 2 | 2-(4-chloro-phenyl)-7-hydroxy-1H-benzoimidazole-4-carboxylic acid phenylamide | aniline | 0 | δ 8.18(2H, d), 8.11(1H, d), 7.80(2H, d), 7.67(2H, d), 7.40(2H, t), 7.15(1H, t), 6.89(1H, d) | 363 |
| 15 | 2 | 2-(4-chloro-phenyl)-7-hydroxy-1H-benzoimidazole-4-carboxylic acid(4-hydroycyclohexyl)-amide | 4-hydroxycyclo-hexylamine | 0 | δ 8.15(2H, d), 7,84(1H, d), 7.69(2H, d), 6.90(1H, d), 3.95(1H, m), 3.58(1H, m), 2.28–1.95(4H, m), 1.83–1.25(4H, m) | 385 |
| 16 | 2 | 2-(4-chloro-phenyl)-7-hydroxy-1H-benzoimidazole-4-carboxylic acid{4-[2-(toluene-4-sulfonyl-amino)-ethyl]-phenyl}-amide | N-[2-(4-amino-phenyl)-ethyl]-4-methyl-benzenesulfonamide | 0 | δ 8.18(2H, d), 7.98(1H, d), 7.80–7.60(6H, m), 7.36(2H, d), 7.16(2H, d), 6.94(1H, d), 3.09(2H, t), 2.74(2H, t), 2.41(3H, s) | 560 |
| 17 | 2 | 2-(4-chloro-phenyl)-7-hydroxy-1H-benzoimidazole-4-carboxylic acid[4-(2-methanesulfonyl-amino-ethyl)-phenyl]-amide | N-[2-(4-amino-phenyl)-ethyl]-methenesulfonyl-amide | 0 | δ 8.15(1H, d), 7.94(1H, d), 7.72(2H, d), 7.62(2H, d), 7.28(2H, d), 6.85(1H, d), 3.32(2H, t), 2.85(3H, s), 2.84(2H, t) | 484 |
| 18 | 2 | 2-(4-chloro-phenyl)-7-hydroxy-1H-benzoimidazole-4-carboxylic acid{4-[2-(1,3-dioxo-1,3-dihydro-isoindole-2-yl)-ethyl]-phenyl}-amide | 2-[2-(4-amino-phenyl)-ethyl]-isoindole-1,3-dione | 0 | δ 8.16(2H, d), 8.02(1H, d), 7.86–7.76(4H, m), 7.75–7.61(4H, m), 7.22(2H, d), 6.95(1H, m), 3.90(2H, t), 2.97(2H, t) | 536 |
| 19 | 2 | 2-(4-chloro-phenyl)-7-hydroxy-1H-benzoimidazole-4-carboxylic acid{4-[2-(thiophene-2-sulfonyl-amino-ethyl)-phenyl]-amide | thiophene-2-sulfonic acid[2-(4-amino-phenyl)-ethyl]-amide | 0 | δ 8.15(2H, d), 7.97(2H, d), 7.75–7.57(6H, m), 7.19(2H, d), 6.92(1H, d), 3.17(2H, t), 2.77(2H, t) | 552 |
| 20 | 2 | 2-(4-chloro-phenyl)-7-hydroxy-1H-benzoimidazole-4-carboxylic acid[4-(2-ethanesulfonylamino-ethyl)-phenyl]-amide | N-[2-(4-amino-phenyl)-ethyl]-ethanesulfonylamide | 0 | δ 8.17(2H, d), 8.09(2H, d), 7.73(2H, d), 7.63(2H, d), 7.29(2H, d), 3.31(2H, t), 2.98(2H, q), 2.85(2H, t), 1.24(3H, t) | 498 |
| 21 | 3 | 2-(2,4-dichloro-phenyl)-7-hydroxy-1H-benzoimidazole-4-carboxylic acid phenylamide | ammonium chloride | 0 | δ 7.98–7.70(2H, m), 7.69–7.52(1H, m), 7.28–7.00(1H, m), 6.95–6.82(1H, m) | 321 |
| 22 | 3 | 2-(2,4-dichloro-phenyl)-7-hydroxy-1H-benzoimidazole-4-carboxylic acid phenylamide | aniline | 0 | δ 8.02(1H, d), 8.01–7.82(1H, m), 7.81–7.65(3H, m), 7.64–7.45(1H, m), 7.43–7.20(2H, m), 7.42–7.02(1H, t), 6.90(1H, d) | 397 |
| 23 | 3 | 2-(2,4-dichloro-phenyl)-7-hydroxy-1H-benzoimidazole-4-carboxylic acid(4-hydroxy-cyclohexyl)-amide | 4-hydroxy-cyclohexyl-amine | 0 | δ 8.02–7.68(2H, m), 7.68–7.48(1H, m), 7.20–7.03(1H, m), 6.88(1H, d), 3.93(1H, m), 3.58(1H, m), 2.25–1.85(4H, m), 1.84–1.39(4H, m) | 419 |
| 24 | 3 | 2-(2,4-dichloro-phenyl)-7-hydroxy-1H-benzoimidazole-4-carboxylic acid[4-(2-amino-ethyl)-phenyl]-amide | 4-aminophenethylamine | 0 | δ 7.97(2H, d), 7.85–7.63(3H, m), 7.56(1H, d), 7.38–7.20(2H, m), 6.82(1H, d), 3.18(2H, t), 2.96(2H, t) | 440 |
| 25 | 3 | 2-(2,4-Dichloro-phenyl)-7-hydroxy-1H-benzoimidazole-4-carboxylic acid(4-amino-phenyl)-amide | 1,4-phenylenediamine | 0 | δ 8.06–7.81(4H, m), 7.80–7.64(1H, s), 7.58(1H, d), 7.38(2H, d), 6.84(1H, d) | 412 |
| 26 | 3 | 2-(2,4-Dichloro-phenyl)-7-hydroxy-1H-benzoimidazole-4-carboxylic acid(4-hydroxy-methyl-phenyl)-amide | 4-aminobenzy alcohol | 0 | δ 8.00(1H, d), 7.98–7.84(1H, m), 7.75(1H, m), 7.74–7.52(2H, m), 7.50–7.26(1H, m), 7.25–7.05(2H, m), 7.04–6.80(1H, m) | 427 |
| 27 | 3 | 2-(2,4-Dichloro-phenyl)-7-hydroxy-1H-benzoimidazole-4-carboxylic acid[4-(2-hydroxy-ethyl)-phenyl]-amide | 4-aminophenethyl alcohol | 0 | δ 8.15–7.86(2H, m), 7.85–7.45(3H, m), 7.25(2H, d), 7.20–6.75(2H, m), 4.58(1H, t), 3.75(1H, t), 3.05(1H, t), 2.81(1H, t) | 441 |
| 28 | 3 | 2-(2,4-dichloro-phenyl)-7-hydroxy-1H-benzoimidizaole-4-carboxylic acid{4-[2-(toluene-4-sulfonylamino)-ethyl]-phenyl}-amide | N-[2-(4-amino-phenyl)-ethyl]-4-methyl-benzene-sulfonamide | 0 | δ 8.20–8.02(3H, m), 8.00(2H, d), 7.70–7.68(3H, m), 7.38(2H, d), 7.16(2H, d), 6.94(1H, d), 3.10(2H, t), 2.73(2H, t), 2.43(3H, s) | 594 |
| 29 | 3 | 2-(2,4-dichloro-phenyl)-7-hydroxy-1H-benzoimidazole-4-carboxylic acid[4-(2-methane-sulfonylamino-ethyl)-phenyl]-amide | N-[2(4-amino-phenyl)-ethyl]-methanesulfonamide | 0 | δ 8.02(1H, d), 8.01–7.78(1H, m), 7.70(2H, d), 7.67–7.50(1H, m), 7.25(2H, d), 6.90(2H, d), 3.28(2H, t), 2.84(2H, t), 2.82(3H, s) | 518 |
| 30 | 3 | 2-(2,4-dichloro-phenyl)-7-hydroxy-1H-benzoimidazole-4- | 2-[2-(4-amino-phenyl)-ethyl]-isoindole-1,3-dione | 0 | δ 7.10(1H, d), 6.99–6.81(6H, m), 6.80–6.65(3H, m), 6.28(2H, d), 5.92(1H, d), 2.88(2H, t), | 570 |

TABLE 2-continued

| Com No. | Pre No. | Chemical compound | R⁴N(CH₂)ₙR⁵ | n | ¹H NMR(CH₃OH-d₄) | MW |
|---|---|---|---|---|---|---|
|  |  | carboxylic acid{4-[2-(1,3-dioxo-1,3-dihydro-isoindole-2-yl)-ethyl]-phenyl}-amide |  |  | 1.97(2H, t) |  |
| 31 | 3 | 2-(2,4-dichloro-phenyl)-7-hydroxy-1H-benzoimidazole-4-carboxylic acid{4-[2-(thiophene-2-sulfonylamino)-ethyl]-phenyl}-amide | thiophene-2-sulfonic acid[2-(4-amino-phenyl)-ethyl]-amide | 0 | δ 8.08(1H, d), 7.88(2H, m), 7.83(1H, d), 7.75(1H, d), 7.68–7.65(3H, m), 7.63(1H, d), 7.17–7.01(2H, m), 6.97(1H, d), 3.16(2H, t), 2.77(2H, t) | 586 |
| 32 | 3 | 2-(2,4-dichloro-phenyl)-7-hydrioxy-1H-benzoimidazole-4-carboxylic acid[4-(2-ethane-sulfonylamino-ethyl)-phenyl]-amide | N-[2-(4-amino-phenyl)-ethyl]-ethanesulfonamide | 0 | δ 8.11(1H, d), 7.95–7.82(2H, m), 7.75–7.60(3H, m), 7.28(2H, d), 7.01(1H, d), 3.31(2H, t), 2.98(2H, q), 2.85(2H, t), 1.24(3H, t) | 532 |
| 33 | 4 | 2-(4-fluoro-phenyl)-7-hydroxy-1H-benzoimidazole-4-carboxylic acid[4-(2-methanesulfonyl-amino-ethyl)-phenyl]-amide | N-[2-(4-amino-phenyl)-ethyl]-methanesulfonamide | 0 | δ 8.23–8.15(2H, m), 7.91(1H, d), 7.69(2H, d), 7.39(2H, t), 7.26(2H, d), 6.83(1H, d), 3.31(2H, t), 2.85–2.78(5H, m) |  |
| 34 | 4 | 2-(4-fluoro-phenyl)-7-hydroxy-1H-benzoimidazole-4-carboxylic acid{4-[2-(toluene-4-sulfonyl-amino)-ethyl]-amide | N-[2-(4-amino-phenyl)-ethyl]-4-methyl-benzenesulfonamide | 0 | δ 8.25–8.21(2H, m), 7.98–7.93(2H, m), 7.71–7.64(4H, m), 7.41–7.34(3H, m), 7.14(2H, d), 6.87(1H, d), 3.08(2H, t), 2.73(2H, t), 2.40(3H, s) |  |
| 35 | 4 | 2-(4-fluoro-phenyl)-7-hydroxy-1H-benzoimidazole-4-carboxylic acid[4-(2-methanesulfonyl-amino-ethyl)-phenyl]-amide | N-[2-(4-amino-phenyl)-ethyl]-ethanesulfonamide | 0 | δ 8.05(2H, t), 7.78(1H, d), 7.30(2H, t), 7.14(2H, d), 6.77(2H, d), 6.69(1H, d), 3.78(2H, q), 3.35(2H, t), 2.90(2H, t), 1.28(3H, t) |  |
| 36 | 4 | 2-(4-fluoro-phenyl)-7-hydroxy-1H-benzoimidazole-4-carboxylic acid(4-morpholin-4-yl-phenyl)-amide | 4-morpholin-4-yl-phenylamine | 0 |  |  |
| 37 | 5 | 2-(2,4-difluoro-phenyl)-7-hydroxy-1H-benzoimidazole-4-carboxylic acid[4-(2-methane-sulfonylamino-ethyl)-phenyl]-amide | N-[2-(4-amino-phenyl)-ethyl]-methanesulfonamide | 0 | δ 7.90(1H, d), 7.62(1H, d), 7.31–7.17(4H, m), 6.81(1H, d), 3.22(2H, t), 2.76(5H, m) |  |
| 38 | 5 | 2-(2,4-difluoro-phenyl)-7-hydroxy-1H-benzoimidazole-4-carboxylic acid {4-[2-(toluene-4-sulfonylamino)-ethyl]-phenyl}amide | N-[2-(4-amino-phenyl)-ethyl]-4-methyl-benzene-sulfonamide | 0 | δ 7.99(1H, m), 7.74(1H, d), 7.50(2H, d), 7.33–7.26(2H, m), 7.23(4H, m), 6.94(2H, d), 6.81(1H, d), 3.58(2H, t), 2.82(2H, t), 2.23(3H, s) |  |
| 39 | 5 | 2-(2,4-difluoro-phenyl)-7-hydroxy-1H-benzoimidazole-4-carboxylic acid[4-(2-methane-sulfonylamino-ethyl)-phenyl]-amide | N-[2-(4-amino-phenyl)-ethyl]-ethanesulfonamide | 0 | δ 8.19–8.00(2H, m), 7.70(1H, d), 7.43–7.26(4H, m), 6.87(1H, d), 3.98(2H, t), 2.97(2H, q), 2.86(2H, t), 1.25(3H, t) |  |
| 40 | 6 | 2-(2-chloro-4-fluoro-phenyl)-7-hydroxy-1H-benzoimidazole-4-carboxylic acid{4-[2-(toluene-4-sulfonylamino)-ethyl]-phenyl}amide | N-[2-(4-amino-phenyl)-ethyl]-4-methyl-benzene-sulfonamide) | 0 | δ 8.01–7.93(1H, m), 7.65(3H, t), 7.53–7.44(2H, m), 7.33(4H, m), 7.11(2H, d), 6.80(1H, d), 3.09(2H, t), 2.72(2H, t), 2.38(3H, s) |  |
| 41 | 6 | 2-(2-chloro-4-fluoro-phenyl)-7-hydroxy-1H-benzoimidazole-4-carboxylic acid[4-(2-methanesulfonylamino-ethyl)-phenyl]-amide | N-[2-(4-amino-phenyl)-ethyl]-methanesulfonamide | 0 | δ 8.06(1H, m), 7.97(1H, d), 7.68–7.61(3H, m), 7.40(1H, m), 7.27(2H, d), 6.97(1H, m), 3.61(2H, t), 2.84(5H, m) |  |
| 42 | 6 | 2-(2-chloro-4-fluoro-phenyl)-7-hydroxy-1H-benzoimidazole-4-carboxylic acid[4-(2-methanesulfonylamino-ethyl)-phenyl]-amide | N-[2-(4-amino-phenyl)-ethyl]ethanesulfonamide | 0 | δ 8.07(1H, m), 7.97(1H, d), 7.68–7.40(3H, m), 7.28–7.18(3H, m), 6.99(1H, d), 3.61(2H, t), 2.96(2H, q), 2.84(2H, t), 1.28(3H, t) |  |
| 43 | 7 | 2-(3-chloro-4-fluoro-phenyl)-7-hydroxy-1H-benzoimidazole-4-carboxylic acid{4-[2-(toluene-4-sulfonylamino)-ethyl]-phenyl}amide | N-[2-(4-amino-phenyl)-ethyl]-4-methyl-benzene-sulfonamide | 0 | δ 8.18(1H, d), 7.90(1H, m), 7.72(1H, d), 7.47(2H, d), 7.39(1H, m), 7.13–7.06(4H, m), 6.95(2H, d), 6.75(1H, d), 3.63(2H, t), 2.85(2H, t), 2.23(3H, s) |  |
| 44 | 7 | 2-(3-chloro-4-fluoro-phenyl)-7-hydroxy-1H-benzoimidazole-4-carboxylic acid{4-[2-methanesulfonylamino)-ethyl]-phenyl}amide | N-[2-(4-amino-phenyl)-ethyl]-ethanesulfonamide | 0 | δ 8.27(1H, d), 8.10(1H, m), 7.85(1H, d), 7.64(2H, d), 7.41(1H, t), 7.22(2H, d), 6.76(1H, d), 3.26(2H, t), 2.94(2H, q), 2.80(2H, t), 1.22(3H, t) |  |
| 45 | 7 | 2-(3-chloro-4-fluoro-phenyl)-7-hydroxy-1H-benzoimidazole-4-carboxylic acid[4-(2-methanesulfonylamino-ethyl)-phenyl]-amide | N-[2-(4-amino-phenyl)-ethyl]-methanesulfonamide | 0 | δ 8.31(1H, d), 8.12(1H, m), 7.91(1H, d), 7.68(2H, d), 7.47(1H, t), 7.26(2H, d), 6.83(1H, d), 3.31(2H, t), 2.85(5H, m) |  |

TABLE 2-continued

| Com No. | Pre No. | Chemical compound | $R^4N(CH_2)_nR^5$ | n | $^1H$ NMR(CH$_3$OH-d$_4$) | MW |
|---|---|---|---|---|---|---|
| 46 | 1 | cyclohexyl-(7-hydroxy-2-phenyl-1H-benzoimidazole-4-yl)-methanone | piperidine | 0 | δ 7.31–7.23(5H, m), 7.05(1H, d), 6.64(1H, d), 3.53–3.29(4H, m), 1.82–1.41(6H, m) | 320 |
| 47 | 2 | 2-(4-chloro-phenyl)-7-hydroxy-1H-benzoimidazole-4-carboxylic acid cyclohexyl-amide | piperidine | 0 | δ 8.10(2H, d), 7.88(1H, d), 7.66(2H, d), 6.92(1H, d), 3.53–3.29(4H, m), 1.82–1.41(6H, m) | 355 |
| 48 | 3 | 2-(2,4-dichloro-phenyl)-7-hydroxy-1H-benzoimidazole-4-yl-piperidine-1-yl-methanone | piperidine | 0 | δ 7.31–7.23(3H, m), 7.05(1H, d), 6.64(1H, d), 3.53–3.29(4H, m), 1.82–1.41(6H, m) | 389 |
| 49 | 1 | 7-hydroxy-2-phenyl-1H-benzoimidazole-4-carboxylic acid(4-nitro-benzyl)-amide | 4-nitrobenzylamine-hydrochloride) | 1 | δ 8.20(2H, d), 8.13(2H, d), 7.82(1H, d), 7.82–7.55(5H, m), 6.87(1H, d), 4.75(2H, s) | 388 |
| 50 | 1 | 7-hydroxy-2-phenyl-1H-benzoimidazole-4-carboxylic acid (4-amino-benzyl)-amide | 4-aminobenzylamine-dihydro chloride | 1 | δ 8.15(2H, d), 7.82(1H, d), 7.72–7.52(5H, m), 7.33(2H, d), 6.87(1H, d), 4.70(2H, s) | 358 |
| 51 | 1 | 7-hydroxy-2-phenyl-1H-benzoimidazole-4-carboxylic acid benzylamide | benzylamine | 1 | δ 8.10(2H, d), 7.87(1H, d), 7.85–7.60(3H, m), 7.40(2H, d), 7.39–7.28(2H, m), 7.27–7.20(1H, m), 6.89(1H, d), 4.66(2H, s) | 343 |
| 52 | 2 | 2-(4-chloro-phenyl)-7-hydroxy-1H-benzoimidazole-4-carboxylic acid benzylamide | benzylamine | 1 | δ 8.10(2H, d), 7.88(1H, d), 7.66(2H, d), 7.42–7.23(5H, m), 6.92(1H, d), 4.68(2H, s) | 377 |
| 53 | 2 | 2-(4-chloro-phenyl)-7-hydroxy-1H-benzoimidazole-4-carboxylic acid(4-nitro-benzyl)-amide | 4-nitrobenzylamine-hydrochloride | 1 | δ 8.20(2H, d), 7.90(2H, d), 7.88(1H, s), 7.69–7.51(4H, m), 6.91(1H, d), 4.76(2H, s) | 422 |
| 54 | 2 | 2-(4-chloro-phenyl)-7-hydroxy-1H-benzoimidazole-4-carboxylic acid(4-amino-benzyl)-amide | 4-aminobenzylamine-hydroxy chloride | 1 | δ 8.20(2H, d), 7.90(2H, d), 7.88(1H, s), 7.69–7.51(4H, m), 6.91(1H, d), 4.76(2H, s) | 392 |
| 55 | 3 | 2-(2,4-dichloro-phenyl)-7-hydroxy-1H-benzoimidazole-4-carboxylic acid benzylamide | benzylamine | 1 | δ 8.10(2H, d), 7.88(1H, d), 7.66(2H, d), 7.37–7.23(4H, m), 6.92(1H, d), 4.68(2H, s) | 411 |
| 56 | 3 | 2-(2,4-Dichloro-phenyl)-7-hydroxy-1H-benzoimidazole-4-carboxylic acid(4-nitro-benzyl)-amide | 4-nitrobenzylamine | 1 | δ 8.20(2H, d), 7.90(2H, t), 7.88(1H, s), 7.69–7.51(3H, m), 6.91(1H, d), 4.76(2H, s) | 456 |
| 57 | 1 | 7-hydroxy-2-phenyl-1H-benzoimidazole-4-carboxylic acid-phenethyl-amide | phenethylamine | 2 | δ 8.10(2H, d), 7.78(1H, d), 7.77–7.58(3H, m), 7.44–7.18(5H, m), 6.85(1H, s), 3.68(2H, t), 2.98(2H, t) | 357 |
| 58 | 1 | 7-hydroxy-2-phenyl-1H-benzoimidazole-4-carboxylic acid(4-hydroxy-pheneethyl)-amide | 4-hydroxyphenethylamine | 2 | δ 8.02–7.92(2H, m), 7.77(1H, d), 7.62–7.42(3H, m), 7.11(2H, d), 6.78(1H, d), 6.70(2H, d), 3.72(2H, t), 2.83(2H, t) | 373 |
| 59 | 1 | 7-hydroxy-2-phenyl-1H-benzoimidazole-4-carboxylic acid(4-nitro-phenethyl)-amide | 4-nitrophenethylamine | 2 | δ 8.10(2H, d), 8.01(2H, d), 7.75(1H, d), 7.69–7.52(3H, m), 7.50(2H, d), 6.85(1H, d), 3.75(2H, t), 3.08(2H, t) | 402 |
| 60 | 1 | 7-hydroxy-2-phenyl-1H-benzoimidazole-3-carboxylic acid(4-amino-phenethyl)-amino | 4-aminophenethylamine | 2 | δ 8.11(2H, d), 7.78(1H, d), 7.74–7.59(3H, m), 7.46(2H, d), 7.31(2H, d), 6.85(1H, d), 3.72(2H, t), 3.02(2H, t) | 372 |
| 61 | 1 | 7-hydroxy-2-phenyl-1H-benzoimidazole-3-carboxylic acid(2-amino-ethyl)-amide | ethylenediamine | 2 | δ 7.95–7.70(2H, m), 7.69(1H, d), 7.60–7.42(1H, m), 7.41–7.23(2H, m), 3.77(2H, t), 3.25(2H, t) | 296 |
| 62 | 1 | 7-hydroxy-2-phenyl-1H-benzoimidazole-3-carboxylic acid(4-hydroxy-3-methoxy-phenethyl)-amide | 4-hydroxy-3-methoxy-phenethylamine | 2 | δ 8.10–8.00(2H, m), 7.78(1H, d), 7.69–7.52(3H, m), 6.91–6.77(2H, m), 6.72(2H, d), 3.73(3H, s), 3.70(2H, t), 2.89(2H, t) | 403 |
| 63 | 1 | 7-hydroxy-2-phenyl-1H-benzoimidazole-4-carboxylic acid(3-hydroxy-4-methoxy-phenethyl)-amide | 3-hydroxy-4-methoxy-phenethylamine | 2 | δ 8.08–7.93(2H, m), 7.78(1H, d), 7.62–7.50(2H, m), 6.98–6.52(5H, m), 3.80(3H, s), 3.68(2H, t), 2.82(2H, t) | 403 |
| 64 | 1 | 7-hydroxy-2-phenyl-1H-benzoimidazole-4-carboxylic acid[2-(4-methanesulfonylamino-phenyl)-ethyl]-amide | N-[4-(2-amino-ethyl)-phenyl]-methane-sulfonamide | 2 | δ 8.07(1H, d), 7.77(1H, d), 7.65–7.61(4H, m), 7.28(2H, d), 7.18(2H, d), 6.85(1H, d), 3.71(2H, t), 2.95(2H, t), 2.85(3H, s) | 450 |
| 65 | 1 | 7-hydroxy-2-phenyl-1H-benzoimidazole-4-carboxylic acid{2-[4-(toluene-4-sulfonylamino)-phenyl]-ethyl}-amide | N-[4-(2-amino-ethyl)-phenyl]-4-methyl-benzenesulfonamide | 2 | δ 8.09(2H, d), 7.76–7.54(5H, m), 7.33–7.30(3H, m), 7.20–7.13(2H, m), 7.01–6.87(3H, m), 3.73(1H, t), 3.63(1H, t), 3.01(1H, t), 2.88(1H, t), 2.44(3H, s) | 526 |
| 66 | 1 | 7-hydroxy-2-phenyl-H-benzoimidazole-4-carboxylic acid(2-morpholin-4-yl-ethyl)-amide | 4-(2-aminoethyl)-morpholine | 2 | δ 8.17–8.12(2H, m), 7.88(1H, d), 7.77–7.71(3H, m), 7.00–6.95(1H, m), 4.02–3.75(4H, m), 3.89(2H, t), 3.47(2H, t), 3.46–3.00(4H, t) | 366 |
| 67 | 1 | 7-hydroxy-2-phenyl-1H-benzoimidazole-4-carboxylic acid{2-[4-(1,3-dioxo-1,3-dihydro-iso-indole-2-yl)-phenyl]-ethyl}-amide | 2-[4-(2-amino-ethyl)-phenyl]-isoindole-1,3-dione | 2 | δ 8.14(2H, d), 7.97–7.68(8H, m), 7.40(4H, dd), 6.93(1H, d), 3.74(2H, t), 3.05(2H, t) | 502 |

TABLE 2-continued

| Com No. | Pre No. | Chemical compound | $R^4N(CH_2)_nR^5$ | n | $^1$H NMR(CH$_3$OH-d$_4$) | MW |
|---|---|---|---|---|---|---|
| 68 | 1 | 7-hydroxy-2-phenyl-1H-benzo-imidazole-4-carboxylic acid[2-(4-ethanesulfonylamino-phenyl)-ethyl]-amide | N-[4-(2-amino-ethyl)-phenyl]-ethanesulfomamide | 2 | δ 8.15(2H, d), 7.79–7.72(4H, m), 7.22(4H, dd), 6.97(1H, d), 3.66(2H, t), 2.99(2H, q), 2.89(2H, t), 1.22(3H, t) | |
| 69 | 1 | 7-hydroxy-2-phenyl-1H-benzo-imidazole-4-carboxylic acid(5-mitropyridine-2-amino-ethyl)-amide | 2-(2-aminoethylamino)-5-nitropyridine | 2 | δ 8.84(1H, d), 8.13–8.05(3H, m), 7.80–7.65(4H, m), 6.90(1H, d), 6.57(1H, d), 3.71–3.60(4H, m) | 418 |
| 70 | 1 | 7-hydroxy-2-phenyl-1H-benzo-imidazole-4-carboxylic acid(2-pyridine-2-yl-ethyl)-amide | 2-(2-aminoethyl)-pyridine | 2 | 8.71(1H, d), 8.44(1H, t), 8.13–7.99(4H, m), 7.85(1H, t), 7.76–7.70(2H, m), 6.99(1H, d), 6.83(1H, d), 3.97(2H, t), 3.42(2H, t) | 358 |
| 71 | 2 | 2-(4-chloro-phenyl)-7-hydroxy-1H-benzoimidazole-4-carboxylic acid phenethyl amide | phenethylamine | 2 | δ 8.03(2H, d), 7.79(1H, d), 7.64(2H, m), 7.37–7.15(5H, m), 6.84(1H, d), 3.75(2H, t), 2.99(2H, t) | 391 |
| 72 | 2 | 2-(4-chloro-phenyl)-7-hydroxy-1H-benzoimidazole-4-carboxylic acid(4-nitro-phenethyl)-amide | 4-nitrophenethylamine | 2 | δ 8.18(2H, d), 8.05(2H, d), 7.80(1H, d), 7.64(2H, d), 7.56(2H, d), 6.88(1H, d), 3.80(2H, t), 3.11(2H, t) | 436 |
| 73 | 2 | 2-(4-chloro-phenyl)-7-hydroxy-1H-benzoimidazole-4-carboxylic acid(4-amino-phenethyl)-amide | 4-aminophenethylamine | 2 | δ 8.11(2H, d), 7.83(1H, d), 7.64(2H, d), 7.50(2H, d), 7.31(2H, d), 6.82(1H, d), 3.78(2H, t), 3.07(2H, t) | 406 |
| 74 | 2 | 2-(4-chloro-phenyl)-7-hydroxy-1H-benzoimidazole-4-carboxylic acid(4-hydroxy-phenethyl)-amide | 4-hydroxyphenethylamine | 2 | δ 7.82(1H, d), 7.73(2H, d), 7.65(2H, d), 7.12(2H, d), 7.00(1H, d), 6.86(1H, d), 6.74(1H, d), 3.71(2H, t), 2.87(2H, t) | 407 |
| 75 | 2 | 2-(4-chloro-phenyl)-7-hydroxy-1H-benzoimidazole-4-carboxylic acid[2-(4-methanesulfonyl-amino-phenyl)-ethyl]-amide | N-[4-(2-amino-ethyl-phenyl)-methane-sulfonamide | 2 | δ 8.08(2H, d), 7.79(1H, d), 7.69(2H, d), 7.29–7.16(4H, dd), 6.89(1H, d), 3.71(2H, t), 2.95(2H, t), 2.88(3H, s) | 484 |
| 76 | 2 | 2-(4-chloro-phenyl)-7-hydroxy-1H-benzoimidazole-4-carboxylic acid{2-[4-(toluene-4-sulfonylamino)-phenyl]-ethyl}-amine | N-[4-(2-amino-ethyl)-phenyl]-4-methyl-benzenesulfonamide | 2 | δ 8.08(2H, d), 7.77(1H, d), 7.69(2H, d), 7.55(1H, d), 7.15(3H, m), 6.98(2H, d), 6.88(1H, d), 3.65(2H, t), 2.86(2H, t), 2.31(3H, s) | 560 |
| 77 | 2 | 2-(4-chloro-phenyl)-7-hydroxy-1H-benzoimidazole-4-carboxylic acid(3-hydroxy-4-methoxy-phenethyl)-amide | 3-hydroxy-4-methoxy-phenethylamine | 2 | δ 8.10–7.37(3H, m), 7.36–6.43(6H, m), 3.72(3H, s), 3.70(2H, t), 2.81(2H, t) | 437 |
| 78 | 2 | 2-(4-chloro-phenyl)-7-hydroxy-1H-benzoimidazole-4-carboxylic acid(2-morpholin-4-yl-ethyl)-amide | 4-(2-aminoethyl) morpholine | 2 | δ 8.16(2H, d), 7.88(1H, d), 7.70(2H, d), 6.94(1H, d), 4.14–3.92(2H, m), 3.90(2H, t), 3.89–3.72(2H, m), 3.84–3.57(2H, m), 3.48(2H, t), 3.30–3.04(2H, m) | 400 |
| 79 | 2 | 2-(4-chloro-phenyl)-7-hydroxy-1H-benzoimidazole-4-carboxylic acid-2-[4-(1,3-dioxo-1,3-dihydro-isoindole-2-yl)-phenyl]-ethyl-amide | 2-[4-(2-amino-ethyl)-phenyl]-isoindole-1,3-dione | 2 | δ 8.10(2H, d), 7.91–7.85(4H, m), 7.80(1H, d), 7.68(2H, d), 6.98(1H, d), 7.40(4H, dd), 6.93(1H, m), 3.75(2H, t), 3.07(2H, t) | 536 |
| 80 | 2 | 2-(4-chloro-phenyl)-7-hydroxy-1H-benzoimidazole-4-carboxylic acid[2-(4-ethanesulfonyl-amino-phenyl)-ethyl]-amide | N-[4-(2-amino-ethyl-phenyl]-ethane-sulfonamide | 2 | δ 8.13–8.05(3H, m), 7.80–7.65(3H, m), 7.28–7.16(4H, m), 3.69(2H, t), 2.99(2H, q), 2.89(2H, t), 1.28(3H, t) | 498 |
| 81 | 2 | 2-(4-chloro-phenyl)-7-hydroxy-1H-benzoimidazole-4-carboxylic acid(5-nitropyridine-2-amino-ethyl)-amide | 2-(2-aminoethylamino)-5-nitropyridine | 2 | δ 8.83(1H, d), 8.11–8.05(1H, m), 7.86–7.81(3H, m), 7.68–7.60(2H, m), 6.90(1H, d), 6.60–6.54(1H, m), 3.71–3.60(4H, m) | 452 |
| 82 | 2 | 2-(4-chloro-phenyl)-7-hydroxy-1H-benzoimidazole-4-carboxylic acid(2-pyridine-2-yl-ethyl)-amide | 2-(2-aminoethyl)-pyridine | 2 | δ 8.70(1H, d), 8.43(1H, t), 8.13–8.09(3H, m), 8.01(1H, d), 7.94(1H, d), 7.77(1H, d), 7.61(2H, d), 4.01(2H, t), 3.42(2H, t) | 392 |
| 83 | 2 | 2-(4-chloro-phenyl)-7-hydroxy-1H-benzoimidazole-4-carboxylic acid[2-(1H-imidazol-4-yl)-ethyl]amine | histamine | 2 | δ 8.81(s, 1H), 8.12(d, 2H), 7.80(d, 1H), 7.65(d, 2H), 7.40(s, 1H), 6.83(d, 1H), 3.84(t, 2H), 3.12(t, 2H) | |
| 84 | 2 | 2-(4-chloro-phenyl)-7-hydroxy-1H-benzoimidazole-4-carboxylic acid[2-(4-hydroxy-phenyl)-ethyl]-amide | 4-hydroxyphenethylamine | 2 | δ 8.05(d, 2H), 7.79(d, 1H), 7.65(d, 2H), 7.12(d, 2H), 6.85(d, 1H), 6.72(d, 2H), 3.70(t, 2H), 2.87(t, 2H) | |
| 85 | 2 | 2-(4-Chloro-phenyl)-7-hydroxy-1H-benzoimidazole-4-carboxylic acid[2-(5-acetylamino-pyridin-2-ylamino)-ethyl]-amide | 4-acetyl-2-pyridiylethyl amine | 2 | δ 8.57(s, 1H), 8.20~8.00(m, 3H), 8.02(br, 1H), 7.75~7.60(m, 3H), 7.38(d, 1H), 6.88(d, 1H), 4.12(t, 2H), 3.68(t, 2H), 2.12(s, 3H) | |
| 86 | 2 | 2-(4-chloro-phenyl)-7-hydroxy-1H-benzoimidazole-4-carboxylic acid(2-{4-[2-(4-methyl-piperazin-1-yl)-acetyl-amino]-phenyl}-ethyl)-amide | N-[4-(2-amino-ethyl)-phenyl]-2-(4-methyl-piperazin-1-yl)-acetamide | 2 | δ 8.03(m, 2H), 7.80(d, 1H), 7.60(d, 2H), 7.57(d, 2H), 7.29(d, 2H), 6.83(d, 1H), 3.75(t, 2H), 3.34(s, 2H), 3.10~2.75(m, 13H) | |

TABLE 2-continued

| Com No. | Pre No. | Chemical compound | R⁴N(CH₂)ₙR⁵ | n | ¹H NMR(CH₃OH-d₄) | MW |
|---|---|---|---|---|---|---|
| 87 | 2 | 2-(4-chloro-phenyl)-7-hydroxy-1H-benzoimidazole-4-carboxylic acid(2-{4-[2-(4-ethyl-piperazin-1-yl)-acetylamino]-phenyl}-ethyl)-amide | N-[4-(2-amino-ethyl)-phenyl]-2-(4-ethyl-piperazin-1-yl)-acetamide | 2 | δ 8.03(m, 2H), 7.79(d, 1H), 7.61(d, 2H), 7.53(d, 2H), 7.29(d, 2H), 6.84(d, 1H), 3.75(t, 2H), 3.34(s, 2H), 3.25(q, 2H), 3.05~2.75(m, 8H), 1.35(t, 3H) | |
| 88 | 2 | 2-(4-chloro-phenyl)-7-hydroxy-1H-benzoimidazole-4-carboxylic acid{2-[4-(2-dimethylamino-acetylamino)-phenyl]-ethyl}-amide | N-[4-(2-amino-ethyl)-phenyl]-2-dimethyl-amino-acetamide | 2 | δ 8.03(d, 2H), 7.80(d, 1H), 7.60(d, 2H), 7.54(t, 2H), 7.32(d, 2H), 6.81(d, 1H), 4.08(s, 2H), 3.76(t, 2H), 2.95(m, 8H) | |
| 89 | 2 | 2-(4-chloro-phenyl)-7-hydroxy-1H-benzoimidazole-4-carboxylic acid{2-[4-(2-diethylamino-acetylamino)-phenyl]-ethyl}-amide | N-[4-(2-amino-ethyl)-phenyl]-2-diethylamino-acetamide | 2 | δ 8.02(d, 2H), 7.80(d, 1H), 7.60(d, 2H), 7.54(d, 2H), 7.32(d, 2H), 6.81(d, 1H), 4.06(s, 2H), 3.77(t, 2H), 3.32(q, 4H), 2.99(t, 2H), 1.35(t, 6H) | |
| 90 | 2 | 2-(4-chloro-phenyl)-7-hydroxy-1H-benzoimidazole-4-carboxylic acid[2-(4-amino-phenyl)-ethyl]-amide | 4-aminophenethylamine | 2 | δ 8.13(d, 2H), 7.78(d, 1H), 7.62(d, 2H), 7.51(d, 2H), 7.29(d, 2H), 6.77(d, 1H), 3.79(t, 2H), 3.69(t, 2H | |
| 91 | 2 | 2-(4-chloro-phenyl)-7-hydroxy-1H-benzoimidazole-4-carboxylic acid[2-(5-amino-pyridin-2-ylamino)-ethyl]-amide | N-(2-amino-ethyl)-pyridine-2,5-diamine | 2 | δ 8.73(s, 1H), 8.22(d, 1H), 8.09(d, 1H), 7.88(m, 2H), 7.60(d, 1H), 7.47(d, 1H), 7.13(d, 1H), 6.78(m, 1H), 3.87(t, 2H), 3.75(t, 2H) | |
| 92 | 2 | 2-(4-chloro-phenyl)-7-hydroxy-1H-benzoimidazole-4-carboxylic acid{2-[4-(2-morpholin-4-yl-acetylamino)-phenyl]-ethyl}-amide | N-[4-(2-amino-ethyl)-phenyl]-2-morpholin-4-yl-acetamide | 2 | δ 8.03(d, 2H), 7.80(d, 1H), 7.60(d, 2H), 7.54(d, 2H), 7.31(d, 2H), 6.81(d, 1H), 3.12(s, 2H), 3.98(br, 4H), 3.77(t, 2H), 3.44(br, 4H), 2,98(t, 2H) | |
| 93 | 2 | 2-(4-chloro-phenyl)-7-hydroxy-1H-benzoimidazole-4-carboxylic acid[2-(4-dimethylamino-phenyl)-ethyl]-amide | N,N-(dimethylamino)-phenethylamine | 2 | δ 8.13(d, 2H), 7.78(d, 1H), 7.62(d, 2H), 7.51(d, 2H), 7.29(d, 1H), 6.77(d, 1H), 3.81(t, 2H), 3.15(s, 6H), 3.08(t, 2H) | |
| 94 | 2 | 2-(4-chloro-phenyl)-7-hydroxy-1H-benzoimidazole-4-carboxylic acid{2-[4-(2-morpholin-4-yl-ethoxy)phenyl]-ethyl}-amide | 2-[4-(2-morpholin-4-yl-ethoxy)-phenyl]-ethylamine | 2 | δ 8.06(d, 2H), 7.79(d, 1H), 7.73(d, 2H), 7.28(d, 2H), 6.94(d, 2H), 6.83(d, 1H), 4.31(m, 2H), 3.99(br, 2H), 3.95~3.65(m, 4H), 3.65~3.50(m, 4H), 3.32(m, 2H), 2.95(m, 2H) | |
| 95 | 2 | 2-(4-chloro-phenyl)-7-hydroxy-1H-benzoimidazole-4-carboxylic acid(2-{4-]2-(4-methyl-piperazin-1-yl)ethoxy]-phenyl}-ethyl)-amide | 2-{4-[2-(4-methyl-piperazin-1-yl)-ethoxy]-phenyl}-ethylamine | 2 | δ 8.17(d, 2H), 7.78(d, 1H), 7.40(t, 2H), 7.23(d, 2H), 6.90(m, 3H), 4.25(t, 2H), 3.67(t, 2H), 3.50~3.30(m, 10H), 2.90(m, 5H) | |
| 96 | 2 | 2-(4-chloro-phenyl)-7-hydroxy-1H-benzoimidazole-4-carboxylic acid[2-(2-hydroxy-phenyl)-ethyl]-amide | 2-hydroxyphenethyl-amine | 2 | δ 8.05(d, 2H), 7.79(d, 1H), 7.62(d, 2H), 7.18(d, 1H), 07.05(d, 1H), 6.90~6.70(m, 3H), 3.70(t, 2H), 3.02(t, 2H) | |
| 97 | 2 | 2-(4-chloro-phenyl)-7-hydroxy-1H-benzoimidazole-4-carboxylic acid[2-(2-methoxy-phenyl)-ethyl]-amide | 2-methoxyphenethylamine | 2 | δ 8.00(d, 2H), 7.81(d, 1H), 7.57(d, 2H), 7.24(d, 1H), 6.95(m, 1H), 6.85(m, 1H), 6.73(d, 2H), 3.76(s, 3H), 3.64(t, 2H), 2.98(t, 2H) | |
| 98 | 2 | 2-(4-chloro-phenyl)-7-hydroxy-1H-benzoimidazole-4-carboxylic acid[2-(3-bromo-phenyl)-ethyl]-amide | 3-bromophenethylamine | 2 | δ 8.00(d, 2H), 7.79(d, 1H), 7.02~7.50(m, 3H), 7.40~7.20(m, 3H), 6.74(d, 1H), 3.81(t, 2H), 3.01(t, 2H) | |
| 99 | 3 | 2-(2,4-dichloro-phenyl)-7-hydroxy-1H-benzoimidazole-4-carboxylic acid phenethyl-amide | phenethylamine | 2 | δ 7.92–7.66(3H, m), 7.65–7.38(1H, m), 7.37–7.00(5H, m), 7.44–7.18(5H, m), 6.85(1H, d), 3.68(2H, t), 2.98(2H, t) | 425 |
| 100 | 3 | 2-(2,4-dichloro-phenyl)-7-hydroxy-1H-benzoimidazole-4-carboxylic acid(4-amino-phenethyl)-amide | 4-nitrophenethylamine | 2 | δ 8.08(2H, d), 7.90–7.31(5H, m), 7.20–6.97(1H, m), 6.82(1H, d), 3.76(2H, t), 3.09(2H, t) | 470 |
| 101 | 3 | 2-(2,4-dichloro-phenyl)-7-hydroxy-1H-benzoimidazole-4-carboxylic acid(4-hydroxy-3-methoxy-phenethyl)-amide | 4-hydroxy-3-methoxy-phenethylamine | 2 | δ 7.95–7.68(3H, m), 7.67–7.40(2H, m), 7.20–6.92(1H, m), 6.82(2H, d), 6.68(1H, d), 3.72(2H, t), 3.60(3H, s), 2.88(2H, t) | 471 |
| 102 | 3 | 2-(2,4-dichloro-phenyl)-7-hydroxy-1H-benzoimidazole-4-carboxylic acid(3-hydroxy-4-methoxy-phenethyl)-amide | 3-hydroxy-4-methoxy-phenethylamine | 2 | δ 8.10–7.37(3H, m), 7.36–6.43(6H, m), 3.72(3H, s), 3.70(2H, t), 2.81(2H, t) | 471 |
| 103 | 3 | 2-(2,4-dichloro-phenyl)-7-hydroxy-1H-benzoimidazole-4-carboxylic acid(2-amino-ethyl)-amide | ethylenediamine | 2 | δ 8.10(2H, d), 7.88(1H, d), 7.66(2H, d), 7.37–7.23(4H, m), 6.92(1H, d), 3.77(2H, t), 3.25(2H, t) | 364 |
| 104 | 3 | 2-(2,4-dichloro-phenyl)-7-hydroxy-1H-benzoimidazole-4-carboxylic acid(4-hydroxy-phenethyl)-amide | 4-hydroxyphen-ethylamine | 2 | δ 7.94–7.64(3H, m), 7.62–7.39(1H, m), 7.28–6.97(3H, m), 6.96–6.78(1H, m), 6.68(1H, d), 3.64(2H, t), 2.82(2H, t) | 441 |

TABLE 2-continued

| Com No. | Pre No. | Chemical compound | $R^4N(CH_2)_nR^5$ | n | $^1$H NMR(CH$_3$OH-d$_4$) | MW |
|---|---|---|---|---|---|---|
| 105 | 3 | 2-(2,4-dichloro-phenyl)-7-hydroxy-1H-benzoimidazole-4-carboxylic acid{2-[4-(toluene-4-sulfonylamino)-phenyl]-ethyl}-amide | N-[4-(2-amino-ethyl)-phemphenyl]-4-methyl-benzenesulfonamide | 2 | δ 7.95–7.70(2H, m), 7.69–7.43(3H, m), 7.42–7.23(3H, m), 7.22–7.03(2H, m), 7.01(1H, d), 6.98–6.77(2H, m), 3.81–3.52(2H, m), 3.10–2.73(2H, m), 3.01(1H, t), 2.88(1H, t), 2.48(3H, s) | 594 |
| 106 | 3 | 2-(2,4-dichloro-phenyl)-7-hydroxy-1H-benzoimidazole-4-carboxylic acid[2-(4-methane-sulfonylamino-phenyl)-ethyl]-amide | N-[4-(2-amino-ethyl)-phenyl]-methane sulfonamide | 2 | δ 7.92–7.78(3H, m), 7.68(1H, d), 7.24(4H, dd), 6.96(1H, d), 3.68(2H, t), 2.93(2H, t), 2,90(3H, s) | 518 |
| 107 | 3 | 2-(2,4-dichloro-phenyl)-7-hydroxy-1H-benzoimidazole-4-carboxylic acid{2-[4-(1,3-dioxo-1,3-dihydro-isoindole-2-yl)-phenyl]-ethyl}-amide | 2-[4-(2-amino-ethyl)-phenyl]-isoindole-1,3-dione | 2 | δ 7.92–7.83(7H, m), 7.67(1H, d), 7.38(4H, dd), 6.98(1H, d), 3.72(2H, t), 3.05(2H, t) | 570 |
| 108 | 3 | 2-(2,4-dichloro-phenyl)-7-hydroxy-1H-benzoimidazole-4-carboxylic acid(2-morpholin-4-yl-ethyl)-amide | 4-(2-aminoethyl)-morpholine | 2 | δ 8.02–7.80(3H, m), 7.65(1H, d), 6.98(1H, d), 4.14–3.92(2H, m), 3.88(2H, m), 3.89–3.72(2H, m), 3.84–3.57(2H, m), 3.44(2H, t), 3.30–3.04(2H, m) | 434 |
| 109 | 3 | 2-(2,4-dichloro-phenyl)-7-hydroxy-1H-benzoimidazole-4-carboxylic acid[2-(4-ethanesulfonylamino-phenyl)-ethyl]-amide | N-[4-(2-amino-ethyl)-phenyl]-ethanesulfonamide | 2 | δ 7.91–7.75(3H, m), 7.68(1H, d), 7.21(4H, dd), 6.99(1H, d), 3.66(2H, t), 2.99(2H, q), 2.89(2H, t), 1.28(3H, t) | 532 |
| 110 | 3 | 2-(2,4-dichloro-phenyl)-7-hydroxy-1H-benzoimidazole-4-carboxylic acid(5-nitropyridine-2-amino-ethyl)-amide | 2-(2-aminoethylamino)-5-nitropyridine | 2 | δ 8.83(1H, d), 8.11–8.05(1H, m), 7.86–7.81(3H, m), 7.68–7.60(1H, m), 6.90(1H, d), 6.60–6.54(1H, d), 3.71–3.60(4H, m) | 486 |
| 111 | 3 | 2-(2,4-dichloro-phenyl)-7-hydroxy-1H-benzoimidazole-4-carboxylic acid(2-pyridin-2-yl-ethyl)-amide | 2-(2-aminoethyl)-pyridine | 2 | δ 8.70(1H, d), 8.40(1H, t), 8.07–7.50(6H, m), 6.83(1H, d), 3.95(2H, t), 3.38(2H, t) | 426 |
| 112 | 3 | 2-(2,4-dichloro-phenyl)-7-hydroxy-1H-benzoimidazole-4-carboxylic acid[2-(4-acetyl-amino-phenyl)-ethyl]-amide | 4-(acetylamino)phen-ethylamine | 2 | δ 7.85~7.78(m, 3H), 7.61(d, 1H), 7.25(d, 2H), 7.15(d, 2H), 6.86(d, 1H), 3.69(t, 2H), 2.95(t, 2H), 2.88(s, 3H) | |
| 113 | 3 | 2-(2,4-dichloro-phenyl)-7-hydroxy-1H-benzoimidazole-4-carboxylic acid[2-(4-pentanoyl-amino-phenyl)ethyl]-amide | 4-(pentanoylamino)-phenethylamine | 2 | δ 7.90~7.80(m, 3H), 7.72(d, 1H), 7.61(d, 2H), 7.20(d, 2H), 6.89(d, 1H), 3.68(t, 2H), 2.89(t, 2H), 2.35(t, 2H), 1.65(m, 2H), 1.38(m, 2H), 0.96(t, 3H) | |
| 114 | 4 | 2-(4-fluoro-phenyl)-7-hydroxy-1H-benzoimidazole-4-carboxylic acid[2-(4-methane-sulfonylamino-phenyl)-ethyl]-amide | N-[4-(2-amino-ethyl)-phenyl]-methane-sulfonamide | 2 | δ 8.15–8.10(m, 2H), 7.78(1H, d), 7.46(2H, t), 7.27(2H, d), 7.18(2H, d), 6.87(1H, d), 3.70(2H, t), 2.97(2H, t), 2.87(3H, s) | |
| 115 | 4 | 2-(4-fluoro-phenyl)-7-hydroxy-1H-benzoimidazole-4-carboxylic acid{2-[4-(toluene-4-sulfonylamino)phenyl]-ethyl}-amide | N-[4-(2-amino-ethyl)-phenyl]-p-toluene-sulfonamide | 2 | | |
| 116 | 4 | 2-(4-fluoro-phenyl)-7-hydroxy-1H-benzoimidazole-4-carboxylic acid[2-(4-ethane-sulfonylamino-phenyl)-ethyl]-amide | N-[4-(2-amino-ethyl)-phenyl]-ethane-sulfonamide | 2 | δ 8.17(2H, m), 7.77(1H, d), 7.44(2H, t), 7.25(2H, d), 7.17(2H, d), 6.92(1H, d), 3.67(2H, t), 3.02(2H, q), 2.96(2H, t), 1.26(3H, t) | |
| 117 | 4 | 2-(4-fluoro-phenyl)-7-hydroxy-1H-benzoimidazole-4-carboxylic acid[2-(4-acetyl-amino-phenyl)-ethyl]-amide | N-[4-(2-amino-ethyl)-phenyl]-acetamide | 2 | δ 8.1~8.2(m, 2H), 7.58(d, 1H), 7.44(m, 4H), 7.34(m, 2H), 6.92(d, 1H), 3.66(2H, t), 2.90(t, 2H), 2.09(s, 1H) | |
| 118 | 4 | 2-(4-fluoro-phenyl)-7-hydroxy-1H-benzoimidazole-4-carboxylic acid[2-(4-methyl-piperazin-1-yl)-ethyl]-amide | 2-(4-methyl-piperazin-1-yl)-ethylamine | 2 | δ 8.25~8.16(m, 2H), 8.05(d, 1H), 7.48~7.37(m, 2H), 6.88(d, 1H), 3.70~3.50(m, 10H), 3.14(t, 2H), 2.96(s, 3H), 2.12(t, 2H) | |
| 119 | 4 | 2-(4-fluoro-phenyl)-7-hydroxy-1H-benzoimidazole-4-carboxylic acid(2-morpholin-4-yl-ethyl)-amide | 2-morpholin-4-yl-ethylamine | 2 | δ 8.22(m, 2H), 7.85(d, 1H), 7.41(t, 2H), 6.90(d, 1H), 4.20~3.60(m, 8H), 3.48(t, 2H), 3.34~3.10(br, 2H) | |
| 120 | 4 | 2-(4-fluoro-phenyl)-7-hydroxy-1H-benzoimidazole-4-carboxylic acid[2-(4-pentanoyl-amino-phenyl)-ethyl]-amide | pentanoic acid [4-(2-amino-ethyl)-phenyl]-amide | 2 | δ 8.08(m, 2H), 7.74(d, 1H), 7.45( d, 2H), 7.35(t, 2H), 7.18(d, 2H), 6.86(d, 1H), 3.66(t, 2H), 2.86(t, 2H), 2.33(t, 2H), 1.64(m, 2H), 1.39(m, 2H), 0.93(t, 3H) | |
| 121 | 4 | 2-(4-fluoro-phenyl)-7-hydroxy-1H-benzoimidazole-4-carboxylic acid[2-(4-hydroxy-phenyl)-ethyl]-amide | 4-hydroxyphenethylamine | 2 | δ 8.14(m, 2H), 7.78(d, 1H), 7.44(t, 2H), 7.09(d, 2H), 6.89(d, 1H), 6.72(d, 2H), 3.66(t, 2H), 2.86(t, 2H) | |

TABLE 2-continued

| Com No. | Pre No. | Chemical compound | R⁴N(CH₂)ₙR⁵ | n | ¹H NMR(CH₃OH-d₄) | MW |
|---|---|---|---|---|---|---|
| 122 | 4 | 2-(4-fluoro-phenyl)-7-hydroxy-1H-benzoimidazole-4-carboxylic acid[2-(5-nitro-pyridin-2-ylamino)-ethyl]-amide | N-(4-nitro-pyridin-2-yl)-ethane-1,2-diamine | 2 | δ 8.84(s, 1H), 8.21~8.17(m, 3H), 7.79(d, 1H), 7.44(t, 2H), 6.92(d, 1H), 6.63(br, 1H), 3.90~3.60(m, 4H) | |
| 123 | 4 | 2-(4-fluoro-phenyl)-7-hydroxy-1H-benzoimidazole-4-carboxylic acid[2-(5-methane-sulfonylamino-pyridin-2-ylamino)-ethyl]-amide | N-[6-(2-Amino-ethyl-amino)-pyridin-3-yl]-methanesulfonamide | 2 | δ 8.24~8.19(m, 2H), 7.95~7.75(m, 3H), 7.43(t, 2H), 7.15(d, 1H), 6.92(d, 1H), 3.80~3.65(m, 4H), 2.99(t, 3H) | |
| 124 | 4 | 2-(4-fluoro-phenyl)-7-hydroxy-1H-benzoimidazole-4-carboxylic acid{2-[5-(toluene-4-sulfonylamino)-pyridin-2-ylamino]-ethyl}-amide | N-[6-(2-amino-ethylamino)-pyridin-3-yl]-p-toluenesulfonamide | 2 | δ 8.23(m, 2H), 7.81(d, 1H), 7.52(m, 4H), 7.40~7.20(m, 4H), 7.01(d, 1H), 6.82(d, 1H), 3.75(t, 2H), 3.66(t, 2H), 2.36(s, 3H) | |
| 125 | 4 | 2-(4-fluoro-phenyl)-7-hydroxy-1H-benzoimidazole-4-carboxylic acid[2-(1H-imidazol-4-yl)-ethyl]-amide | histamine | 2 | δ 8.81(s, 1H), 8.19(m, 2H), 7.80(d, 1H), 7.50~7.30(m, 3H), 6.90(d, 1H), 3.80(t, 2H), 3.11(t, 2H) | |
| 126 | 4 | 2-(4-fluoro-phenyl)-7-hydroxy-1H-benzoimidazole-4-carboxylic acid[2-(5-acetyl-amino-pyridin-2-yl-amino)-ethyl]-amide | N-[6-(2-amino-ethylamino)-pyridin-3-yl]-acetamide | 2 | δ 8.58(s, 1H), 8.22(m, 2H), 8.04(br, 1H), 7.69(d, 1H), 7.50~7.35(m, 3H), 6.90(d, 1H), 4.11(t, 2H), 3.69(t, 2H), 2.11(s, 3H) | |
| 127 | 4 | 2-(4-fluoro-phenyl)-7-hydroxy-1H-benzoimidazole-4-carboxylic acid(2-{4-[2-(4-methyl-piperazin-1-yl)-acetyl-amino]-phenyl}-ethyl)-amide | N-[4-(2-amino-ethyl)-phenyl]-2-(4-methyl-piperazin-1-yl)-acetamide | 2 | δ 8.10~7.80(m, 2H), 7.69(d, 1H), 7.43(d, 2H), 7.25(t, 2H), 7.19(d, 2H), 6.76(d, 1H), 3.63(t, 2H), 3.21(s, 2H), 2.90~2.78(m, 13H) | |
| 128 | 4 | 2-(4-fluoro-phenyl)-7-hydroxy-1H-benzoimidazole-4-carboxylic acid(2-{4-[2-(4-ethyl-piperazin-1-yl)-acetyl-amino]-phenyl}-ethyl)-amide | N-[4-(2-amino-ethyl)-phenyl]-2-(4-ethyl-piperazin-1-yl)-acetamide | 2 | δ 8.13(m, 2H), 7.79(d, 1H), 7.52(d, 2H), 7.37(t, 2H), 7.27(d, 2H), 6.85(d, 1H), 3.72(t, 2H), 3.30(s, 2H), 3.24(q, 4H), 3.05~2.85(m, 10H), 1.35(t, 3H) | |
| 129 | 4 | 2-(4-fluoro-phenyl)-7-hydroxy-1H-benzoimidazole-4-carboxylic acid{2-[4-(2-dimethylamino-acetylamino)-phenyl]-ethyl}-amide | N-[4-(2-amino-ethyl)-phenyl]-2-dimethyl-amino-acetamide | 2 | δ 8.11(m, 2H), 7.78(d, 1H), 7.53(d, 2H), 7.40~7.25(m, 4H), 6.83(d, 1H), 4.09(s, 2H), 3.74(t, 2H), 2.94(m, 8H) | |
| 130 | 4 | 2-(4-fluoro-phenyl)-7-hydroxy-1H-benzoimidazole-4-carboxylic acid{2-[4-(2-diethylamino-acetylamino)-phenyl]-ethyl}-amide | N-[4-(2-amino-ethyl)-phenyl]-2-diethyl-amino-acetamide | 2 | δ 8.13(m, 2H), 7.79(d, 1H), 7.54(d, 2H), 7.39(t, 2H), 7.30(d, 2H), 6.86(d, 1H), 4.08(s, 2H), 3.72(t, 2H), 3.33(q, 4H), 2.96(t, 2H), 1.35(t, 6H) | |
| 131 | 4 | 2-(4-fluoro-phenyl)-7-hydroxy-1H-benzoimidazole-4-carboxylic acid[2-(4-amino-phenyl)-ethyl]-amide | 4-aminophenethylamine | 2 | δ 8.20(m, 2H), 7.79(d, 1H), 7.49(d, 2H), 7.42(t, 2H), 7.32(d, 2H), 6.86(d, 1H), 3.74(t, 2H), 3.06(t, 2H) | |
| 132 | 4 | 2-(4-fluoro-phenyl)-7-hydroxy-1H-benzoimidazole-4-carboxylic acid[2-(4-morpholin-4-yl-phenyl)-ethyl]-amide | 2-(4-morpholin-4-yl-phenyl)-ethylamine | 2 | δ 8.14(m, 2H), 7.78(d, 1H), 7.41(d, 2H), 7.35(d, 1H), 7.14(d, 2H), 6.85(d, 1H), 3.89(m, 4H), 3.71(t, 2H), 3.28(m, 4H), 2.96(t, 2H) | |
| 133 | 4 | 2-(4-fluoro-phenyl)-7-hydroxy-1H-benzoimidazole-4-carboxylic acid{2-[4-(3-diethylamino-pyrrolidin-1-yl)-phenyl]-ethyl}-amide | {1-[4-(2-amino-ethyl)-phenyl]-pyrrolidin-3-yl}-diethyl-amine | 2 | δ 8.13(m, 1H), 7.78(d, 1H), 7.32~7.20(m, 4H), 7.11(s, 1H), 6.74(m, 2H), 6.48(d, 1H), 3.60(t, 2H), 2.90(t, 2H), 2.82~2.71(m, 6H), 2.40(q, 4H), 1.65(m, 1H), 1.02(t, 6H) | |
| 134 | 4 | 2-(4-fluoro-phenyl)-7-hydroxy-1H-benzoimidazole-4-carboxylic acid{2-[4-(2-morpholin-4-yl-acetylamino)-phenyl]-ethyl}-amide | N-[4-(2-amino-ethyl)-phenyl]-2-morpholin-4-yl-acetamide | 2 | δ 8.15(m, 2H), 7.79(d, 1H), 7.53(d, 2H), 7.39(t, 2H), 7.29(d, 2H), 6.87(d, 1H), 4.13(s, 2H), 3.97(br, 4H), 3.72(q, 2H), 3.44(br, 4H), 2.97(t, 2H) | |
| 135 | 4 | 2-(4-fluoro-phenyl)-7-hydroxy-1H-benzoimidazole-4-carboxylic acid[2-(4-dimethyl-amino-phenyl)-ethyl]-amide | N,N-(dimethylamino)-phenethylamine | 2 | δ 8.20(m, 3H), 7.78(d, 1H), 7.54(m, 3H), 7.43(t, 2H), 6.84(d, 1H), 3.75(t, 2H), 3.21(s, 6H), 3.07(t, 2H) | |
| 136 | 4 | 2-(4-fluoro-phenyl)-7-hydroxy-1H-benzoimidazole-4-carboxylic acid{2-[4-(2-morpholin-4-yl-ethoxy)-phenyl]-ethyl}-amide | 2-[4-(2-morpholin-4-yl-ethoxy)phenyl]-ethylamine | 2 | δ 8.18(m, 2H), 7.79(d, 1H), 7.42(t, 2H), 7.26(d, 2H), 7.00~6.85(m, 3H), 4.33(m, 2H), 4.10~4.00(br, 2H), 3.95~3.75(br, 2H), 3.75~3.50(m, 8H), 3.32(m, 4H), 2.95(m, 2H) | |
| 137 | 4 | 2-(4-fluoro-phenyl)-7-hydroxy-1H-benzoimidazole-4-carboxylic acid[2-(2-hydroxy-phenyl)-ethyl]-amide | 2-hydroxyphenethylamine | 2 | δ 8.18(m, 2H), 7.78(d, 1H), 7.38(t, 2H), 7.14(d, 1H), 7.03(d, 1H), 6.88~6.74(m, 3H), 3.77(t, 2H), 2.98(t, 2H) | |

TABLE 2-continued

| Com No. | Pre No. | Chemical compound | $R^4N(CH_2)_nR^5$ | n | $^1$H NMR(CH$_3$OH-d$_4$) | MW |
|---|---|---|---|---|---|---|
| 138 | 4 | 2-(4-fluoro-phenyl)-7-hydroxy-1H-benzoimidazole-4-carboxylic acid[2-(2-methoxy-phenyl)-ethyl]-amide | 2-methoxyphen-ethylamine | 2 | δ 8.18~8.05(m, 2H), 7.78(d, 1H), 7.45~7.25(m, 3H), 7.20(m, 2H), 6.95(d, 1H), 6.82(d, 1H), 3.78(s, 3H), 3.73(t, 2H), 2.99(t, 2H) | |
| 139 | 4 | 2-(4-fluoro-phenyl)-7-hydroxy-1H-benzoimidazole-4-carboxylic acid[2-(3-bromo-phenyl)-ethyl]-amide | 3-bromophenethylamine | 2 | δ 8.12(m, 2H), 7.80(d, 1H), 7.49(s, 1H), 7.38~7.18(m, 5H), 6.83(d, 1H), 3.76(t, 2H), 2.97(t, 2H) | |
| 140 | 5 | 2-(2,4-difluoro-phenyl)-7-hydroxy-1H-benzoimidazole-4-carboxylic acid[2-(4-methane-sulfonylamino-phenyl)-ethyl]-amide | N-[4-(2-amino-ethyl)-phenyl]-methane-sulfonamide | 2 | δ 7.92–7.89(1H, m), 7.74(1H, m), 7.30–7.11(6H, m), 6.74(1H, d), 3.67(2H, bs), 2.89(2H, bs), 2.82(3H, s) | |
| 141 | 5 | 2-(2,4-difluoro-phenyl)-7-hydroxy-1H-benzoimidazole-4-carboxylic acid{2-[4-(toluene-4-sulfonylamino)-phenyl]-ethyl}amide | N-[4-(2-amino-ethyl)-phenyl]-p-toluene-sulfonamide | 2 | δ 7.99(1H, m), 7.74(1H, d), 7.50(2H, d), 7.33–7.26(2H, m), 7.23(4H, m), 6.94(2H, d), 6.81(1H, d), 3.58(2H, t), 2.82(2H, t), 2.23(3H, s) | |
| 142 | 5 | 2-(2,4-difluoro-phenyl)-7-hydroxy-1H-benzoimidazole-4-carboxylic acid[2-(4-ethane-sulfonylamino-phenyl)-ethyl]-amide | N-[4-(2-amino-ethyl)-phenyl]-ethanesulfonamide | 2 | δ 8.06(1H, d), 7.81(1H, d), 7.51–7.15(6H, m), 6.88(1H, d), 3.67(2H, t), 3.01(2H, q), 2.92(2H, t), 1.25(3H, m) | |
| 143 | 6 | 2-(2-chloro-4-fluoro-phenyl)-7-hydroxy-1H-benzoimidazole-4-carboxylic acid[2-(4-methane-sulfonylamino-phenyl)-ethyl]-amide | N-[4-(2-amino-ethyl)-phenyl]-methane-sulfonamide | 2 | δ 7.94(1H, m), 7.84(1H, m), 7.62(1H, m), 7.43(2H, m), 7.38–7.24(3H, m), 6.95(1H, d), 3.65(2H, t), 2.99–2.83(5H, m) | |
| 144 | 6 | 2-(2-chloro-4-fluoro-phenyl)-7-hydroxy-1H-benzoimidazole-4-carboxylic acid{2-[4-toluene-4-sulfonylamino)-phenyl]-ethyl}amide | N-[4-(2-amino-ethyl)-phenyl]-p-toluene-sulfonamide | 2 | δ 7.91(1H, m), 7.81(1H, d), 7.62–7.54(3H, m), 7.42(1H, m), 7.20–7.11(4H, m), 7.05–6.93(3H, m), 3.61(2H, t), 2.86(2H, t), 2.32(3H, s) | |
| 145 | 6 | 2-(2-chloro-4-fluoro-phenyl)-7-hydroxy-1H-benzoimidazole-4-carboxylic acid[2-(4-ethanesulfonylamino-phenyl)-ethyl]-amide | N-[4-(2-amino-ethyl)-phenyl]-ethane-sulfonamide | 2 | δ 7.83(2H, m), 7.56(1H, m), 7.36(1H, m), 7.18–7.11(4H, m), 7.38–7.24(3H, m), 6.92(1H, d), 3.60(2H, t), 2.99(4H, m), 1.23(3H, s) | |
| 146 | 6 | 2-(2-chloro-4-fluoro-phenyl)-7-hydroxy-1H-benzoimidazole-4-carboxylic acid[2-(4-acetylamino-phenyl)-ethyl]-amide | N-[4-(2-amino-ethyl)-phenyl]-acetamide | 2 | δ 8.00~7.91(m, 2H), 7.57(d, 1H), 7.48~7.34(m, 3H), 7.19(d, 2H), 6.92(d, 1H), 3.66(t, 2H), 2.9(t, 2H), 2.09(s, 3H) | |
| 147 | 6 | 2-(2-chloro-4-fluoro-phenyl)-7-hydroxy-1H-benzoimidazole-4-carboxylic acid(2-morpholin-4-yl-ethyl)-amide | 2-morpholin-4-yl-ethylamine | 2 | δ 8.00~7.90(m, 2H), 7.60(d, 1H), 7.43(t, 1H), 6.95(d, 1H), 4.20~3.60(m, 8H), 3.46(t, 2H), 3.34~3.10(br, 2H) | |
| 148 | 6 | 2-(2-chloro-4-fluoro-phenyl)-7-hydroxy-1H-benzoimidazole-4-carboxylic acid[2-(4-methyl-piperazin-1-yl)-ethyl]-amide | 2-(4-methyl-piperazin-1-yl)-ethylamine | 2 | δ 7.98(m, 2H), 7.59(d, 1H), 7.40(t, 1H), 6.93(d, 1H), 3.80~3.50(br, 10H), 3.21(t, 2H), 2.95(s, 3H), 2.06(t, 2H) | |
| 149 | 6 | 2-(2-chloro-4-fluoro-phenyl)-7-hydroxy-1H-benzoimidazole-4-carboxylic acid[2-(4-pentanoylamino-phenyl)-ethyl]-amide | pentanoic acid [4-(2-amino-ethyl)-phenyl]-amide | 2 | δ 7.92~7.82(m, 2H), 7.57(d, 1H), 7.46~7.37(m, 3H), 7.20(d, 2H), 6.92(d, 1H), 3.66(t, 2H), 2.91(t, 2H), 2.34(t, 2H), 1.66(m, 2H), 1.40(m, 2H), 0.95(t, 3H) | |
| 150 | 6 | 2-(2-chloro-4-fluoro-phenyl)-7-hydroxy-1H-benzoimidazole-4-carboxylic acid[2-(4-hydroxy-phenyl)-ethyl]-amide | 4-hydroxyphenethylamine | 2 | δ 7.92~7.83(m, 2H), 7.62(d, 1H), 7.43(t, 1H), 7.07(d, 2H), 6.94(d, 1H), 6.69(d, 2H), 3.62(t, 2H), 2.85(t, 2H) | |
| 151 | 6 | 2-(2-chloro-4-fluoro-phenyl)-7-hydroxy-1H-benzoimidazole-4-carboxylic acid[2-(5-nitro-pyridin-2-ylamino)-ethyl]-amide | N-(5-nitro-pyridin-2-yl)-ethane-1,2-diamine | 2 | δ 8.85(s, 1H), 8.12(br, 1H), 7.79~7.85(m, 3H), 7.63(d, 1H), 7.42(t, 1H), 6.95(d, 1H), 6.62(br, 1H), 3.90~3.60(m, 4H) | |
| 152 | 6 | 2-(2-chloro-4-fluoro-phenyl)-7-hydroxy-1H-benzoimidazole-4-carboxylic acid[2-(5-methanesulfonylamino-pyridin-2-ylamino)-ethyl]-amide | N-[6-(2-amino-ethyl-amino)-pyridin-3-yl]-methanesulfonamide | 2 | δ 8.05~7.85(m, 3H), 7.79(d, 1H), 7.61(d, 1H), 7.42(t, 1H), 7.14(d, 1H), 6.94(d, 1H), 3.80~3.60(m, 4H), 2.92(t, 3H) | |
| 153 | 6 | 2-(2-chloro-4-fluoro-phenyl)-7-hydroxy-1H-benzoimidazole-4-carboxylic acid{2-[5-(toluene-4-sulfonylamino)-pyridin-2-ylamino]ethyl}-amide | N-[6-(2-amino-ethyl-amino)-pyridin-3-yl]-p-toluenesulfonamide | 2 | δ 7.92(m, 1H), 7.89(d, 1H), 7.58(d, 2H), 7.45(m, 3H), 7.29(m, 3H), 6.92(d, 1H), 6.78(d, 1H), 3.72(t, 2H), 3.61(t, 2H), 2.37(s, 3H) | |

TABLE 2-continued

| Com No. | Pre No. | Chemical compound | R⁴N(CH₂)ₙR⁵ | n | ¹H NMR(CH₃OH-d₄) | MW |
|---|---|---|---|---|---|---|
| 154 | 6 | 2-(2-chloro-4-fluoro-phenyl)-7-hydroxy-1H-benzoimidazole-4-carboxylic acid[2-(1H-imidazol-4-yl)-ethyl]-amide | histamine | 2 | δ 8.79(s, 1H), 8.00~7.0 2H), 7.62(d, 1H), 7.50~7.35(m, 2H), 6.93(d, 1H), 3.76(t, 2H), 3.76(t, 2H), 3.10(t, 2H) | |
| 155 | 6 | 2-(2-chloro-4-fluoro-phenyl)-7-hydroxy-1H-benzoimidazole-4-carboxylic acid[2-(5-acetylamino-pyridin-2-ylamino)-ethyl]-amide | N-[6-(2-amino-ethyl-amino)-pyridin-3-yl]-acetamide | 2 | δ 8.57(s, 1H), 8.10~7.95(m, 2H), 7.88(d, 1H), 7.74(d, 1H), 7.50~7.30(m, 2H), 6.95(d, 1H), 4.10(t, 2H), 3.65(t, 2H), 2.13(s, 3H) | |
| 156 | 6 | 2-(2-chloro-4-fluoro-phenyl)-7-hydroxy-1H-benzoimidazole-4-carboxylic acid(2-{4-[2-(4-methyl-piperazin-1-yl)-acetylamino]-phenyl}-ethyl)-amide | N-[4-(2-Amino-ethyl)-phenyl]-2-(4-methyl-piperazin-1-yl)-acetamide | 2 | δ 7.97~7.80(m, 2H), 7.61(d, 1H), 7.59(d, 2H), 7.40(t, 1H), 7.25(d, 2H), 6.92(d, 1H), 3.67(t, 2H), 3.34(s, 2H), 3.10~2.75(m, 13H) | |
| 157 | 6 | 2-(2-chloro-4-fluoro-phenyl)-7-hydroxy-1H-benzoimidazole-4-carboxylic acid(2-{4-[2-(4-ethyl-piperazin-1-yl)-acetyl-amino]-phenyl}-ethyl)amide | N-[4-(2-amino-ethyl)-phenyl]-2-(4-ethyl-piperazin-1-yl)-acetamide | 2 | δ 7.97~7.83(m, 2H), 7.61(d, 1H), 7.50(d, 2H), 7.39(t, 1H), 7.25(d, 2H), 6.91(d, 1H), 3.67(t, 2H), 3.34(s, 4H), 3.21(q, 2H), 3.05~2.75(m, 8H), 1.35(t, 3H) | |
| 158 | 6 | 2-(2-chloro-4-fluoro-phenyl)-7-hydroxy-1H-benzoimidazole-4-carboxylic acid{2-[4-(2-dimethylamino-acetylamino)-phenyl]-ethyl}-amide | N-[4-(2-amino-ethyl)-phenyl]-2-dimethyl-amino-acetamide | 2 | δ 7.99(m, 1H), 7.84~7.70(m, 2H), 7.52(d, 2H), 7.35~7.25(m, 3H), 6.77(d, 1H), 4.08(s, 2H), 3.73(s, 2H), 2.97(m, 8H) | |
| 159 | 6 | 2-(2-chloro-4-fluoro-phenyl)-7-hydroxy-1H-benzoimidazole-4-carboxylic acid{2-[4-(2-diethylmaino-acetylamino)-phenyl]-ethyl}-amide | N-[4-(2-amino-ethyl)-phenyl]-2-diethylamino-acetamide | 2 | δ 7.94~7.82(m, 2H), 7.60(d, 1H), 7.52(d, 2H), 7.40(t, 1H), 7.28(d, 2H), 6.89(d, 1H), 4.08(s, 2H), 3.68(t, 2H), 3.31(q, 4H), 2.94(t, 2H), 1.34(t, 6H) | |
| 160 | 7 | 2-(3-chloro-4-fluoro-phenyl)-7-hydroxy-1H-benzoimidazole-4-carboxylic acid{2-[4-(toluene-4-sulfonylamino)-phenyl]-ethyl}amide | N-[4-(2-amino-ethyl)-phenyl]-p-toluene-sulfonamide | 2 | (1H, d), 7.90(1H, m), 7.72(1H, d), 7.47(2H, d), 7.39(1H, m), 7.13–7.06(4H, m), 6.95(2H, d), 6.75(1H, d), 3.63(2H, t), 2.85(2H, t), 2.23(3H, s) | |
| 161 | 7 | 2-(3-chloro-4-fluoro-phenyl)-7-hydroxy-1H-benzoimidazole-4-carboxylic acid[2-(4-methanesulfonylamino-phenyl)-ethyl]-amide | N-[4-(2-amino-ethyl)-phenyl]-methane-sulfonamide | 2 | δ 8.19(1H, d), 7.95(1H, m), 7.74(1H, d), 7.42(1H, t), 7.24(2H, d), 7.13(2H, d), 6.75(1H, d), 3.68(2H, t), 2.91(2H, t), 2.81(3H, s) | |
| 162 | 1 | 7-hydroxy-2-phenyl-1H-benzo-imidazole-4-carboxylic acid butylamide | n-butylamine | 3 | δ 7.95–7.70(2H, m), 7.69(1H, d), 7.60–7.42(1H, m), 7.41–7.23(2H, m), 3.42(2H, t), 1.78–1.56(2H, m), 1.55–1.34(2H, t), 0.97(3H, t) | 309 |
| 163 | 1 | 7-Hydroxy-2-phenyl-1H-benzo-imidazole-4-carboxylic acid (3-amino-propyl)-amide | 1,3-diaminopropane | 3 | δ 8.10(1H, d), 7.90(1H, d), 7.68(1H, d), 7.67–7.53(3H, m), 6.81(1H, d), 3.65(2H, t), 3.22–3.00(2H, t), 2.05(2H, t) | 310 |
| 164 | 1 | 7-hydroxy-2-phenyl-1H-benzo-imidazole-4-carboxylic acid [3-(2-oxo-prolidine-1-yl)-propyl]-amide | 1-(3-aminopropyl)-2-prolidinone | 3 | δ 8.04(1H, d), 7.81(1H, d), 7.75–7.66(3H, m), 6.96(1H, d), 6.87(1H, d), 3.53–3.41(6H, m), 2.39(2H, t), 2.03(2H, t), 1.90(2H, m) | 378 |
| 165 | 1 | 7-hydroxy-2-phenyl-1H-benzo-imidazole-4-carboxylic acid (3-imidazol-1-yl-propyl)-amide | 1-(3-aminopropyl)-imidazole | 3 | δ 9.05(1H, s), 8.17(2H, d), 7.84(1H, d), 7.75(1H, s), 7.72–7.62(3H, m), 7.55(1H, s), 6.88(1H, d), 4.40(2H, t), 3.57(2H, t), 2.28(2H, m) | 361 |
| 166 | 1 | 7-hydroxy-2-phenyl-1H-benzo-imidazole-4-carboxylic acid (3-morpholine-4-yl-propyl)-amide | 4-(3-aminopropyl)-morpholine | 3 | δ 8.10–8.11(2H, d), 7.86(2H, d), 7.84–7.69(1H, m), 7.63–7.59(2H, m), 4.10(2H, t), 4.06(2H, t), 3.80(2H, t), 3.65(2H, t), 3.54(2H, t), 3.15(2H, t), 2.14(2H, m) | 380 |
| 167 | 1 | 7-hydroxy-2-phenyl-1H-benzo-imidazole-4-carboxylic acid [3-(2-methyl-imidazol-1-yl)-propyl]-amide | 3-(2-methyl-imidazol-1-yl)-propylamine | 3 | δ 8.18–8.11(2H, m), 7.84(1H, d), 7.73–7.63(4H, m), 7.40(1H, d), 6.89(1H, d), 4.28(2H, t), 3.59(2H, t), 2.63(3H, s), 2.25(2H, m) | |
| 168 | 2 | 2-(4-chloro-phenyl)-7-hydroxy-1H-benzoimidazole-4-carboxylic acid butylamide | n-butylamine | 3 | δ 8.10(2H, d), 7.88(1H, d), 7.66(2H, d), 6.92(1H, d), 3.42(2H, t), 1.78–1.56(2H, m), 1.55–1.34(2H, t), 0.97(3H, t) | 343 |
| 169 | 2 | 2-(4-chloro-phenyl)-7-hydroxy-1H-benzoimidazole-4-carboxylic acid[3-(2-oxoprolidin-1-yl)-propyl]-amide | 1-(3-aminopropyl)-2-pyrrolidone | 3 | δ 8.21–8.11(2H, m), 7.82(1H, d), 7.63–7.53(2H, m), 6.86(1H, d), 3.60–3.38(6H, m), 2.38(2H, t), 2.03(2H, t), 1.89(2H, m) | 412 |
| 170 | 2 | 2-(4-chloro-phenyl)-7-hydroxy-1H-benzoimidazole-4-carboxylic acid(3-imidazole-1-yl-propyl)-amide | 1-(3-aminopropyl)-imidazole | 3 | δ 9.03(1H, d), 8.18(2H, t), 7.81(1H, d), 7.74(1H, d), 7.64–7.53(3H, m), 6.84(1H, d), 4.40(2H, t), 3.60(2H, t), 2.29(2H, m) | 395 |

TABLE 2-continued

| Com No. | Pre No. | Chemical compound | $R^4N(CH_2)_nR^5$ | n | $^1H$ NMR($CH_3OH$-$d_4$) | MW |
|---|---|---|---|---|---|---|
| 171 | 2 | 2-(4-chloro-phenyl)-7-hydroxy-1H-benzoimidazole-4-carboxylic acid(3-morphorine-4-yl-propyl)-amide | 4-(3-aminopropyl)-morphorine | 3 | δ 8.21–8.10(2H, m), 7.85(1H, d), 7.61–7.54(2H, m), 6.80(1H, d), 4.05(2H, t), 3.81(2H, t), 3.68–3.46(4H, m), 3.17(2H, t), 2.11(2H, m) | 414 |
| 172 | 2 | 2-(4-chloro-phenyl)-7-hydroxy-1H-benzoimidazole-4-carboxylic acid[3-(2-pentyl-imidazol-1-yl)-propyl]-amide | 3-(2-phenyl-imidazol-1-yl)-propylamine | 3 | δ 8.13(2H, d), 7.87(1H, d), 7.70(1H, d), 7.64–7.53(5H, m), 7.47–7.25(3H, m), 6.80(1H, d), 4.41(2H, t), 3.53(1H, t), 2.27(2H, m) | 473 |
| 173 | 2 | 2-(4-chloro-phenyl)-7-hydroxy-1H-benzoimidazole-4-carboxylic acid[3-(4-methyl-imidazol-1-yl)-propyl]-amide | 3-(4-methyl-imidazole-1-yl)-propylamine | 3 | δ 8.85(1H, d), 8.17(2H, t), 7.87(1H, m), 7.68–7.57(2H, m), 7.40(1H, d), 6.89(1H, d), 4.32(2H, t), 3.59(2H, m), 2.37–2.20(5H, m) | 409 |
| 174 | 2 | 2-(4-chloro-phenyl)-7-hydroxy-1H-benzoimidazole-4-carboxylic acid[3-(4,5-dichloro-imidazol-1-yl)-propyl]-amide | 3-(4,5-dichloro-imidazole-1-yl)-propylamine | 3 | δ 8.13(2H, t), 7.85–7.78(2H, m), 7.65–7.55(2H, m), 6.87(1H, d), 4.18(2H, t), 3.54(2H, m), 2.18(2H, m) | 474 |
| 175 | 2 | 2-(4-chloro-phenyl)-7-hydroxy-1H-benzoimidazole-4-carboxylic acid[3-(2-methyl-imidazol-1-yl)-propyl]-amide | 3-(2-methyl-imidazole-1-yl)-propylamine | 3 | δ 8.21–8.09(3H, m), 7.68(1H, d), 7.60–7.55(3H, m), 7.36(1H, d), 4.28(2H, t), 3.63(2H, m), 2.60(3H, s), 2.28(2H, m) | 421 |
| 176 | 3 | 2-(2,4-dichloro-phenyl)-7-hydroxy-1H-benzoimidazole-4-carboxylic acid butylamide | n-butylaine | 3 | δ 8.10(2H, d), 7.88(1H, d), 7.66(2H, d), 7.37–7.23(4H, m), 6.92(1H, d), 3.42(2H, t), 1.78–1.56(2H, m), 1.55–1.34(2H, t), 0.97(3H, t) | 377 |
| 177 | 3 | 2-(2,4-dichloro-phenyl)-7-hydroxy-1H-benzoimidazole-4-carboxylic acid[3-(2-oxo-pyrolidin-1-yl)-propyl]-amide | 1-(3-aminopropyl)-2-pyrolidione | 3 | δ 8.07–7.74(3H, m), 7.73–7.49(1H, m), 6.90(1H, d), 3.60–3.38(6H, m), 2.38(2H, t), 2.03(2H, t), 1.89(2H, m) | 446 |
| 178 | 3 | 2-(2,4-dichloro-phenyl)-7-hydroxy-1H-benzoimidazole-4-carboxylic acid(3-imidazol-1-yl)-propyl)-amide | 1-(3-aminopropyl)-imidazole | 3 | δ 9.02(1H, s), 7.90–7.72(4H, m), 7.64–7.46(2H, m), 6.88(1H, d), 4.37(2H, t), 3.53(2H, t), 2.26(2H, m) | 429 |
| 179 | 3 | 2-(2,4-dichloro-phenyl)-7-hydroxy-1H-benzoimidazole-4-carboxylic acid(3-morphorin-4-yl-propyl)-amide | 4-(3-aminopropyl)-morphorine | 3 | δ 8.03–7.76(3H, m), 7.75–7.45(1H, m), 6.85(1H, d), 4.05(2H, t), 3.81(2H, t), 3.68–3.46(4H, m), 3.17(2H, t), 2.11(2H, m) | 448 |
| 180 | 3 | 2-(2,4-dichloro-phenyl)-7-hydroxy-1H-benzoimidazole-4-carboxylic acid[3-(2-phenyl-imidazol-1-yl)-propyl]-amide | 3-(2-phenyl-imidazol-1-yl)-propylamine | 3 | δ 8.15(d, 2H), 8.11(s, 1H), 7.86(s, 1H), 7.64~7.29(m, 5H), 7.29~7.25(m, 3H), 6.56(d, 1H), 4.41(t, 2H), 3.53(t, 2H), 2.27(q, 3H) | |
| 181 | 3 | 2-(2,4-dichloro-phenyl)-7-hydroxy-1H-benzoimidazole-4-carboxylic acid[3-(4-methyl-imidazol-1-yl)-propyl]-amide | 3-(4-methyl-imidazol-1-yl)-propylamine | 3 | δ 8.84(s, 1H), 7.91~7.73(m, 3H), 7.58(m, 1H), 7.38(s, 1H), 6.85(d, 1H), 4.29(t, 2H), 3.54(t, 2H), 2.34~2.25(m, 5H) | |
| 182 | 3 | 2-(2,4-dichloro-phenyl)-7-hydroxy-1H-benzoimidazole-4-carboxylic acid[3-(4,5-dichloro-imidazol-1-yl)-propyl]-amide | 3-(4,5-dichloro-imidazol-1-yl)-propylamine | 3 | δ 7.91~7.81(m, 4H), 7.52(s, 1H), 6.96(d, 1H), 4.15(t, 2H), 3.64(t, 2H), 2.13(q, 2H) | |
| 183 | 3 | 2-(2,4-dichloro-phenyl)-7-hydroxy-1H-benzoimidazole-4-carboxylic acid[3-(2-methyl-imidazol-1-yl)-propyl]-amide | 3-(2-methyl-imidazol-1-yl)-propylamine | 3 | δ 8.11~8.09(m, 3H), 7.61(m, 2H), 7.45(s, 1H), 6.88(d, 1H), 4.31(t, 2H), 3.46(t, 2H), 2.25(q, 2H), 2.33(s, 3H) | |
| 184 | 3 | 2-(2,4-dichloro-phenyl)-7-hydroxy-1H-benzoimidazole-4-carboxylic acid[3-(2-isopropyl-imidazol-1-yl)-propyl]-amide | 3-(2-isopropyl-imidazol-1-yl)-propylamine | 3 | δ 8.10~8.05(m, 3H), 7.58(m, 2H), 7.40(s, 1H), 6.88(d, 1H), 4.22(t, 2H), 3.60(t, 2H), 3.02(m, 1H), 1.3(s, 6H) | |
| 185 | 4 | 2-(4-fluoro-phenyl)-7-hydroxy-1H-benzoimidazole-4-carboxylic acid(3-imidazol-1-yl-propyl)-amide | 1-(3-aminopropyl)-imidazole | 3 | δ 8.89(1H, s), 8.21(2H, m), 7.83(1H, d), 7.49(1H, s), 7.38–7.24(3H, m), 6.90(1H, d), 4.31(2H, t), 3.56(2H, t), 2.38–2.33(2H, m) | |
| 186 | 4 | 2-(4-fluoro-phenyl)-7-hydroxy-1H-benzoimidazole-4-carboxylic acid[3-(2-isopropyl-imidazol-1-yl)-propyl]-amide | 3-(2-isopropyl-imidazol-1-yl)-propylamine | 3 | δ 8.26–8.21(2H, m), 7.84(1H, d), 7.65(1H, s), 7.46–7.37(3H, m), 6.88(1H, d), 4.34(2H, t), 3.62(2H, t), 3.52–3.43(1H, m), 2.27(2H, m), 1.36(6H, d) | |
| 187 | 4 | 2-(4-fluoro-phenyl)-7-hydroxy-1H-benzoimidazole-4-carboxylic acid[3-(4-methyl-imidazol-1-yl)-propyl]-amide | 3-(4-methyl-imidazole-1-yl)-propylamine | 3 | δ 8.89(1H, s), 8.21(2H, m), 7.83(1H, d), 7.43(3H, m), 6.90(1H, d), 4.31(2H, t), 3.56(2H, t), 2.38–2.27(5H, m) | |
| 188 | 4 | 2-(4-fluoro-phenyl)-7-hydroxy-1H-benzoimidazole-4-carboxylic acid[3-(2-methyl-imidazol-1-yl)-propyl]-amide | 3-(2-methyl-imidazol-1-yl)-propylamine | 3 | δ 8.29(2H, m), 7.78(1H, d), 7.49(1H, s), 7.35–7.24(3H, m), 6.70(1H, d), 4.26(2H, t), 3.64(2H, t), 2.95(3H, s), 2.28(2H, m) | |
| 189 | 4 | 2-(4-fluoro-phenyl)-7-hydroxy-1H-benzoimidazole-4-carboxylic acid[3-(2-ethyl-imidazol-1-yl)-propyl]-amide | 3-(2-ethyl-imidazol-1-yl)-propylamine | 3 | δ 8.27(2H, m), 7.79(1H, d), 7.51(1H, s), 7.33–7.25(3H, m), 6.72(1H, d), 4.27(2H, t), 3.65(2H, t), 2.90(2H, q), 2.28(2H, m), 1.25(3H, t) | |

TABLE 2-continued

| Com No. | Pre No. | Chemical compound | $R^4N(CH_2)_nR^5$ | n | $^1$H NMR(CH$_3$OH-d$_4$) | MW |
|---|---|---|---|---|---|---|
| 190 | 4 | 2-(4-fluoro-phenyl)-7-hydroxy-1H-benzoimidazole-4-carboxylic acid[3-(4,5-dichloro-imidazol-1-yl)-propyl]-amide | 3-(4,5-dichloro-imidazol-1-yl)-propylamine | 3 | δ 8.24–8.16(2H, m), 8.04(1H, d), 7.79(1H, d), 7.45–7.33(2H, m), 6.99–6.84(1H, m), 4.18(2H, t), 3.54(2H, t), 2.18(2H, m) | |
| 191 | 5 | 2-(2,4-difluoro-phenyl)-7-hydroxy-1H-benzoimidazole-4-carboxylic acid[3-(2-isopropyl)-imidazol-1-yl)-propyl]-amide | 3-(2-isopropyl-imidazol-1-yl)-propylamine | 3 | δ 8.20(1H, q), 8.18–7.97(1H, m), 7.86(1H, d), 7.64(1H, s), 7.45(1H, s), 7.39–7.24(1H, m), 6.86(1H, d), 4.33(2H, t), 3.60(2H, t), 3.49(1H, m), 2.26(2H, t), 1.36(3H, s), 1.34(3H, s) | |
| 192 | 5 | 2-(2,4-difluoro-phenyl)-7-hydroxy-1H-benzoimidazole-4-carboxylic acid(3-imidazol-1-yl-propyl)-amide | 1-(3-aminopropyl)-imidazole | 3 | δ 8.23(1H, q), 7.13–7.97(1H, m), 7.84(1H, d), 7.74(1H, s), 7.56(1H, s), 7.31–7.24(2H, m), 6.84(1H, d), 4.40(2H, t), 3.56(2H, t), 2.28(2H, t) | |
| 193 | 5 | 2-(2,4-difluoro-phenyl)-7-hydroxy-1H-benzoimidazole-4-carboxylic acid[3-(4-methyl-imidazol-1-yl)-propyl]-amide | 3-(4-methyl-imidazol-1-yl)-propylamine | 3 | δ 8.22(1H, q), 8.14–7.98(1H, m), 7.84(1H, d), 7.40–7.27(3H, m), 6.85(1H, d), 4.30(2H, t), 3.57(2H, t), 2.30(5H, m) | |
| 194 | 5 | 2-(2,4-difluoro-phenyl)-7-hydroxy-1H-benzoimidazole-4-carboxylic acid[3-(4,5-dichloro-imidazol-1-yl)-propyl]-amide | 3-(4,5-dichloro-imidazol-1-yl)propylamine | 3 | δ 8.19–8.03(2H, m), 7.81(2H, m), 7.39–7.29(1H, m), 6.85(1H, d), 4.17(2H, t), 3.52(2H, t), 2.16(2H, t) | |
| 195 | 5 | 2-(2,4-difluoro-phenyl)-7-hydroxy-1H-benzoimidazole-4-carboxylic acid[3-(2-methyl-imidazol-1-yl)-propyl]-amide | 3-(2-methyl-imidazol-1-yl)-propylamine | 3 | δ 8.21(1H, q), 8.06(1H, m), 7.85(1H, d), 7.62(1H, s), 7.39–7.27(2H, m), 6.87(1H, d), 4.30(2H, t), 3.58(2H, t), 2.63(3H, s), 2.25(2H, t) | |
| 196 | 5 | 2-(2,4-difluoro-phenyl)-7-hydroxy-1H-benzoimidazole-4-carboxylic acid[3-(2-ethyl-imidazol-1-yl)-propyl]-amide | 3-(2-ethyl-imidazol-1-yl)-propylamine | 3 | δ 8.29–8.05(2H, m), 7.86(1H, d), 7.64(1H, s), 7.43(1H, s), 7.38–7.31(1H, m), 6.95(1H, d), 4.29(2H, t), 3.57(2H, t), 3.03(2H, q), 2.25(2H, t), 1.34(3H, t) | |
| 197 | 5 | 2-(2,4-difluoro-phenyl)-7-hydroxy-1H-benzoimidazole-4-carboxylic acid[3-(4,5-dichloro-imidazol-1-yl)-propyl]-amide | 3-(4,5-dichloro-imidazol-1-yl)-propylamine | 3 | 8.19–8.03(2H, m), 7.81(2H, m), 7.39–7.29(1H, m), 6.85(1H, d), 4.17(2H, t), 3.52(2H, t), 2.16(2H, t) | |
| 198 | 6 | 2-(2-chloro-4-fluoro-phenyl)-7-hydroxy-1H-benzoimidazol-4-carboxylic acid(3-imidazol-1-yl-propyl)-amide | 1-(3-aminopropyl)-imidazole | 3 | δ 9.05(1H, s), 8.00–7.88(2H, m), 7.74(1H, s), 7.66–7.57(2H, m), 7.46–7.41(1H, m), 6.95(1H, d), 4.38(2H, t), 3.52(2H, t), 2.25(2H, t) | |
| 199 | 6 | 2-(2-chloro-4-fluoro-phenyl)-7-hydroxy-1H-benzoimidazol-4-carboxylic acid[3-(4-methyl-imidazol-1-yl)-propyl]-amide | 3-(4-methyl-imidazol-1-yl)-propylamine | 3 | δ 8.88(1H, s), 8.00–7.87(2H, m), 7.60(1H, m), 7.41(2H, m), 6.94(1H, d), 4.28(2H, t), 3.54(2H, t), 2.29(3H, s), 2.22(2H, t) | |
| 200 | 6 | 2-(2-chloro-4-fluoro-phenyl)-7-hydroxy-1H-benzoimidazol-4-carboxylic acid[3-(4,5-dichloro-imidazol-1-yl)-propyl]-amide | 3-(4,5-dichloro-imidazol-1-yl)-propylamine | 3 | δ 7.94(1H, m), 7.85(1H, m), 7.76(1H, s), 7.48(1H, d), 7.30(1H, t), 6.76(1H, d), 4.17(2H, t), 3.56(2H, t), 2.16(2H, t) | |
| 201 | 6 | 2-(2-chloro-4-fluoro-phenyl)-7-hydroxy-1H-benzoimidazol-4-carboxylic acid[3-(2-methyl-imidazol-1-yl)-propyl]-amide | 3-(2-methyl-imidazol-1-yl)-propylamine | 3 | δ 7.83(1H, m), 7.50(1H, m), 7.39(1H, s), 7.23(2H, m), 7.13(1H, s), 6.76(1H, d), 4.20(2H, t), 3.57(2H, t), 2.47(3H, s), 2.03(2H, t) | |
| 202 | 7 | 2-(3-chloro-4-fluoro-phenyl)-7-hydroxy-1H-benzoimidazol-4-carboxylic acid[3-(4-methyl-imidazol-1-yl)-propyl]-amide | 3-(4-methyl-imidazol-1-yl)-propylamine | 3 | δ 8.87(1H, s), 8.37(1H, d), 8.17(1H, m), 7.83(1H, d), 7.59(1H, t), 7.40(1H, s), 6.84(1H, d), 4.33(2H, t), 3.60(2H, t), 2.25(5H, m) | |
| 203 | 7 | 2-(3-chloro-4-fluoro-phenyl)-7-hydroxy-1H-benzoimidazol-4-carboxylic acid(3-imidazol-1-yl-propyl)-amide | 1-(3-aminopropyl)-imidazol | 3 | δ 9.05(1H, s), 8.37(1H, d), 8.17(1H, m), 7.83(1H, m), 7.75(1H, s), 7.61–7.43(2H, m), 6.82(1H, d), 4.41(2H, t), 3.60(2H, t), 2.30(2H, t) | |

EXAMPLE 204

Preparation of 7-hydroxy-2-[4-(2-morpholin-4-yl-ethylamino)-phenyl]-1H-benzoimidazole-4-carboxylic acid [3-(4,5-dichloro-imidazol-1-yl)-propyl]-amide (1) Preparation of 3-[(4-nitro-benzimidoyl)-amino]-4-methoxy-benzoic acid methyl ester Anhydrous p-toluenesulfonic acid (6.30 g, 33.1 mmol) was added to 50 ml of benzene and the resulting mixture was refluxed while removing water using a dean-stock trap. Added thereto were 3-amino-4-methoxy benzoic acid methyl ester (3 g, 16.6 mmol) obtained in step 1 of Preparation Example 1 and 4-nitrobenzonitrile (2.94 g, 19.9 mol), followed by stirring at 160° C. for 8 hours. The resulting solution was cooled to room temperature, the reaction was stopped by adding NaHCO$_3$ thereto, extracted with ethyl acetate, the extract was dried over MgSO$_4$ and concentrated under a reduced pressure. The resulting residue was purified by silica gel column chromatography to obtain the title compound (2.83 g, 8.59 mmol) in a yield of 52%.

$^1$H NMR (CDCl$_3$): δ 8.12–8.09 (m, 2H), 7.82 (d,1H), 7.70–7.69 (m, 1H), 6.98 (d, 1H), 4.91 (bs, 2H), 3.89(s, 6H)

(2) Preparation of 2-(4-nitro-phenyl)-7-methoxy-1H-benzoimidazole-4-carboxylic acid methyl ester 3-[(4-nitro-benzimidoyl)-amino]-4-methoxy-benzoic acid methyl ester (1.63 g, 4.95 mmol) was dissolved in 50% methanol, and 5% NaOCl was added dropwise thereto at room temperature. After checking the reaction by TLC, Na$_2$CO$_3$ (1.05 g, 9.38 mmol) seas added dropwise thereto and refluxed for 40 min. The resulting solution was cooled to room temperature, extracted with ethyl acetate and the extract was concentrated under a reduced pressure. The resulting residue was purified by silica gel column chromatography to obtain the title compound (0.75 g, 2.28 mmol) in a yield of 46%.

$^1$H NMR (CDCl$_3$): δ 10.90 (bs, 1H), 8.36–8.31 (m, 4H), 7.95 (d, 1H), 6.78 (d, 1H), 4.16 (s, 3H), 4.01 (s, 3H)

(3) Preparation of 2-(4-amino-phenyl)-7-hydroxy-1H-benzoimidazole-4-carboxylic acid 2-(4-nitro-phenyl)-7-methoxy-1H-benzoimidazole-4-carboxylic acid methyl ester (0.63 g, 1.92 mmol) obtained in step 2 was dissolved in 15 ml of EtOH, 0.1 g of 10% Pd/C was added thereto and stirred for 24 hours while hydrogen was supplied thereto from a balloon fulfilled with H$_2$ gas. The resulting solution was filtered and dried to obtain the title compound (0.57 g, 1.92 mmol) in a yield of 100%.

$^1$H NMR (CH$_3$OH-d$_4$): δ 10.48 (bs, 1H), 7.93 (d, 2H), 7.82 (d, 1H), 6.77 (d, 2H), 6.71 (d, 1H), 4.11 (s,3H), 3.98 (s, 3H)

(4) Preparation of 2-[(2-morpholinoethyl)-4-amino-phenyl]-7-methoxy-1H-benzoimidazole-4-carboxylic acid methyl ester 2-(4-amino-phenyl)-7-hydroxy-1H-benzoimidazole-4-carboxylic acid (160 mg, 0.54 mmol) obtained in step 3 was dissolved in DMF, cesium carbonate (0.53 g, 1.61 mmol) was added thereto and stirred for 5 min. Added thereto were 2-chloroethylmorpholine (0.12 g, 0.64 mmol) and potassium iodide (0.18 g, 1.08 mmol), followed by stirring for 24 hours. Then, the resulting solution was extracted with ethyl acetate, the extract was concentrated under a reduced pressure, and the residue was purified by silica gel chromatography to obtain the title compound (91 mg, 0.22 mmol) in a yield of 41%.

$^1$H NMR (CH$_3$OH-d$_4$): δ 7.97 (d, 1H), 7.57 (d, 2H), 6.77–6.73 (m, 3H), 4.54 (t, 2H), 4.11 (s, 3H), 3.99 (s, 3H), 3.57–3.55(m, 4H), 2.64 (t, 2H), 2.31–2.28 (m, 4H)

(5) Preparation of 2-[(2-morpholinoethyl)-4-amino-phenyl]-7-methoxy-1H-benzoimidazole-4-carboxylic acid-[3-(4,5-dichloro-imidazol-1-yl)-propyl]-amide 2-[(2-morpholinoethyl)-4-amino-phenyl]-7-methoxy-1H-benzoimidazole-4-carboxylic acid methyl ester (22 mg, 0.05 mmol) was dissolved in THF/H$_2$O, LiOHH$_2$O (6.7 mg, 0.16 mmol) was added thereto and stirred at room temperature. The resulting solution was filtered to remove residual LiOHH$_2$O, and the solvent was removed. The residue was dried and dissolved in DMF. Added thereto were 4,5-dichloro-1-(3-aminopropyl)imidazole (12.5 mg, 0.06 mmol), EDCI (30.9 mg, 0.16 mmol), DMAP (65.6 mg, 0.54 mmol) and HOBt (21.8 mg, 0.16 mmol), followed by stirring at room temperature. The resulting solution was extracted with ethyl acetate and concentrated under a reduced pressure. The resulting residue was purified by silica gel chromatography to obtain the title compound (19 mg, 0.03 mmol) in a yield of 63%.

$^1$H NMR (CH$_3$OH-d$_4$): δ 7.93 (d, 1H), 7.77–7.75 (m, 3H), 7.52 (d, 2H), 6.92 (d, 1H), 4.17 (t, 2H), 4.06–4.02 (m, 5H), 3.58–3.56 (m, 4H), 3.50 (t, 2H), 2.66 (t, 2H), 2.31–2.29 (m, 4H), 2.16 (q, 2H)

(6) Preparation of 2-[(2-morpholinoethyl)-4-amino-phenyl]-7-hydroxy-1H-benzoimidazole-4-carboxylic acid-[3-(4,5-dichloro-imidazol-1-yl)-propyl]-amide 2-[(2-morpholinoethyl)-4-amino-phenyl]-7-methoxy-1H-benzoimidazole-4-carboxylic acid-[3-(4,5-dichloro-imidazol-1-yl)-propyl]-amide (15 mg, 0.03 mmol) obtained in step 5 was dissolved in MC, BBr$_3$ (1.0M solution in MC, 0.3 mL, 0.3 mmol) was added thereto and stirred at room temperature for 48 hours. The reaction was stopped by adding water thereto and the resulting solution was extracted with MC/MeOH (7:1). The extract was concentrated under a reduced pressure and purified by silica gel chromatography to obtain the title compound (5.9 mg, 0.01 mmol) in a yield of 40%.

$^1$H NMR (CH$_3$OH-d$_4$): δ 7.95 (d, 1H), 7.81–7.79 (m, 4H), 7.55 (d, 1H), 6.94 (d, 1H), 4.15 (t, 2H), 3.94 (t, 2H), 3.59 (t, 2H), 3.58–3.56 (m, 4H), 2.64 (t, 2H), 2.32–2.30 (m, 4H), 2.18 (q, 2H)

TEST EXAMPLE 1

Assay for GSK-3β inhibiting activity

The GSK-3β inhibiting activity was determined in accordance with the method of Shultz et al. described in U.S. Pat. No. 6,153,618, with minor modifications by using phospho-CREB peptide as a substrate.

First, PCR (polymerase chain reaction) was carried out using human DNA as a template as well as primers which were designed to correspond to the 3'- and 5' ends of the polynucleotide coding human GSK-3β gene (Genbank Accession No.: L33801). The BamH1/XhoI fragment of the amplified PCR product thus obtained was inserted into the pGex vector between the BamH1 and XhoI sites, and the vector obtained was transformed into E. coli BL21(DE3). The transformed cells thus obtained was incubated in LB agar plates (1% Bacto-trypton, 0.5% yeast extract, 1% NaCl) containing ampicillin (100 μl/ml) until the optical density at 600 nm reached about 0.5. The cultured mixture was cooled to 18° C. and isopropyl β-D-thiogalacto-pyranoside (IPTG) was added thereto to a final concentration of 0.5 mM. After 16 hours, the resultant was centrifuged at 10,000×g for 10 min, the collected cells were suspended in a buffer solution (30 mM Tris-HCl (pH 7.5), 100 mM NaCl, 5% glycerol, 2 mM DTT) and the cells were disrupted using Sonic Dismembrator (Fisher, U.S.A.) in a ice bath. The resulting solution was centrifuged at 16,000 rpm for 30 minutes. The supernatant was connected to GST (Glutathione-S-transferase) column (Pharmacia Biotech, U.S.A.) equilibrated in the same buffer solution, purified by glutathione affinity chromatography (eluent: 5 mM glutathione), and then, digested with thrombin to cleave the connecting site between the GST moiety and GSK-3β protein. The purified GSK-3β protein was diluted in a buffer solution (20 mM HEPES (pH 7.5), 5% glycerol, 2 mM DTT) to a final concentration of 50 mM NaCl and the resulting solution was subjected to mono S column chromatography (eluent: linear gradient from 0M to 1M NaCl buffer) using mono S column (Pharmacia Biotech, U.S.A.) equilibrated in the same buffer solution to obtain GSK-3β protein.

100 nM GSK-3β protein, 12.5 mM each of the compounds prepared in Examples 1 to 204 dissolved in DMSO, an assay buffer (50 mM Tris-HCl, pH 7.5, 10 mM MgCl$_2$, 1 mM EGTA, 1 mM DTT), 100 μM phospho-CREB peptide (NEB, USA), 100 μM ATP, $^{32}$P-ATP and 1 μCi were reacted at 30° C. for 1 hour. The reaction was stopped by adding 5 μl of 5% phosphoric acid to 25 μl of the resulting solution. The resulting mixture was centrifuged at 15,000 rpm for 10 min, 20 μl of the supernatant was added dropwise to Whatman p81 filter paper, and then, the resulting filter paper was washed with 0.5% phosphate buffer for 10 min. The filter paper was further washed 3 times and the enzymatic activity was determined by examining the extent of phospho-CREB peptide phosphorylation which is represented by the unit of count per minute (CPM), measured with a β-counter (Packard, USA).

The GSK-3β inhibiting activity was then calculated in accordance with the following equation:

$$\text{Degree of Inhibition}(\%) = 100 \times \left[1 - \frac{\text{CPM(sample)} - \text{CPM(blank)}}{\text{CPM(control)} - \text{CPM(blank)}}\right]$$

wherein the blank represents a value obtained without the use of the enzyme and the compound of the present invention, and the control, in the absence of the compound of the present invention.

The IC$_{50}$ value of the inventive compound was determined from the degree of inhibition (%) and the result is shown in Table 3.

TABLE 3

| Exam. | IC$_{50}$ (μM) | Exam. | IC$_{50}$ (μM) | Exam. | IC$_{50}$ (μM) | Exam. | IC$_{50}$ (μM) |
|---|---|---|---|---|---|---|---|
| 1 | >1 | 52 | >1 | 103 | >5 | 154 | >1 |
| 2 | >1 | 53 | >1 | 104 | >1 | 155 | >1 |
| 3 | >1 | 54 | >1 | 105 | 0.05 | 156 | 0.28 |
| 4 | >1 | 55 | >1 | 106 | 0.015 | 157 | 0.49 |
| 5 | 0.3 | 56 | 0.7 | 107 | 0.05 | 158 | 0.23 |
| 6 | >1 | 57 | 0.58 | 108 | >1 | 159 | 0.68 |
| 7 | >1 | 58 | 0.67 | 109 | 0.03 | 160 | >1 |
| 8 | >1 | 59 | 0.16 | 110 | 0.28 | 161 | 0.09 |
| 9 | 0.18 | 60 | 0.35 | 111 | >1 | 162 | 0.24 |
| 10 | 0.04 | 61 | >1 | 112 | 0.04 | 163 | >1 |
| 11 | >5 | 62 | >1 | 113 | 0.19 | 164 | 0.84 |
| 12 | 0.2 | 63 | 0.45 | 114 | 0.001 | 165 | 0.08 |
| 13 | 0.36 | 64 | 0.03 | 115 | 0.026 | 166 | >1 |
| 14 | >1 | 65 | 0.06 | 116 | 0.003 | 167 | 0.1 |
| 15 | 0.11 | 66 | >1 | 117 | 0.03 | 168 | >1 |
| 16 | 0.7 | 67 | 0.16 | 118 | >5 | 169 | >1 |
| 17 | 0.24 | 68 | 0.017 | 119 | >5 | 170 | 0.19 |
| 18 | >1 | 69 | >1 | 120 | 0.07 | 171 | >1 |
| 19 | >1 | 70 | >1 | 121 | 0.03 | 172 | 0.8 |
| 20 | 4.1 | 71 | >1 | 122 | 0.2 | 173 | 0.1 |
| 21 | >5 | 72 | 0.12 | 123 | 0.05 | 174 | 0.04 |
| 22 | >1 | 73 | >1 | 124 | 0.07 | 175 | 0.28 |
| 23 | 0.68 | 74 | >1 | 125 | >1 | 176 | 0.45 |
| 24 | >5 | 75 | 0.009 | 126 | >1 | 177 | 0.2 |
| 25 | >1 | 76 | 0.05 | 127 | 0.18 | 178 | 0.04 |
| 26 | >1 | 77 | 0.033 | 128 | 0.15 | 179 | >1 |
| 27 | >1 | 78 | >1 | 129 | 0.12 | 180 | 0.21 |
| 28 | 0.74 | 79 | 0.12 | 130 | 0.33 | 181 | 0.03 |
| 29 | 0.08 | 80 | 0.07 | 131 | 0.17 | 182 | 0.008 |
| 30 | >1 | 81 | >1 | 132 | 0.19 | 183 | 0.06 |
| 31 | >1 | 82 | >1 | 133 | >1 | 184 | 0.15 |
| 32 | 0.5 | 83 | >1 | 134 | 0.04 | 185 | >1 |
| 33 | >1 | 84 | >1 | 135 | >1 | 186 | 0.05 |
| 34 | >1 | 85 | >5 | 136 | 0.24 | 187 | 0.01 |
| 35 | 0.007 | 86 | 0.25 | 137 | 0.005 | 188 | 0.002 |
| 36 | >1 | 87 | 0.23 | 138 | >1 | 189 | >1 |
| 37 | >1 | 88 | 0.22 | 139 | 0.12 | 190 | 0.006 |
| 38 | >1 | 89 | 0.32 | 140 | >1 | 191 | 0.09 |
| 39 | >1 | 90 | 0.13 | 141 | 0.043 | 192 | 0.008 |
| 40 | >1 | 91 | >1 | 142 | 0.001 | 193 | 0.02 |
| 41 | >1 | 92 | 0.08 | 143 | 0.002 | 194 | 0.004 |
| 42 | >1 | 93 | >1 | 144 | 0.006 | 195 | 0.03 |
| 43 | >1 | 94 | >5 | 145 | 0.002 | 196 | 0.02 |
| 44 | >1 | 95 | >1 | 146 | 0.07 | 197 | 0.003 |
| 45 | 0.02 | 96 | 0.022 | 147 | 0.21 | 198 | 0.02 |
| 46 | >5 | 97 | 0.17 | 148 | >1 | 199 | 0.01 |
| 47 | >5 | 98 | >1 | 149 | 0.14 | 200 | 0.002 |
| 48 | >5 | 99 | 1 | 150 | 0.06 | 201 | 0.07 |
| 49 | 0.6 | 100 | 0.2 | 151 | 0.4 | 202 | 0.009 |
| 50 | 0.6 | 101 | >1 | 152 | 0.24 | 203 | 0.003 |
| 51 | 0.87 | 102 | 0.23 | 153 | 0.05 | 204 | >5 |

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I), or a pharmaceutically acceptable salt, hydrate, solvate or isomer thereof:

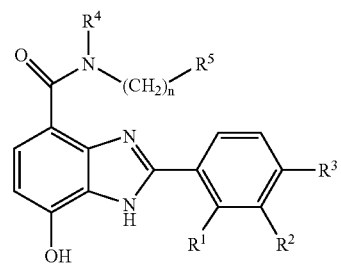

wherein:

n is 0, 1, 2 or 3;

R$^1$, R$^2$ and R$^3$ are each independently hydrogen, hydroxy, halogen or morpholin-1-yl-ethylamino;

R$^4$ is hydrogen; and

R$^5$ is linear or cyclic C$_1$–C$_6$ alkyl optionally having one or more substituents, the carbon of the alkyl being optionally replaced with nitrogen, sulfur or oxygen, wherein the substituent is: hydroxy; halogen; allyloxy; alkyl; amino; alkylamino; carboxyl; nitro; sulfonylamido; alkanesulfonyl; amido; an aromatic group optionally having one or more substituents selected from the group consisting of hydroxy, halogen, alkyloxy, alkyl, amino, alkylamino, carboxyl, nitro, amido, dioxoisoindole and sulfonylamino; an aromatic group having one or more substituents selected from the group consisting of hydroxy, halogen, alkyloxy, alkyl, amino, alkylamino, carboxyl, nitro and amido, the aromatic ring having nitrogen, sulfur or oxygen; or cyclic C$_3$–C$_8$ alkyl optionally having one or more substituents selected from the group consisting of hydroxy, halogen, alkyloxy, alkyl, amino, alkylamino, carboxyl, nitro and amido;

an aromatic group optionally having one or more substituents, the aromatic ring having optional nitrogen, sulfur or oxygen, wherein the substituent is; hydroxy;

halogen; alkyloxy; alkyl; amino; alkylamino; carboxyl; nitro; sulfonylamido, alkanesulfonyl; amido; or linear or cyclic $C_1$–$C_6$ alkyl optionally having one or more substituents, the alkyl having an optional nitrogen, sulfur or oxygen linkage and the substituent of the alkyl being: hydroxy; halogen; alkyloxy; alkyl; amino; alkylamino; carboxyl; nitro; sulfonylamido, alkanesulfonyl; amido; an aromatic group optionally having one or more substituents selected from the group consisting of hydroxy; halogen; alkyloxy; alkyl; amino; alkylamino; carboxyl; nitro; amido; dioxoisoindole; and a sulfonylamino having an aromatic group substituted with hydroxy, halogen, alkyloxy, alkyl, amino, alkylamino, carboxyl, nitro, sulfonylamido, alkanesulfonyl or amido; an aromatic group optionally having one or more substituents selected from the group consisting of hydroxy, halogen, alkyloxy, alkyl, amino, alkylamino, carboxyl, nitro, sulfonylamide, alkanesulfonyl and amido, the aromatic ring containing nitrogen, sulfur or oxygen; or a cyclic $C_3$–$C_8$ alkyl optionally having one or more substituents selected from the group consisting of hydroxy, halogen, alkyloxy, alkyl, amino, alkylamino, carboxyl, nitro and amido; or $R^4$ and $R^5$ form, together with the —N—$(CH_2)_n$— moiety to which they are attached, a nitrogen heterocycle optionally having one or more substituents selected from the group consisting of OH, $NH_2$, $NO_2$, the heterocycle containing optional nitrogen or oxygen.

2. The compound of claim 1, wherein $R^5$ is $C^1$–$C^4$ alkyl optionally having one or more substituents selected from the group consisting of OH, $NH_2$, $NO_2$, and an aromatic group, the aromatic group optionally having one or more substituents selected from the group consisting of OH, $C^1$–$C^4$ alkyloxy, $NH_2$, $NO_2$, methanesulfonylamino, ethanesulfonylamino, tolunesulfonylamino and dioxoisoindole; cyclic $C_3$–$C_8$ alkyl optionally having one or more substituents selected from the group consisting of OH, $NH_2$ and $NO_2$; $C_1$–$C_4$ alkyl carrying a morpholine or oxopyrrolidine group which is optionally substituted with OH, $NH_2$, $NO_2$ or —O—; $C_1$–$C_4$ alkyl or $C_1$–$C_4$ aminoalkyl carrying a pyrrole, pyrazole, imidazole, 1,2,3-triazole, 1,2,4-triazole, isoxazole, oxazole, isothiazole, thiazolidine, thiazole, 1,2,5-oxadiazole, 1,2,3-oxadiazole, 1,2,5-thiadiazole, 1,2,3-thiadiazole, 1,3,4-oxadiazole, 1,3,4-thiadiazole, pyridine, pyrimidine or triazine group which is optionally having one or more substituents selected from the group consisting of Cl, OH, $NH_2$, $NO_2$, $C_1$–$C_4$ and phenyl;

cyclic $C_3$–$C_8$ alkyl optionally having one or more substituents selected from the group consisting of OH, $NH_2$ and $NO_2$;

an aromatic group optionally having one or more substituents selected from the group consisting of OH; $NH_2$; hydroxyalkyl; aminoalkyl; $NO_2$; and a $C_1$–$C_4$ alkyl group optionally having one or more substituents selected from the group consisting of OH, $NH_2$, $NO_2$, methanesulfonylamino, ethanesulfonylamino, tolunesulfonylamino, dioxoisoindole and thiophensulfonylamino; or $R^4$ $R^5$ form, together with the —N—$(CH_2)_n$— moiety to which they are attached, a nitrogen heterocycle optionally having one or more substituents selected from the group consisting of OH, $NH_2$ and $NO_2$, the heterocycle containing 1 to 3 nitrogen, sulfur or oxygen atom.

3. The compound of claim 1, wherein $R^5$ is $C_1$–$C_4$ alkyl optionally having one or more substituents selected from the group consisting of OH, $NH_2$, $NO_2$, morpholine, nitropyridineamino, pyridine, oxopyrrolidin, imidazole optionally having a Cl, $CH_3$ or phenyl substituent; and phenyl optionally having one or more substituents selected from the group consisting of OH, $NH_2$, methoxy, $NO_2$, methanesulfonylamino, ethanesulfonylamino, tolunesulfonylamino and dioxoisoindole;

cyclic $C_3$–$C_8$ alkyl optionally having one or more substituents selected from the group consisting of OH, $NH_2$ and $NO_2$;

phenyl optionally having one or more substituents selected from the group consisting of OH; $NH_2$; $NO_2$; and $C_1$–$C_4$ alkyl optionally having a OH, $NH_2$, $NO_2$, methanesulfonylamino, ethanesulfonylamino, tolunesulfonylamino, dioxoisoindole or thiophensulfonylamino substituent; or $R^4$ and $R^5$ form, together with —N—$(CH_2)_n$— moiety to which they are attached, a piperidine ring optionally having one or more substituents selected from the group consisting of OH, $NH_2$ and $NO_2$.

4. A process for preparing the compound of formula (IA) which comprises reacting 3-amino-4-methoxy benzoic acid (compound II) and an alcohol to obtain compound (III);

adding anhydrous p-toluenesulfonic acid and benzonitrile to the compound (III) thus obtained, refluxing the mixture at 80 to 200° C., adding NaOCl thereto at room temperature and purifying by silica gel column chromatography to obtain compound (IV);

dissolving the compound (IV) thus obtained in an alcohol, adding an aqueous alkali solution thereto and refluxing the mixture to obtain compound (V);

dissolving the compound (V) thus obtained in an organic solvent, adding a Lewis acid thereto and refluxing the mixture to obtain compound (VI);

dissolving the compound (V) thus obtained in alcohol, adding a strong acid thereto at room temperature and refluxing the mixture to obtain compound (VII);

dissolving the compound (VII) thus obtained and (4-bromomethylphenoxy)-methyl polystyrene Wang resin in an organic solvent, adding a base and KI thereto and stirring the mixture at 50 to 60° C. for 1 to 24 hours to obtain compound (VIII);

dissolving the compound (VIII) thus obtained in an organic solvent, adding an alcohol solution of an alkali hydroxide thereto and refluxing the mixture to obtain compound (IX);

dissolving the compound (IX) thus obtained in an organic solvent, adding $R^4N(CH_2),R^5$ and a coupling agent thereto and stirring the mixture at room temperature to obtain compound (X); and dissolving the compound (X) thus obtained in $CH_2Cl_2$, adding trifluoroacetic acid thereto and stirring the mixture at room temperature to obtain compound (Ia):

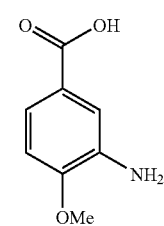

II

-continued

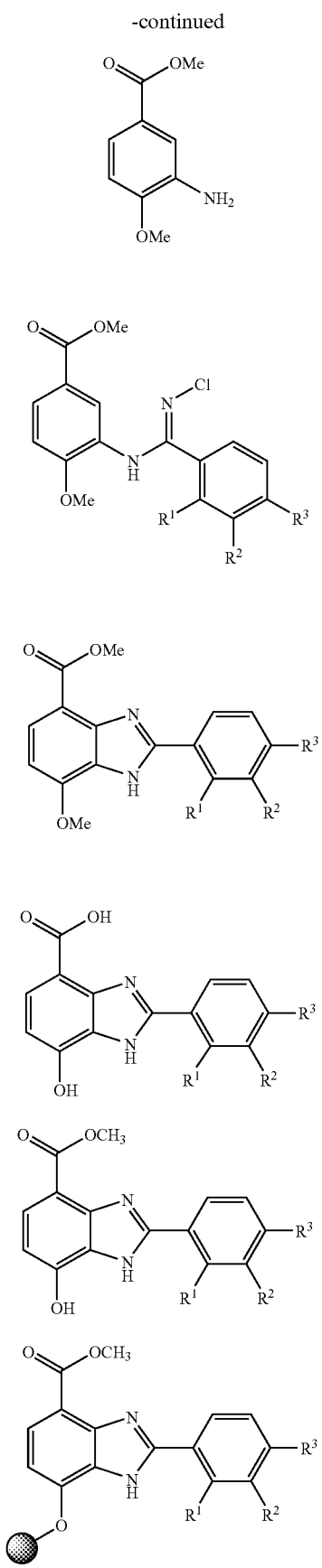

wherein, n, $R^1$, $R^2$, $R^3$, $R^4$ and $R^5$ have the same meanings as defined in claim 1.

5. A process for preparing the compound of formula (Ib) which comprises reacting 3-amino-4-methoxy benzoic acid (compound II) and an alcohol to obtain compound (III);

adding p-toluenesulfonic acid, benzene and 4-nitrobenzonitrile thereto, refluxing the mixture at 80 to 200° C., adding NaOCl thereto at room temperature and purifying by silica gel column chromatography to obtain compound (XI);

dissolving the compound (XI) thus obtained in an organic solvent, adding an aqueous alkali solution thereto, refluxing the mixture and purifying by silica gel column chromatography to obtain compound (XII);

dissolving the compound (XII) thus obtained in an alcohol, adding Pd/C thereto and refluxing the mixture to obtain compound (XIII);

dissolving the compound (XIII) thus obtained in an organic solvent, adding a base, 2-chloroethylmorphine and potassium iodide thereto and stirring the mixture at room temperature to obtain compound (XIV);

dissolving the compound (XIV) obtained thus in an organic solvent, adding an alkali hydrate, stirring the mixture at room temperature to obtain compound (XV);

dissolving the compound (XV) thus obtained in an organic solvent, adding 4,5-dichloro-1-(3-aminopropyl) imidazole and a coupling agent, stirring the mixture at room temperature and purifying by silica gel column chromatography to obtain compound (XVI); and dissolving the compound (XVI) thus obtained in MC, adding a Lewis acid thereto, stirring the mixture, concentrating the resulting solution under a reduced pressure and purifying by silica gel column chromatography to obtain compound (Ib)

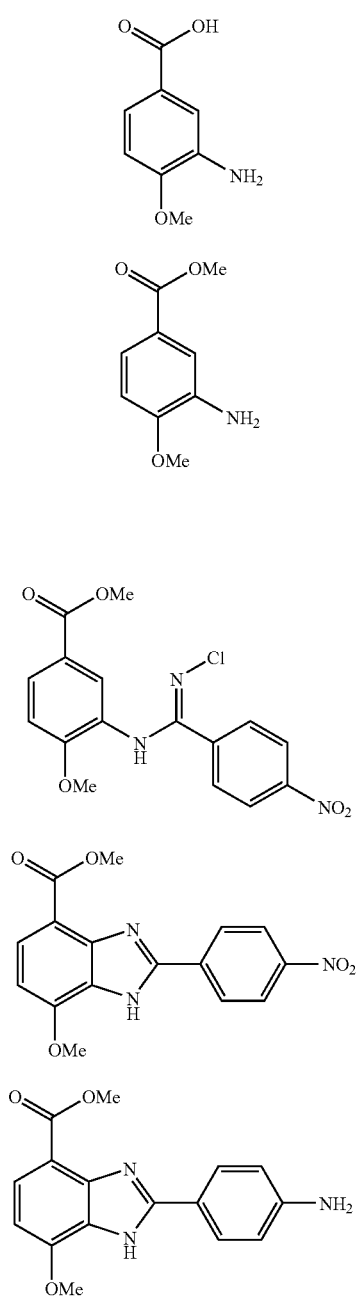

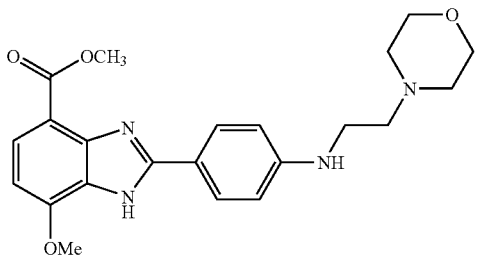

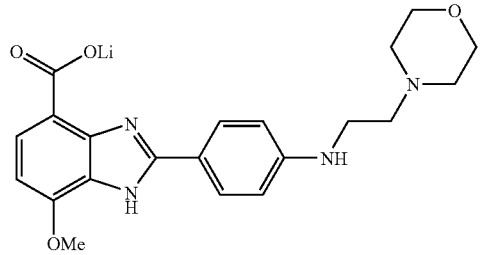

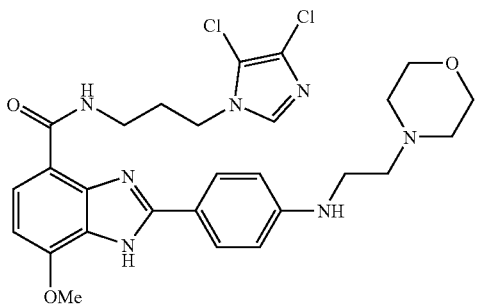

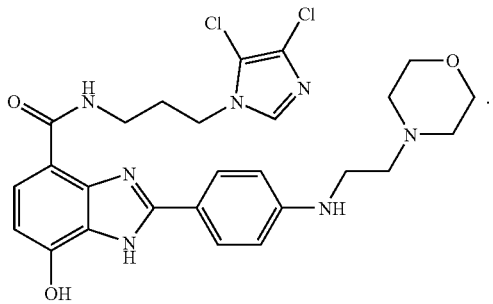

6. A pharmaceutical composition for inhibiting GSK-3β comprising the compound of claim 1 as an active ingredient and a pharmaceutically acceptable carrier.

* * * * *